United States Patent
Schnider et al.

(10) Patent No.: US 11,964,986 B1
(45) Date of Patent: Apr. 23, 2024

(54) 9-OXO-9,10-DIHYDRO-6H-PYRANO [3,2-B:4,5-B']DIPYRIDINE-8-CARBOXYLIC ACID DERIVATIVES

(71) Applicant: REJUVERON TELOMERE THERAPEUTICS AG, Schlieren (CH)

(72) Inventors: Patrick Schnider, Bottmingen (CH); Fedor Romanov Michailidis, Rheinfelden (CH); Chien-Chi Hsiao, Zürich (CH)

(73) Assignee: REJUVERON TELOMERE THERAPEUTICS AG, Schlieren (CH)

( * ) Notice: Subject to any disclaimer, the term of this patent is extended or adjusted under 35 U.S.C. 154(b) by 0 days.

(21) Appl. No.: 18/217,914

(22) Filed: Jul. 3, 2023

(51) Int. Cl.
  *C07D 491/20* (2006.01)
  *C07D 491/147* (2006.01)

(52) U.S. Cl.
  CPC ................................ *C07D 491/147* (2013.01)

(58) Field of Classification Search
  CPC .............. C07D 491/20; C07D 491/147; A61K 31/4375; A61K 31/438
  USPC .............................. 546/15, 83; 514/278, 293
  See application file for complete search history.

(56) References Cited

FOREIGN PATENT DOCUMENTS

| | | |
|---|---|---|
| CN | 112592343 A | 4/2021 |
| WO | 2013/033228 A1 | 3/2013 |
| WO | 2015/113990 A1 | 8/2015 |
| WO | 2016/039938 A1 | 3/2016 |
| WO | 2019/110352 A1 | 6/2019 |
| WO | 2019/177937 A1 | 9/2019 |
| WO | 2020/051375 A2 | 3/2020 |
| WO | 2020/239656 A1 | 12/2020 |
| WO | 2021/027566 A1 | 2/2021 |
| WO | 2021/055425 A2 | 3/2021 |
| WO | 2022/216552 A2 | 10/2022 |

OTHER PUBLICATIONS

Diane H Moon et al. "Poly(A)-Specific Ribonuclease (PARN) Mediates 3'-END Maturation of the Telomerase RNA Component". Nature Genetics, Advance Online Publication, 2015, pp. 1-7.

*Primary Examiner* — Jeffrey H Murray
(74) *Attorney, Agent, or Firm* — Oliff PLC

(57) ABSTRACT

The present invention relates to 9-oxo-9,10-dihydro-6H-pyrano[3,2-b:4,5-b']dipyridine-8-carboxylic acid derivatives, their manufacture, pharmaceutical compositions containing them and their use as a medicament.

25 Claims, 3 Drawing Sheets

9-OXO-9,10-DIHYDRO-6H-PYRANO [3,2-B:4,5-B']DIPYRIDINE-8-CARBOXYLIC ACID DERIVATIVES

The present invention relates to 9-oxo-9,10-dihydro-6H-pyrano[3,2-b:4,5-b']dipyridine-8-carboxylic acid derivatives, their manufacture, pharmaceutical compositions containing them and their use as a medicament.

Telomeres are DNA-protein structures, which constitute a protective cap at the end of linear chromosomes and function to maintain genome integrity. A complex of six different proteins (TRF1, TRF2, TPP1, POT1, TIN1 and RAP1) assembles at telomeres and plays crucial roles in maintaining telomere stability and preventing DNA ends from being recognized as double strand breaks. The inability of the conventional DNA polymerase to replicate linear chromosome ends results in telomere attrition and progressive telomere shortening at every cell division, a process implicated in cellular aging. Hence differentiated cells have a limited replicative potential, known as "Hayflick limit". Once the cells have reached this limit, critically short telomeres lose their protective properties and trigger the activation of the DNA damage response (DDR) machinery. Ultimately, DDR forces cells to enter replicative senescence or apoptosis to prevent aberrant DNA repair and chromosomal fusions.

In cells with high proliferative potential (germ cells and undifferentiated stem and progenitor cells of the skin, intestine, hematopoietic system and testes), telomeres are maintained by the telomerase holoenzyme, a ribonucleoprotein (RNP) complex. The catalytic core of the human telomerase holoenzyme consists of the reverse transcriptase hTERT, which is expressed only in undifferentiated stem and progenitor cells, and the telomerase RNA component (TERC), which is present in all cells. TERC provides a scaffold for the assembly of the telomerase RNP complex and functions as a RNA template for the addition of nucleotide repeats to the end of linear chromosomes. Additional cofactors, such as the telomerase Cajal body protein (TCAB), the nuclear assembly factor 1 ribonucleoprotein (NAF1) and the poly (A)-specific ribonuclease (PARN) play a major role in telomerase biogenesis, TERC maturation and stability while dyskerin (DKC1) and its associated factors (NOP10, NHP2 and GAR1) are part of the telomerase RNP complex and are required for its assembly.

Considering the function of the human telomerase complex in maintaining the proliferative potential of stem cells, mutations in telomerase components that affect TERC stability and disrupt proper telomere metabolism are responsible for telomere biology disorders (TBDs). Telomere biology disorders or telomeropathies are multi-organ syndromes comprising a number of rare and heterogeneous Mendelian diseases characterized by short telomeres, premature aging and shortened lifespan of patients. TBDs diagnosed in early childhood include dyskeratosis congenita (DC) and its most severe variants with a significantly shorter lifespan, such as Høyeraal-Hreidarsson syndrome (HHS), Revesz syndrome (RS) and Coats plus syndrome (CPS). The most prevalent forms of TBDs in adults are idiopathic pulmonary fibrosis (IPF) and liver cirrhosis.

Characteristic of all inherited TBDs is the high variability in the penetrance, severity and age of onset of the clinical features, which correlate with the extent of telomere shortening. In TBD families, short telomeres are inherited from the carrier parent, resulting in a progressive telomere shortening over generations and leading to genetic anticipation of the disease. For instance, while familial IPF can appear during adulthood in the first generation of an affected family, more severe TBDs will develop in the offspring at an earlier age of onset.

The etiology of late-onset liver cirrhosis and IPF can be familial or sporadic: mutations in components of the telomerase RNP complex and short telomeres are frequently detected in familial cases, while defects in telomere metabolism are responsible for only a minority of sporadic cases.

TBDs represent a high unmet medical need as there are no curative therapies, and only few treatment options are available for the clinical management of the diseases, like bone marrow and organ transplantation. Recent findings show that chemical inhibition of the non-canonical poly(A)-polymerase PAPD5 represents a novel treatment for TBDs characterized by impaired TERC biology.

TERC is synthesized as a precursor RNA and, in order to be converted into its mature and stable form, undergoes a maturation process which involves PAPD5 and PARN enzymes. PAPD5 catalyzes the addition of an oligoadenosine tail to the 3' end of the precursor TERC RNA (3'oligoadenylated TERC RNA) (FIG. 1 extended and unstable TERC); this modification targets TERC for degradation and hinders the assembly of a functional telomerase complex (FIG. 1b). In healthy physiological condition PAPD5 activity is counteracted by PARN, which trims the oligoadenosine tail of TERC and effects the accumulation of its mature and stable form (FIG. 1a). Thus, a proper equilibrium between PAPD5 and PARN activity is required to establish the steady-state levels of mature TERC and ensure the assembly of a functional telomerase holoenzyme (FIG. 1a). Loss of PARN due to genetic mutations results in an unbalanced equilibrium between the two forms of TERC and contributes to the onset of TBDs.

Indeed, WO2020051375 discloses that, in the context of TBDs caused by PARN mutations, a notable observation is the accumulation of extended and unstable forms of TERC. These transcripts are targeted for degradation, resulting in telomerase deficiency, subsequent telomere shortening and TBDs (FIG. 1b). It was also shown that inhibition of PAPD5 restores the levels of the mature form of TERC, enhances telomerase activity, and effects telomere restoration in patient cells bearing PARN mutations (FIG. 1c).

PAPD5 inhibition not only represents a therapeutic strategy for TBD patients with PARN mutations but it can also be applied in the presence of any other mutation that negatively affects the biogenesis and the maturation process of TERC (e.g. mutations in TCAB- and NAF1- encoding genes), the stability of the mature form of TERC, as well as the assembly of a functional telomerase RNP complex (which includes, but is not limited to, mutations in TERC-, TCAB-, ZCCHC8- and RNP-encoding genes).

Patients suffering from poikiloderma with neutropenia (PN) can also benefit from inhibition of PAPD5. Poikiloderma with neutropenia is a pediatric disorder caused by mutations in USB1, a deadenylase that counteracts PAPD5 poly-adenylation activity in the hematopoietic process. Patients with USB1 mutations display defective production of blood cells due to unrestrained PAPD5 activity. Inhibition of PAPD5 can rescue hematopoiesis and prevent defects in blood cell production.

Some PAPD5 inhibitors are under development for the treatment of chronic hepatitis B virus (HBV) infection (WO2019110352). It has been shown that HBV replication is most effectively suppressed by simultaneous inhibition of PAPD5 as well as another member of the PAP protein family, PAPD7. The two polymerases (PAPD5 and PAPD7) are cellular host factors required for the maturation of HBV mRNA and the release of hepatitis B surface antigen (HBsAg) by HBV infected cells, allowing the virus to replicate. Inhibitors of PAPD5 and PAPD7 have been shown to reduce HBsAg levels from the blood of HBV-infected individuals, which is a well-established prognostic factor of inhibition of viral replication and treatment response.

While dual inhibition of PAPD5 and PAPD7 contributes to the effective suppression of HBV replication, only inhibition of PAPD5 is required for the treatment of TBDs caused by TERC destabilization. Conversely, selective inhibition of PAPD5 over PAPD7 may be advantageous for a drug for the treatment of TBDs and poikiloderma with neutropenia.

The object of the present invention is to provide a new compound for the treatment and prevention of TBDs, poikiloderma with neutropenia and hepatitis B infection.

The problem is solved by a compound of formula (I). Further preferred embodiments are subject of the dependent claims.

It has been shown that a compound of formula (I) has inhibitory activity on PAPD5. Due to this inhibitory effect, the compounds according to the present invention inhibit TERC degradation and rescue TERC function. They also rescue hematopoiesis and prevent defects in blood cell production in patients with USB1 mutations. Furthermore, their dual inhibition of PAPD5 and PAPD7 allows an effective suppression of HBV replication. Therefore, the compound is useful as a therapeutically active substance in the treatment and/or prevention of a disease which benefits from PAPD5 inhibition selected from the group consisting of TBDs, poikiloderma with neutropenia and hepatitis B, i.e. as a medicament.

In particular, it was found that compounds of formula (I), as defined below in detail, are useful as medicaments for the treatment and prevention of TBDs and for the treatment and prevention of hepatitis B infections. Said compounds act as PAPD5 inhibitors.

It is another object of the invention to provide compounds with inhibitory activity on PAPD5 and PAPD7 for the treatment and prevention of hepatitis B infection.

It is a further object of the invention to provide inhibitors of PAPD5 with selectivity over PAPD7 for the treatment and prevention of diseases related to the shortening of telomeres and poikiloderma with neutropenia as its selectivity may afford a lower potential to cause unwanted off-target related side effects in these indications.

Thus, the present invention relates to a compound of formula (I)

I (I)

or a pharmaceutically acceptable salt, a racemic mixture, a corresponding enantiomer or, if applicable, a corresponding diastereomer thereof, wherein $R^1$ is selected from the group consisting of hydrogen, a linear or branched $C_1$ to $C_6$ alkyl, a $C_3$ to $C_5$ cycloalkyl, a $C_1$-$C_3$-alkyl-$C_3$-$C_5$-cycloalkyl, and a cyclic ether comprising 4 to 5 ring atoms,
  wherein said $C_1$ to $C_6$ linear or branched alkyl is optionally substituted with one or more substituents selected from the group consisting of fluoro, chloro, hydroxy and $C_1$ to $C_3$ alkoxy,
  wherein said $C_3$ to $C_5$ cycloalkyl and said $C_1$-$C_3$-alkyl-$C_3$-$C_5$-cycloalkyl may optionally be substituted with one or more substituents selected from the group consisting of fluoro, chloro, $C_1$ to $C_3$ alkyl, hydroxy and $C_1$ to $C_3$ alkoxy, and
  wherein said cyclic ether comprising 4 to 5 ring atoms is optionally substituted with one or more substituents selected from the group consisting of fluoro, chloro, $C_1$ to $C_3$ alkyl, hydroxy and $C_1$ to $C_3$ alkoxy;

$R^2$ is selected from the group consisting of hydrogen and methyl;

$R^3$ is selected from the group consisting of hydrogen, a linear or branched $C_1$ to $C_6$ alkyl, a $C_3$ to $C_6$ cycloalkyl, a 4 to 6 membered heterocycloalkyl, $C_1$-$C_3$-alkyl-$C_3$-$C_6$-cycloalkyl and a $C_1$-$C_3$-alkyl-4-6-membered heterocycloalkyl,
  wherein said linear or branched $C_1$ to $C_6$ alkyl may optionally be substituted with one or more substituents selected from the group consisting of fluoro, chloro, cyano, hydroxy and $C_1$ to $C_3$ alkoxy; and
  wherein said $C_3$ to $C_6$ cycloalkyl, said 4-6-membered heterocycloalkyl, said $C_1$-$C_3$-alkyl-$C_3$-$C_6$-cycloalkyl and said $C_1$-$C_3$-alkyl-4-6-membered heterocycloalkyl may optionally be substituted with one or more substituents selected from the group consisting of fluoro, chloro, cyano, $C_1$ to $C_3$ alkyl, hydroxy and $C_1$ to $C_3$ alkoxy; or $R^2$ and $R^3$ may form together a 4 to 6 membered monocyclic cycloalkyl or heterocycloalkyl, which may optionally be substituted with one or more substituents selected from the group consisting of fluoro, chloro, cyano, $C_1$ to $C_3$ alkyl, hydroxy and $C_1$ to $C_3$ alkoxy $R^4$ is selected from the group consisting of a linear or branched $C_1$ to $C_6$ alkoxy, an alkoxyalkoxyl group having up to 6 carbon atoms, a $C_1$-$C_3$ alkoxy $C_3$-$C_8$ cycloalkyl, a 4-7-membered heterocycloalkyl, a $C_{1-6}$ alkyl 4-7 membered monocyclic heterocycloalkyl, a $C_2$ to $C_8$ alkenyl and a $C_2$ to $C_8$ alkynyl and
  wherein said $C_1$ to $C_6$ alkoxy, said alkenyl and said alkynyl may optionally be substituted with one or more substituents selected from the group consisting of hydroxy, chloro and fluoro, a 3 to 6 membered monocyclic cycloalkyl group, a 4 to 6 membered monocyclic heterocycloalkyl group, a spirocyclic 3 to 7 membered monocyclic cycloalkyl group and a spirocyclic 3 to 7 membered monocyclic heterocycloalkyl group; and
  wherein said $C_1$-$C_3$ alkoxy $C_3$-$C_8$ cycloalkyl, said 4-7-membered heterocycloalkyl, and said $C_{1-6}$ alkyl 4-7 membered monocyclic heterocycloalkyl may optionally be substituted with one or more substituents selected from the group consisting of hydroxy, chloro, fluoro, and $C_1$ to $C_3$ alkyl and $C_1$ to $C_3$ alkoxy;

$R^5$ is selected from the group consisting of fluoro, chloro, bromo, cyano, $C_1$ to $C_5$ alkoxy, $C_1$ to $C_5$ alkyl, alkoxyalkyl having up to 6 carbon atoms, 4 to 6 membered heterocycloalkyl, 3 to 6 membered cycloalkyl, 5-membered heteroaryl, and $NR^6R^7$
  wherein said $C_1$ to $C_5$ alkoxy and said alkoxyalkyl having up to 6 carbon atoms may optionally be substituted with one or more substituents selected from the group consisting of fluoro, chloro, hydroxy, $C_1$ to $C_3$ alkoxy, and wherein said $C_1$ to $C_5$ alkyl is optionally substituted with one or more substituents selected from the group consisting of fluoro, chloro, $C_1$ to $C_3$ alkoxy, 3 to 6 membered cycloalkyl and 4 to 6 membered heterocycloalkyl, and wherein said 4 to 6 membered heterocycloalkyl is optionally substituted with one or more substituents selected from the group consisting of fluoro, chloro, hydroxy, $C_1$ to $C_3$ alkoxy, and $C_1$ to $C_3$ alkyl, wherein said 3 to 6 membered cycloalkyl is optionally substituted one or more substituents selected from the group consisting of with fluoro, chloro, hydroxy, $C_1$ to $C_3$ alkoxy, and $C_1$ to $C_3$ alkyl;

wherein $R^6$ and $R^7$ are independently selected from the group consisting of hydrogen, methyl and ethyl, and wherein said 5-membered heteroaryl is optionally substituted with one or more substituents selected from the group consisting of fluoro, chloro, hydroxy, $C_1$ to $C_3$ alkoxy, and $C_1$ to $C_3$ alkyl.

In the present specification and claims, the following terms apply:

The term "$C_1$ to $C_6$ linear or branched alkyl" means straight or branched chain alkyl groups having from 1 to 6 carbon atoms and includes, for example, methyl, ethyl, n-propyl, isopropyl, butyl, isobutyl, secondary butyl, tertiary butyl, n-pentyl, isopentyl, neopentyl, n-hexyl, 2-methylpentyl and the like.

The term "optionally substituted with one or more substituents" means that a further defined atom or group of atoms has replaced hydrogen as the "substituent" attached to another group. Examples of "a $C_1$ to $C_6$ linear or branched alkyl which is substituted with one or more substituents" are $—CH_2CH_2F$, $—CH_2CHF_2$, $—CH_2CH_2OH$, $—CH(OCH_3)CH_3$ and $—CH_2CH_2OCH_3$.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

The term "alkenyl" means a straight or branched hydrocarbon chain having one or more carbon-carbon double bonds, such as for example, ethene, propene, 1-butene, 2-butene, propadiene.

The term "alkynyl" means a straight of branched hydrocarbon chain having one or more carbon-carbon triple bonds, such as, for example, ethyne, propyne, butadiyne, 1,4-hexadiyne.

The term "alkoxy" means a radical $—OA^1$ where $A^1$ is an alkyl as defined herein. Examples of alkoxy groups are methoxy, ethoxy and propoxy.

The term "alkoxyalkyl" means a moiety of the formula $A^2-O-A^3-$ where $A^2$ is alkyl and $A^3$ is alkylene as defined herein. Exemplary alkoxyalkyl groups include methoxymethyl, 2-methoxyethyl, 3-methoxypropyl and 1-methyl-2-methoxyethyl.

The term "$C_3$ to $C_5$ cycloalkyl" refers to a saturated monovalent cyclic hydrocarbon radical of three to five ring carbons such as cyclopropyl, cyclobutyl and cyclopentyl. By analogy, the term "$C_3$ to $C_6$ cycloalkyl" denotes a saturated monovalent cyclic hydrocarbon radical with three to six ring atoms. A substituted cycloalkyl refers to a cycloalkyl group in which one or more hydrogen atoms attached to the ring have been replaced by other atoms or group of atoms. The substitutions can occur at any position on the cycloalkyl ring. If a hydrogen atom is replaced by a methyl group ($—CH_3$), it forms a methyl-substituted cycloalkyl group, such as methylcyclopropyl. Similarly, if a hydrogen atom is replaced by a fluorine atom ($—F$), it forms a fluoro-substituted cycloalkyl group.

The term "$C_1$-$C_3$-alkyl-$C_3$-$C_5$-cycloalkyl" means the group -$A^4$-$A^5$ where $A^5$ is a cycloalkyl group, and $A^4$ is a $C_1$ to $C_3$ alkylene group which is directly attached to the molecule scaffold of compound (I) consisting of the three rings. Examples include $—CH_2$-cyclopropyl and $—(CH_2)_2$-cyclopropyl. A substituted $C_1$-$C_3$-alkyl-$C_3$-$C_5$-cycloalkyl refers to a cycloalkyl group in which one or more hydrogen atoms attached to the ring have been replaced by other atoms or group of atoms. Examples include $—CH_2$-1-chlorocyclopropyl and $—(CH_2)_2$-1-fluorocyclopropyl.

The term "alkoxyalkoxyl" means a moiety of the formula $A^6$-O-$A^7$-O— where $A^6$ is alkyl and $A^7$ is alkylene as defined herein. Exemplary alkoxyalkoxyl groups include methoxyethoxy, ethoxyethoxy and propoxyethoxy. The term "cyclic ether" refers to a heterocyclic residue with an oxygen atom in a saturated or unsaturated hydrocarbon ring having 4 to 5 ring atoms. Examples are tetrahydrofuranyl, oxetanyl and furanyl. A substituted cyclic ether refers to a cyclic ether moiety in which one or more hydrogen atoms attached to the ring have been replaced by other atoms or group of atoms. The substitutions can occur at any position on the cycloalkyl ring. Examples are 2-fluorotetrahydrofuranyl and 3-chlorooxetane.

The term "$C_1$-$C_3$ alkoxy $C_3$-$C_8$ cycloalkyl" means the group -$A^8$-$A^9$ where $A^9$ is a cycloalkyl group, and $A^8$ is a $C_1$ to $C_3$ alkoxy group which is directly attached to the molecule scaffold of compound (I) consisting of the three rings. Examples include $—OCH_2$-cyclopropyl (i.e. cyclopropylmethoxy) and $—O—(CH_2)_2$-cyclopropyl (i.e. cyclopropylethoxy). A substituted $C_1$-$C_3$ alkoxy $C_3$-$C_8$ cycloalkyl refers to a cycloalkyl group in which one or more hydrogen atoms attached to the ring have been replaced by other atoms or group of atoms. Examples include $—O—CH_2$-1-chlorocyclopropyl and $—O—(CH_2)_2$-1-fluorocyclopropyl.

The term "4-to-6-membered heterocycloalkyl" or "4-to-7-membered heterocycloalkyl" means a stable cyclic group having carbon atoms and 1 to 3 heteroatoms independently selected from S, N or O, wherein when two O atoms or one O atom and one S atom are present, the two O atoms or one O atom and one S atom are not bonded to each other, respectively. Illustrative examples of 4- to 6-membered heterocycloalkyl moieties are cyclic ethers as defined above, thiophen-2-yl and piperidin-4-yl. A substituted 4- to 6-membered heterocycloalkyl refers to a 4- to 6-membered heterocycloalkyl moiety in which one or more hydrogen atoms attached to the ring have been replaced by other atoms or group of atoms. The substitutions can occur at any position on the ring. Examples are 2-fluorotetrahydrofuran-2-yl, 3-chlorothiophen-2-yl, 1-hydroxy-pyrrolidin-1-yl and 2-cyano-piperidin-4-yl.

The term "5-membered heteroaryl" means an aromatic heterocycle ring of 5 members, where at least one carbon atom of the ring is replaced with a heteroatom independently selected from nitrogen, oxygen, and sulfur. Illustrative examples of 5-membered heteroaryl moieties are pyrrolyl, furanyl, oxazolyl and thiazolyl. A substituted 5-membered heteroaryl refers to a 5-membered heteroaryl moiety in which one or more hydrogen atoms attached to the ring have been replaced by other atoms or group of atoms. The substitutions can occur at any position on the ring. An example is 3-chloro-1H-pyrrolyl.

The term "heteroatom" means nitrogen, oxygen or sulfur.

The term "enantiomers" means a pair of optical isomers that are non-superimposable mirror images of each other.

The term "diastereoisomers" means optical isomers which are not mirror images of each other.

The term "racemic mixture" means a mixture containing equal parts of individual enantiomers.

The compound according to the present invention may be in the form of a pharmaceutically acceptable salt. The terms "pharmaceutically acceptable salt" refers to salts prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

Within the context of the present invention the term PAPD5 related disease means diseases which benefit from PAPD5 inhibition, such as TBDs and poikiloderma with neutropenia, but also diseases such as hepatitis B which involve PAPD5 and PAPD7.

Surprisingly, it was found that the 9-oxo-9,10-dihydro-6H-pyrano[3,2-b:4,5-b']dipyridine scaffold of the compounds according to the present invention leads to very active compounds when compared with those of the state of the art. In particular, the combination of the presence of the nitrogen atom in the 1-position and the oxygen atom in the 5-position, and even more particularly the combination of these two structural features with an N-alkyl substituent in the 10-position of the scaffold seem to be crucial for the high activity.

In one embodiment of the present invention $R^1$ is selected from the group consisting of methyl, ethyl, 2,2-difluoroethyl and cyclopropyl, preferably ethyl, 2,2-difluoroethyl and cyclopropyl, most preferably cyclopropyl, and $R^2$, $R^3$, $R^4$ and $R^5$ are as defined above. Surprisingly, compounds of formula (I) wherein $R^1$ is methyl, ethyl, 2,2-difluoroethyl or cyclopropyl, and in particular cyclopropyl, are surprisingly even more active than those wherein $R^1$ is hydrogen.

In one embodiment of the present invention $R^2$ is hydrogen and $R^1$, $R^3$, $R^4$ and $R^5$ are as defined above.

In one embodiment of the present invention $R^3$ is selected from the group consisting of isopropyl, sec-butyl, (1-methyl) cyclopropyl and tert-butyl, preferably isopropyl and tert-butyl, and $R^1$, $R^2$, $R^4$ and $R^5$ are as defined above. Preferably, $R^3$ is selected from the group consisting isopropyl and tert-butyl, $R^1$ is selected from the group consisting of methyl, ethyl, 2,2-difluoroethyl and cyclopropyl, and $R^2$, $R^4$ and $R^5$ are as defined above.

In a further embodiment of the present invention $R^2$ and $R^3$ form together a 4 to 6 membered cycloalkyl or a 4 to 6 membered heterocycloalkyl, preferably a cyclopentyl ring and $R^1$, $R^4$ and $R^5$ are as defined above.

In one embodiment of the present invention $R^4$ is selected from the group consisting of cyclopropylmethoxy, 2-cyclopropylethoxy and —O(CH$_2$)$_3$OCH$_3$, preferably, —O(CH$_2$)$_3$OCH$_3$ and $R^1$, $R^2$, $R^3$ and $R^5$ are as defined above.

In one embodiment of the present invention $R^5$ is selected from the group consisting of methoxy, ethoxy, methyl, ethyl, methoxymethyl and cyclopropyl, preferably, methoxy and cyclopropyl and $R^1$, $R^2$, $R^3$ and $R^4$ are as defined above. Preferably, $R^5$ is selected from the group consisting methoxy and cyclopropyl, $R^1$ is selected from the group consisting of is methyl, ethyl, 2,2-difluoroethyl and cyclopropyl, and $R^2$, $R^3$ and $R^4$ are as defined above.

Preferably, the compounds of the present invention are selected from the group consisting of compounds 1 to 120 in Table 1 below:

| Compound | $R^1$ | $R^2$ | $R^3$ | $R^4$ | $R^5$ |
|---|---|---|---|---|---|
| 1 | H | H | isopropyl | cyclopropylmethoxy | methoxy |
| 2 | methyl | H | isopropyl | cyclopropylmethoxy | methoxy |
| 3 | ethyl | H | isopropyl | cyclopropylmethoxy | methoxy |
| 4 | cyclopropyl | H | isopropyl | cyclopropylmethoxy | methoxy |
| 5 | CH$_2$CHF$_2$ | H | isopropyl | cyclopropylmethoxy | methoxy |
| 6 | CH$_2$CH$_2$OH | H | isopropyl | cyclopropylmethoxy | methoxy |
| 7 | H | methyl | isopropyl | cyclopropylmethoxy | methoxy |
| 8 | methyl | methyl | isopropyl | cyclopropylmethoxy | methoxy |
| 9 | ethyl | methyl | isopropyl | cyclopropylmethoxy | methoxy |
| 10 | cyclopropyl | methyl | isopropyl | cyclopropylmethoxy | methoxy |
| 11 | CH$_2$CHF$_2$ | methyl | isopropyl | cyclopropylmethoxy | methoxy |
| 12 | CH$_2$CH$_2$OH | methyl | isopropyl | cyclopropylmethoxy | methoxy |
| 13 | H | H | t-butyl | cyclopropylmethoxy | methoxy |
| 14 | methyl | H | t-butyl | cyclopropylmethoxy | methoxy |
| 15 | ethyl | H | t-butyl | cyclopropylmethoxy | methoxy |
| 16 | cyclopropyl | H | t-butyl | cyclopropylmethoxy | methoxy |
| 17 | CH$_2$CHF$_2$ | H | t-butyl | cyclopropylmethoxy | methoxy |
| 18 | CH$_2$CH$_2$OH | H | t-butyl | cyclopropylmethoxy | methoxy |
| 19 | H | methyl | t-butyl | cyclopropylmethoxy | methoxy |
| 20 | methyl | methyl | t-butyl | cyclopropylmethoxy | methoxy |
| 21 | ethyl | methyl | t-butyl | cyclopropylmethoxy | methoxy |
| 22 | cyclopropyl | methyl | t-butyl | cyclopropylmethoxy | methoxy |
| 23 | CH$_2$CHF$_2$ | methyl | t-butyl | cyclopropylmethoxy | methoxy |
| 24 | CH$_2$CH$_2$OH | methyl | t-butyl | cyclopropylmethoxy | methoxy |
| 25 | H | H | isopropyl | O(CH$_2$)$_3$OCH$_3$ | methoxy |
| 26 | methyl | H | isopropyl | O(CH$_2$)$_3$OCH$_3$ | methoxy |
| 27 | ethyl | H | isopropyl | O(CH$_2$)$_3$OCH$_3$ | methoxy |
| 28 | cyclopropyl | H | isopropyl | O(CH$_2$)$_3$OCH$_3$ | methoxy |
| 29 | CH$_2$CHF$_2$ | H | isopropyl | O(CH$_2$)$_3$OCH$_3$ | methoxy |
| 30 | CH$_2$CH$_2$OH | H | isopropyl | O(CH$_2$)$_3$OCH$_3$ | methoxy |
| 31 | H | methyl | isopropyl | O(CH$_2$)$_3$OCH$_3$ | methoxy |
| 32 | methyl | methyl | isopropyl | O(CH$_2$)$_3$OCH$_3$ | methoxy |
| 33 | ethyl | methyl | isopropyl | O(CH$_2$)$_3$OCH$_3$ | methoxy |
| 34 | cyclopropyl | methyl | isopropyl | O(CH$_2$)$_3$OCH$_3$ | methoxy |

-continued

| Compound | R¹ | R² | R³ | R⁴ | R⁵ |
|---|---|---|---|---|---|
| 35 | CH₂CHF₂ | methyl | isopropyl | O(CH₂)₃OCH₃ | methoxy |
| 36 | CH₂CH₂OH | methyl | isopropyl | O(CH₂)₃OCH₃ | methoxy |
| 37 | H | H | t-butyl | O(CH₂)₃OCH₃ | methoxy |
| 38 | methyl | H | t-butyl | O(CH₂)₃OCH₃ | methoxy |
| 39 | ethyl | H | t-butyl | O(CH₂)₃OCH₃ | methoxy |
| 40 | cyclopropyl | H | t-butyl | O(CH₂)₃OCH₃ | methoxy |
| 41 | CH₂CHF₂ | H | t-butyl | O(CH₂)₃OCH₃ | methoxy |
| 42 | CH₂CH₂OH | H | t-butyl | O(CH₂)₃OCH₃ | methoxy |
| 43 | H | methyl | t-butyl | O(CH₂)₃OCH₃ | methoxy |
| 44 | methyl | methyl | t-butyl | O(CH₂)₃OCH₃ | methoxy |
| 45 | ethyl | methyl | t-butyl | O(CH₂)₃OCH₃ | methoxy |
| 46 | cyclopropyl | methyl | t-butyl | O(CH₂)₃OCH₃ | methoxy |
| 47 | CH₂CHF₂ | methyl | t-butyl | O(CH₂)₃OCH₃ | methoxy |
| 48 | CH₂CH₂OH | methyl | t-butyl | O(CH₂)₃OCH₃ | methoxy |
| 49 | H | H | isopropyl | cyclopropylmethoxy | cyclopropyl |
| 50 | methyl | H | isopropyl | cyclopropylmethoxy | cyclopropyl |
| 51 | ethyl | H | isopropyl | cyclopropylmethoxy | cyclopropyl |
| 52 | cyclopropyl | H | isopropyl | cyclopropylmethoxy | cyclopropyl |
| 53 | CH₂CHF₂ | H | isopropyl | cyclopropylmethoxy | cyclopropyl |
| 54 | CH₂CH₂OH | H | isopropyl | cyclopropylmethoxy | cyclopropyl |
| 55 | H | methyl | isopropyl | cyclopropylmethoxy | cyclopropyl |
| 56 | methyl | methyl | isopropyl | cyclopropylmethoxy | cyclopropyl |
| 57 | ethyl | methyl | isopropyl | cyclopropylmethoxy | cyclopropyl |
| 58 | cyclopropyl | methyl | isopropyl | cyclopropylmethoxy | cyclopropyl |
| 59 | CH₂CHF₂ | methyl | isopropyl | cyclopropylmethoxy | cyclopropyl |
| 60 | CH₂CH₂OH | methyl | isopropyl | cyclopropylmethoxy | cyclopropyl |
| 61 | H | H | t-butyl | cyclopropylmethoxy | cyclopropyl |
| 62 | methyl | H | t-butyl | cyclopropylmethoxy | cyclopropyl |
| 63 | ethyl | H | t-butyl | cyclopropylmethoxy | cyclopropyl |
| 64 | cyclopropyl | H | t-butyl | cyclopropylmethoxy | cyclopropyl |
| 65 | CH₂CHF₂ | H | t-butyl | cyclopropylmethoxy | cyclopropyl |
| 66 | CH₂CH₂OH | H | t-butyl | cyclopropylmethoxy | cyclopropyl |
| 67 | H | methyl | t-butyl | cyclopropylmethoxy | cyclopropyl |
| 68 | methyl | methyl | t-butyl | cyclopropylmethoxy | cyclopropyl |
| 69 | ethyl | methyl | t-butyl | cyclopropylmethoxy | cyclopropyl |
| 70 | cyclopropyl | methyl | t-butyl | cyclopropylmethoxy | cyclopropyl |
| 71 | CH₂CF₂ | methyl | It-butyl | cyclopropylmethoxy | cyclopropyl |
| 72 | CH₂CH₂OH | methyl | t-butyl | cyclopropylmethoxy | cyclopropyl |
| 73 | H | H | isopropyl | O(CH₂)₃OCH₃ | cyclopropyl |
| 74 | methyl | H | isopropyl | O(CH₂)₃OCH₃ | cyclopropyl |
| 75 | ethyl | H | isopropyl | O(CH₂)₃OCH₃ | cyclopropyl |
| 76 | cyclopropyl | H | isopropyl | O(CH₂)₃OCH₃ | cyclopropyl |
| 77 | CH₂CHF₂ | H | isopropyl | O(CH₂)₃OCH₃ | cyclopropyl |
| 78 | CH₂CH₂OH | H | isopropyl | O(CH₂)₃OCH₃ | cyclopropyl |
| 79 | H | methyl | isopropyl | O(CH₂)₃OCH₃ | cyclopropyl |
| 80 | methyl | methyl | isopropyl | O(CH₂)₃OCH₃ | cyclopropyl |
| 81 | ethyl | methyl | isopropyl | O(CH₂)₃OCH₃ | cyclopropyl |
| 82 | cyclopropyl | methyl | isopropyl | O(CH₂)₃OCH₃ | cyclopropyl |
| 83 | CH₂CHF₂ | methyl | isopropyl | O(CH₂)₃OCH₃ | cyclopropyl |
| 84 | CH₂CH₂OH | methyl | isopropyl | O(CH₂)₃OCH₃ | cyclopropyl |
| 85 | H | H | t-butyl | O(CH₂)₃OCH₃ | cyclopropyl |
| 86 | methyl | H | t-butyl | O(CH₂)₃OCH₃ | cyclopropyl |
| 87 | ethyl | H | t-butyl | O(CH₂)₃OCH₃ | cyclopropyl |
| 88 | cyclopropyl | H | t-butyl | O(CH₂)₃OCH₃ | cyclopropyl |
| 89 | CH₂CHF₂ | H | t-butyl | O(CH₂)₃OCH₃ | cyclopropyl |
| 90 | CH₂CH₂OH | H | t-butyl | O(CH₂)₃OCH₃ | cyclopropyl |
| 91 | H | methyl | t-butyl | O(CH₂)₃OCH₃ | cyclopropyl |
| 92 | methyl | methyl | t-butyl | O(CH₂)₃OCH₃ | cyclopropyl |
| 93 | ethyl | methyl | t-butyl | O(CH₂)₃OCH₃ | cyclopropyl |
| 94 | cyclopropyl | methyl | t-butyl | O(CH₂)₃OCH₃ | cyclopropyl |
| 95 | CH₂CHF₂ | methyl | t-butyl | O(CH₂)₃OCH₃ | cyclopropyl |
| 96 | CH₂CH₂OH | methyl | t-butyl | O(CH₂)₃OCH₃ | cyclopropyl |
| 97 | H | | cyclopentyl | cyclopropylmethoxy | methoxy |
| 98 | methyl | | cyclopentyl | cyclopropylmethoxy | methoxy |
| 99 | ethyl | | cyclopentyl | cyclopropylmethoxy | methoxy |
| 100 | cyclopropyl | | cyclopentyl | cyclopropylmethoxy | methoxy |
| 101 | CH₂CHF₂ | | cyclopentyl | cyclopropylmethoxy | methoxy |
| 102 | CH₂CH₂OH | | cyclopentyl | cyclopropylmethoxy | methoxy |
| 103 | H | | cyclopentyl | O(CH₂)₃OCH₃ | methoxy |
| 104 | methyl | | cyclopentyl | O(CH₂)₃OCH₃ | methoxy |
| 105 | ethyl | | cyclopentyl | O(CH₂)₃OCH₃ | methoxy |
| 106 | cyclopropyl | | cyclopentyl | O(CH₂)₃OCH₃ | methoxy |
| 107 | CH₂CHF₂ | | cyclopentyl | O(CH₂)₃OCH₃ | methoxy |
| 108 | CH₂CH₂OH | | cyclopentyl | O(CH₂)₃OCH₃ | methoxy |
| 109 | H | | cyclopentyl | cyclopropylmethoxy | cyclopropyl |
| 110 | methyl | | cyclopentyl | cyclopropylmethoxy | cyclopropyl |
| 111 | ethyl | | cyclopentyl | cyclopropylmethoxy | cyclopropyl |

-continued

| Compound | R¹ | R² | R³ | R⁴ | R⁵ |
|---|---|---|---|---|---|
| 112 | cyclopropyl | cyclopentyl | cyclopropylmethoxy | cyclopropyl | |
| 113 | $CH_2CF_2$ | cyclopentyl | cyclopropylmethoxy | cyclopropyl | |
| 114 | $CH_2CH_2OH$ | cyclopentyl | cyclopropylmethoxy | cyclopropyl | |
| 115 | H | cyclopentyl | cyclopropylmethoxy | cyclopropyl | |
| 116 | methyl | cyclopentyl | cyclopropylmethoxy | cyclopropyl | |
| 117 | ethyl | cyclopentyl | cyclopropylmethoxy | cyclopropyl | |
| 118 | cyclopropyl | cyclopentyl | cyclopropylmethoxy | cyclopropyl | |
| 119 | $CH_2CHF_2$ | cyclopentyl | cyclopropylmethoxy | cyclopropyl | |
| 120 | $CH_2CH_2OH$ | cyclopentyl | cyclopropylmethoxy | cyclopropyl | |

In one embodiment of the present invention R⁴ is selected from the group consisting of cyclopropylmethoxy, 2-cyclopropylethoxy and —O(CH₂)₃OCH₃, preferably, —O(CH₂)₃OCH₃, and R¹, R², R³ and R⁵ are as defined above.

In one embodiment of the present invention R⁵ is selected from the group consisting of methoxy, ethoxy, methyl, ethyl, methoxymethyl and cyclopropyl, and R¹, R², R³ and R⁴ are as defined above.

Good results could be obtained by compounds selected from the group of compounds 501 to 511:

| No. | Structure |
|---|---|
| 501 | |
| 502 | |
| 503 | |
| 504 | 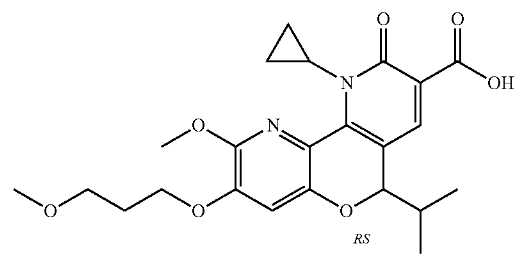 [SMILES: COCCCOc1cc2c(nc1OC)-c1c(cc(C(=O)O)c(=O)n1C1CC1)C(C(C)C)O2] |
| 505 | 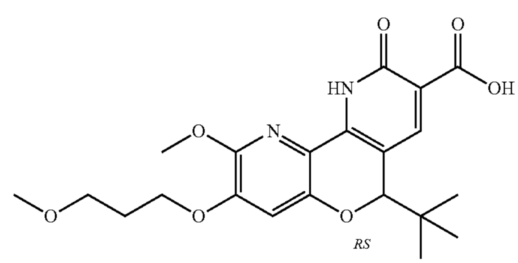 [SMILES: COCCCOc1cc2c(nc1OC)-c1[nH]c(=O)c(C(=O)O)cc1C(C(C)(C)C)O2] |
| 506 | 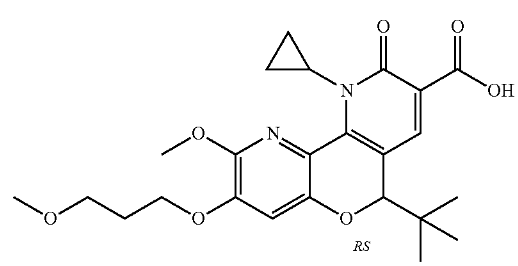 [SMILES: COCCCOc1cc2c(nc1OC)-c1c(cc(C(=O)O)c(=O)n1C1CC1)C(C(C)(C)C)O2] |
| 507 | 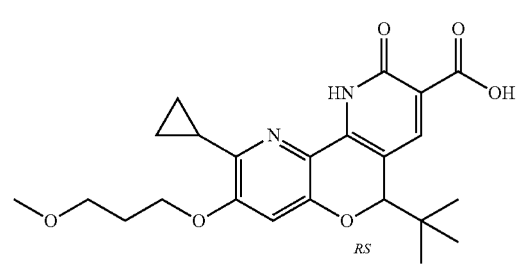 [SMILES: COCCCOc1cc2c(nc1C1CC1)-c1[nH]c(=O)c(C(=O)O)cc1C(C(C)(C)C)O2] |

13
-continued

| No. | Structure |
|---|---|
| 508 | 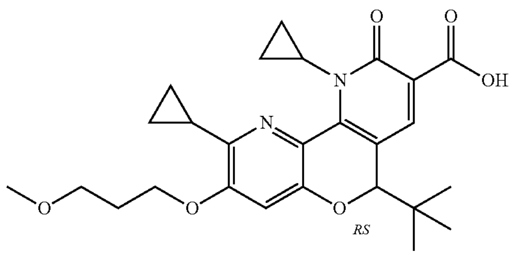 [SMILES: COCCCOc1cc2c(nc1C1CC1)-c1c(cc(C(=O)O)c(=O)n1C1CC1)C(C(C)(C)C)O2] |
| 509 | 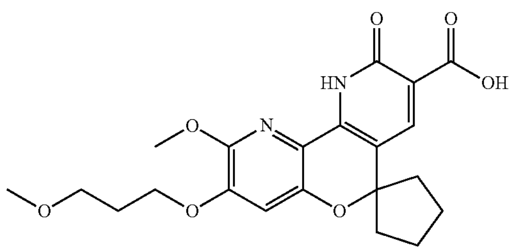 [SMILES: COCCCOc1cc2c(nc1OC)-c1[nH]c(=O)c(C(=O)O)cc1C1(CCCC1)O2] |
| 510 | 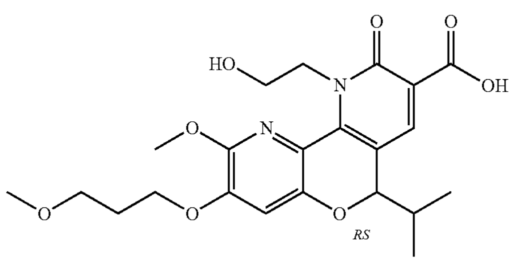 [SMILES: COCCCOc1cc2c(nc1OC)-c1c(cc(C(=O)O)c(=O)n1CCO)C(C(C)C)O2] |
| 511 | 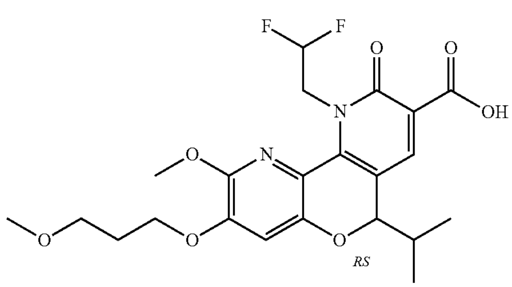 [SMILES: COCCCOc1cc2c(nc1OC)-c1c(cc(C(=O)O)c(=O)n1CC(F)F)C(C(C)C)O2] |

Especially good results could be obtained with (RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (RS)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid, in particular with (S)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (S)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid.

In a further embodiment, the present invention relates to the compounds according to the present invention for use as a medicament.

14

In a further embodiment, the present invention relates to a pharmaceutical composition comprising a pharmaceutically acceptable carrier and/or adjuvant; and a compound of the formula (I)

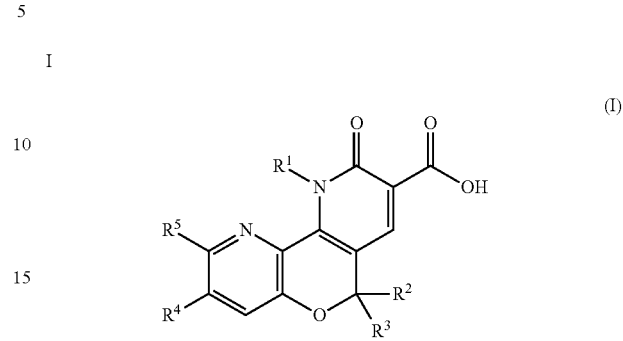

(I)

or a pharmaceutically acceptable salt, a racemic mixture, a corresponding enantiomer or, if applicable, a corresponding diastereomer thereof, wherein R is selected from the group consisting of hydrogen, a linear or branched $C_1$ to $C_6$ alkyl, a $C_3$ to $C_5$ cycloalkyl, a $C_1$-$C_3$-alkyl-$C_3$-$C_5$-cycloalkyl, and a cyclic ether comprising 4 to 5 ring atoms,
  wherein said $C_1$ to $C_6$ linear or branched alkyl is optionally substituted with one or more substituents selected from the group consisting of fluoro, chloro, hydroxy and $C_1$ to $C_3$ alkoxy,
  wherein said $C_3$ to $C_5$ cycloalkyl and said $C_1$-$C_3$-alkyl-$C_3$-$C_5$-cycloalkyl may optionally be substituted with one or more substituents selected from the group consisting of fluoro, chloro, $C_1$ to $C_3$ alkyl, hydroxy and $C_1$ to $C_3$ alkoxy, and
  wherein said cyclic ether comprising 4 to 5 ring atoms is optionally substituted with one or more substituents selected from the group consisting of fluoro, chloro, $C_1$ to $C_3$ alkyl, hydroxy and $C_1$ to $C_3$ alkoxy;

$R^2$ is selected from the group consisting of hydrogen and methyl;

$R^3$ is selected from the group consisting of hydrogen, a linear or branched $C_1$ to $C_6$ alkyl, a $C_3$ to $C_6$ cycloalkyl, a 4 to 6 membered heterocycloalkyl, $C_1$-$C_3$-alkyl-$C_3$-$C_6$-cycloalkyl and a $C_1$-$C_3$-alkyl-4-6-membered heterocycloalkyl,
  wherein said linear or branched $C_1$ to $C_6$ alkyl may optionally be substituted with one or more substituents selected from the group consisting of fluoro, chloro, cyano, hydroxy and $C_1$ to $C_3$ alkoxy; and
  wherein said $C_3$ to $C_6$ cycloalkyl, said 4-6-membered heterocycloalkyl, said $C_1$-$C_3$-alkyl-$C_3$-$C_6$-cycloalkyl and said $C_1$-$C_3$-alkyl-4-6-membered heterocycloalkyl may optionally be substituted with one or more substituents selected from the group consisting of fluoro, chloro, cyano, $C_1$ to $C_3$ alkyl, hydroxy and $C_1$ to $C_3$ alkoxy; or $R^2$ and $R^3$ may form together a 4 to 6 membered monocyclic cycloalkyl or heterocycloalkyl, which may optionally be substituted with one or more substituents selected from the group consisting of fluoro, chloro, cyano, $C_1$ to $C_3$ alkyl, hydroxy and $C_1$ to $C_3$ alkoxy $R^4$ is selected from the group consisting of a linear or branched $C_1$ to $C_6$ alkoxy, an alkoxyalkoxyl group having up to 6 carbon atoms, a $C_1$-$C_3$ alkoxy $C_3$-$C_8$ cycloalkyl, a 4-7-membered heterocycloalkyl, a $C_1$-$C_6$ alkyl 4-7 membered monocyclic heterocycloalkyl, a $C_2$ to $C_8$ alkenyl and a $C_2$ to $C_8$ alkynyl and wherein said $C_1$ to $C_6$ alkoxy, said alkenyl and said alkynyl may optionally be substituted with one or more substituents selected from the group consisting of hydroxy, chloro and fluoro, a 3 to 6 membered monocyclic cycloalkyl group, a 4 to 6 membered monocyclic heterocycloalkyl group, a spirocyclic 3 to 7 membered monocyclic cycloalkyl group and a spirocyclic 3 to 7 membered monocyclic heterocycloalkyl group; and wherein said $C_1$-$C_3$ alkoxy $C_3$-$C_8$ cycloalkyl, said 4-7-membered heterocycloalkyl, and said $C_1$-$C_6$ alkyl 4-7 membered monocyclic heterocycloalkyl may optionally be substituted with one or more substituents selected from the group consisting of hydroxy, chloro, fluoro, and $C_1$ to $C_3$ alkyl and $C_1$ to $C_3$ alkoxy;

$R^5$ is selected from the group consisting of fluoro, chloro, bromo, cyano, $C_1$ to $C_5$ alkoxy, $C_1$ to $C_5$ alkyl, alkoxyalkyl having up to 6 carbon atoms, 4 to 6 membered heterocycloalkyl, 3 to 6 membered cycloalkyl, 5-membered heteroaryl, and $NR^6R^7$ wherein said $C_1$ to $C_5$ alkoxy and said alkoxyalkyl having up to 6 carbon atoms may optionally be substituted with one or more substituents selected from the group consisting of fluoro, chloro, hydroxy, $C_1$ to $C_3$ alkoxy, and wherein said $C_1$ to $C_5$ alkyl is optionally substituted with one or more substituents selected from the group consisting of fluoro, chloro, $C_1$ to $C_3$ alkoxy, 3 to 6 membered cycloalkyl and 4 to 6 membered heterocycloalkyl, and wherein said 4 to 6 membered heterocycloalkyl is optionally substituted with one or more substituents selected from the group consisting of fluoro, chloro, hydroxy, $C_1$ to $C_3$ alkoxy, and $C_1$ to $C_3$ alkyl, wherein said 3 to 6 membered cycloalkyl is optionally substituted one or more substituents selected from the group consisting of with fluoro, chloro, hydroxy, $C_1$ to $C_3$ alkoxy, and $C_1$ to $C_3$ alkyl;

wherein $R^6$ and $R^7$ are independently selected from the group consisting of hydrogen, methyl and ethyl, and wherein said 5-membered heteroaryl is optionally substituted with one or more substituents selected from the group consisting of fluoro, chloro, hydroxy, $C_1$ to $C_3$ alkoxy, and $C_1$ to $C_3$ alkyl, as a therapeutically active substance.

The term "pharmaceutical composition" as used here means a composition that is suitable for administering to human patients for the treatment and/or prevention of diseases. Said pharmaceutical composition efficiently inhibits the PAPD5 activity in a patient.

The term "prevention" refers to the prevention or reduction of signs and symptoms associated with TBDs, poikiloderma with neutropenia and hepatitis B in subjects who are at risk for developing the disease. In these subjects a predisposing factor may be retained, but the signs and/or symptoms of the disease do not occur or take significantly longer to develop. Further, it also includes the prevention of a further deterioration of the symptoms once the disease has occurred. In that respect, prevention denotes a reduction in the likelihood (chance) of the development and/or progression of the signs and/or symptoms of the disease. Thus, prevention relates to prophylactically treating the disease in that manner (such that, in contrast, therapeutically treating the disease mainly applies after disease development).

In a preferred embodiment of the present invention, the pharmaceutical composition comprises a pharmaceutically acceptable carrier and/or adjuvant; and a compound of the formula (I) as defined above.

As already mentioned, it could be shown that due to their inhibitory effect on PAPD5, the compounds and compositions according to the present invention and the compositions according to the present invention can effectively reduce TERC levels and rescue the decrease in telomerase activity and loss of telomeres at chromosome ends. Thus, they are suitable in the treatment and/or prevention of TBDs and/or its clinical manifestations.

Clinical manifestations of TBDs arise when short telomeres trigger premature replicative senescence, responsible for the depletion of the stem cell population in tissues and organs with high proliferation rate and self-renewal potential, like the epithelium and the hematopoietic system. Indeed, the mucocutaneous triad, i.e., abnormal skin pigmentation, mucosal leukoplakia and nail dystrophy, is a prominent feature of dyskeratosis congenita but often manifests in other TBDs. As the disease advances, dyskeratosis congenita patients can develop aplastic anemia and bone marrow failure, which, in most dyskeratosis congenita cases, occurs before the age of 30 and represents the main cause of death. Moreover, dyskeratosis congenita-affected individuals are also at high risk of hematological malignancies and solid cancers (mainly epithelial cancers, such as head and neck squamous cell carcinoma, anorectal and skin cancers) due to increased genomic instability. About 20% of dyskeratosis congenita patients develop IPF, a chronic and progressive interstitial lung disease with fatal outcome. In some instances, IPF manifests itself only during adulthood (e.g., sporadic IPF or in first generation telomere biology disorder families). As described for other TBDs, the main molecular mechanism underlying IPF caused by mutations in telomerase-related genes, is a failure of the alveolar epithelial stem cell II (AEC II) population due to critically short telomeres. Loss of the stem cell population gives rise to abnormal pulmonary interstitial morphology characterized by diffuse deposition of fibrotic tissue and lung scarring.

Due to the compounds and compositions of the present invention, it is possible to inhibit degradation of TERC, to increase levels of mature TERC, to rescue TERC function and to restore telomerase activity. In particular the compounds and compositions of the present invention are useful for the treatment and/or prevention of TBDs selected from the group consisting of dyskeratosis congenita, IPF, liver cirrhosis, aplastic anemia, bone marrow failure syndrome, immunodeficiencies, neurodevelopmental disorders and growth retardation linked to TBDs, aging-related diseases and premature aging syndromes caused by telomere shortening and replicative senescence (chronic obstructive pulmonary disease, type II diabetes, atherosclerosis, osteoarthritis, osteoporosis, chronic kidney disease, Alzheimer's disease and reduced fertility), preferably dyskeratosis congenita, IPF and liver cirrhosis.

Preferably, dyskeratosis congenita is selected from the group consisting of Høyeraal-Hreidarsson syndrome, Revesz syndrome and Coats plus syndrome.

Compounds and compositions according to the present invention are also useful for the treatment and/or prevention of poikiloderma with neutropenia.

Compounds and compositions according to the present invention are also particularly useful in the treatment and/or prevention of hepatitis B.

The compound or the composition according to the present invention can be administered to a patient, either alone or in combination with one or more additional therapeutic agents.

The pharmaceutical composition according to the present invention may comprise one or more additional therapeutic agents.

Such pharmaceutical compositions are useful for administration to a subject. Pharmaceutical compositions and formulations include carriers or excipients for administration to a subject. As used herein the terms "pharmaceutically acceptable" and "physiologically acceptable" mean a biologically compatible formulation, gaseous, liquid, or solid, or mixture thereof, which is suitable for one or more routes of administration, in vivo delivery, or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules, and crystals. Supplementary active compounds (e.g., preservatives, antibacterial, antiviral, and antifungal agents) can also be incorporated into the compositions. The formulations may, for convenience, be prepared or provided as a unit dosage form. In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone. Supplementary active compounds (e.g., preservatives, antioxidants, antimicrobial agents including biocides and biostats such as antibacterial, antiviral, and antifungal agents) can also be incorporated into the compositions. Preservatives and other additives include, for example, antimicrobials, anti-oxidants, chelating agents, and inert gases (e.g., nitrogen). Pharmaceutical compositions may therefore include preservatives, antimicrobial agents, antioxidants, chelating agents, and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

Exemplary routes of administration of the compound according to the present invention is a dosage of the compound that is sufficient to achieve a desired therapeutic effect, such as can optionally be formulated include inhalation, respiration, intubation, oral (buccal, sublingual, mucosal), intrapulmonary, rectal, intradermal, topical, dermal, parenteral (e.g., subcutaneous, intramuscular, intravenous, intradermal, intratracheal and epidural), intranasal, intracavity, transdermal, iontophoretic.

Preferred routes are oral and intrapulmonary.

The compound of the invention can be administered prior to the onset of the condition to prevent its occurrence, immediately after the onset of the pathological condition, or during the occurrence of an acute or protracted condition.

The present invention also relates to a method of treating a disease which benefits from PAPD5 inhibition selected from the group consisting of TBDs poikiloderma with neutropenia and hepatitis B comprising administering a compound of formula (I) or a pharmaceutically acceptable salt, a racemic mixture, a corresponding enantiomer or, if applicable, a corresponding diastereomer thereof to a patient having said disease in an amount effective to treat the disease.

A further aspect of the present invention relates to the method for preparing a compound of formula (I):

In a certain embodiment, the compounds of formula (I) of the invention can be manufactured according to a process comprising the step of hydrolyzing a nitrile derivative of formula (II)

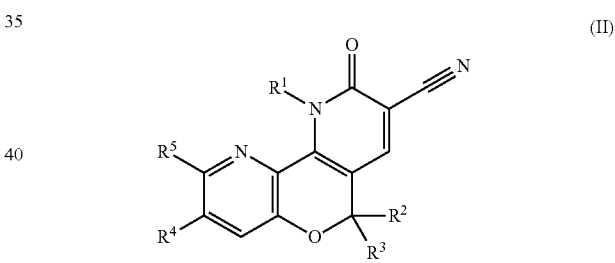

to obtain a compound of formula (I) wherein $R^1$, $R^2$, $R^3$, $R^4$ and $R^5$ are as defined hereinabove for formula (I).

The processes are described in more detail with the following general schemes and procedures I to VI.

Scheme I: General Scheme A

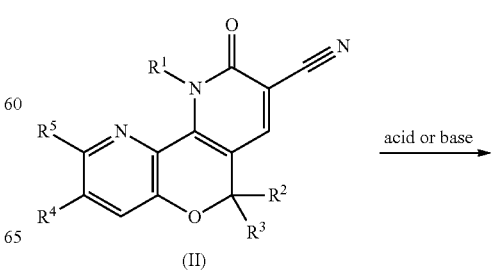

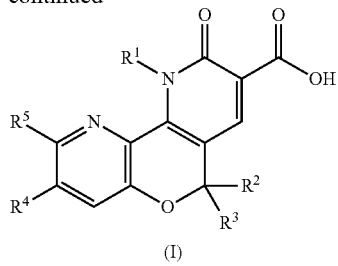

(I)

Compounds of formula (I) can be prepared by hydrolysis of a nitrile derivative of formula (II) according to methods known in the art, e.g. under basic conditions using a suitable base such as an aqueous solution of an inorganic hydroxide, bicarbonate or carbonate salt, or under acidic conditions using an aqueous solution of a suitable acid such as hydrochloric or sulfuric acid, optionally with a suitable organic co-solvent such as an alcohol, acetic acid, N,N-dimethylformamide, N-methylpyrrolidone, dimethyl sulfoxide or 1,4-dioxane at a temperature range between room temperature and reflux. General scheme A is hereinafter further illustrated with general procedure VII.

The synthesis of compounds of formula (II) is outlined in schemes I to VI hereinafter.

Scheme II: General Scheme B

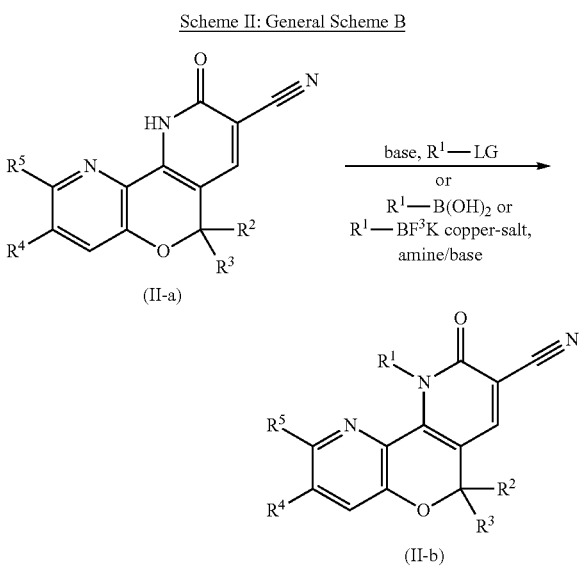

Compounds of formula (II-b) with $R^1$ different from H can be prepared from compounds of formula (II-a) (compounds of formula (II) wherein $R^1$ is H) according to methods known in the art, e.g. by treating a compound of formula (II-a) with a suitable base such as a carbonate salt or sodium hydride in a suitable temperature range, e.g. 0° C. to room temperature, followed by addition of an electrophilic reactant $R^1$-LG (wherein LG is a leaving group, e.g. halogen or sulfonyl), which is either commercially available or easily prepared according to methods and starting materials well known in the art, in a suitable solvent such as N,N-dimethylformamide or a solvent mixture such as water/alcohol (e.g. methanol, ethanol, isopropanol or tert-butanol) or water/N,N-dimethylformamide. Alternatively, compounds of formula II-b can be prepared by reacting a compound of formula II-a with a boronic acid or a trifluoroborate salt ($R^1$-$BF_3$M, wherein M is an alkali metal such as K) in the presence of a copper salt such as copper(II) acetate or bromide and typically an aromatic or aliphatic mono- or bidentate amine such as phenanthroline, 2,2'-bipyridine, pyridine, triethylamine or N,N,N,N-tetramethylethylenediamine, optionally in the presence of a base such as an alkali metal salt of carbonate or a bis(trialkylsilyl)amide, in a suitable solvent or solvent mixture selected from water, an alcohol (e.g. methanol, ethanol, isopropanol or tert-butanol), acetonitrile, 1,4-dioxane, tetrahydrofuran, dichloromethane, dichloroethane, toluene, N,N-dimethylformamide, N-methylpyrrolidone or dimethyl sulfoxide at a suitable temperature between room temperature and reflux. General scheme B is hereinafter further illustrated with general procedures V and VI.

Scheme III: General Scheme C

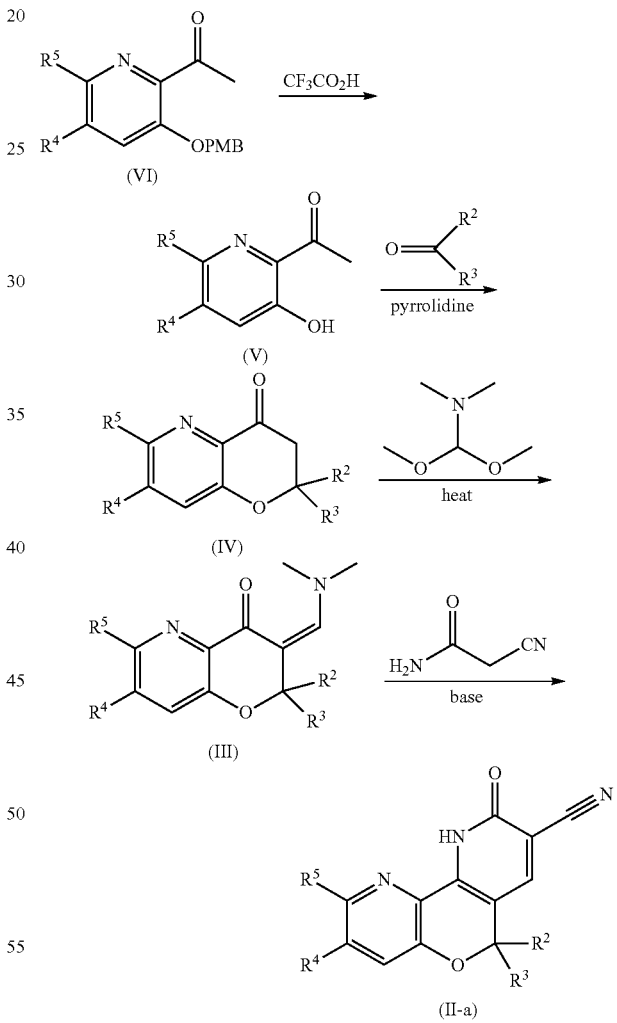

Intermediates of formula (II-a) can be prepared by cyclocondensation of a compound of formula (III) with cyanoacetamide in the presence of a suitable base such as sodium hydride or the alkali metal salt of an alcoholate such as sodium or potassium methoxide, ethoxide, isopropoxide or tert-butoxide in a suitable solvent such as an alcohol (e.g. methanol, ethanol, isopropanol or tert-butanol) or N,N-dimethylformamide at a suitable temperature between room temperature and reflux. Compounds of formula (III) can be prepared by condensation of compounds of formula (IV) with N,N-dimethylformamide dimethyl acetal at 100-120° C. Compounds of formula (IV) can be prepared by cyclocondensation of compounds of formula (V) with aldehydes or ketones of formula $R^2$—(C=O)—$R^3$, which is either commercially available or easily prepared according to methods and starting materials well known in the art, in the presence of a suitable secondary amine such as pyrrolidine in a suitable solvent such as an alcohol (e.g. methanol, ethanol, isopropanol or tert-butanol) at a suitable temperature between room temperature and 100° C. Compounds of formula (V) can be obtained by O-deprotection of para-methoxybenzyl intermediates of formula (VI) by treatment with excess trifluoroacetic acid in dichloromethane at room temperature. General scheme C is hereinafter further illustrated with general procedures I to IV.

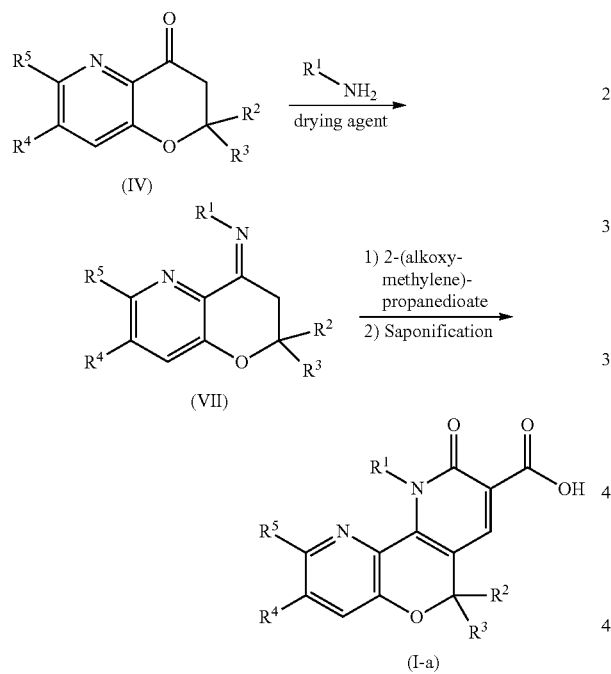

solvent such as dichloromethane, dichloroethane, benzene, toluene or an ether such as tetrahydrofuran at a temperature between room temperature and reflux.

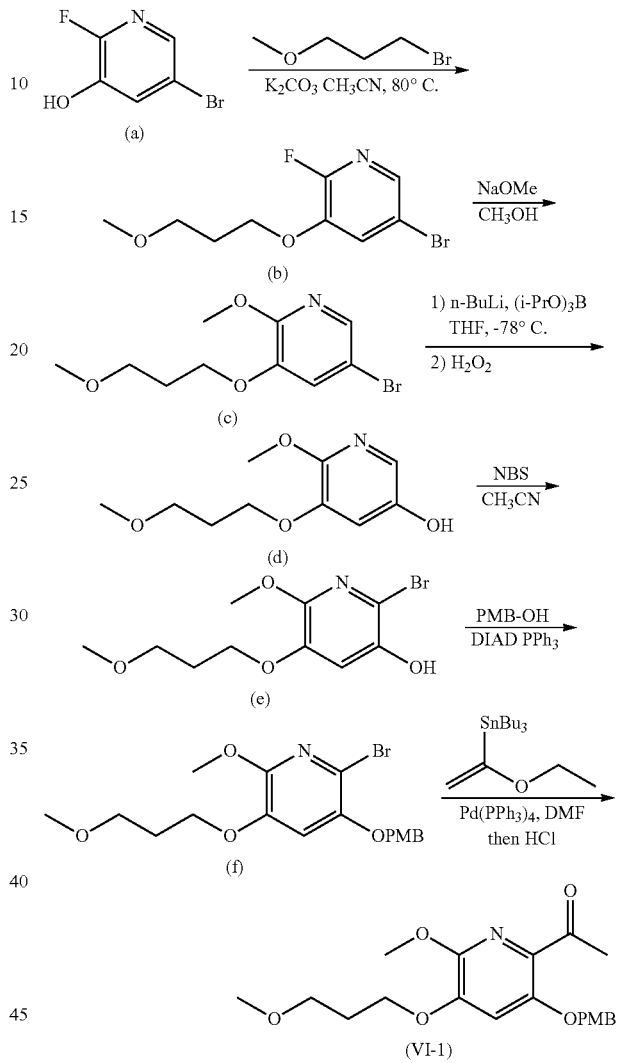

Alternatively to the procedures described in general schemes A-C, compounds of formula (I-a), wherein $R^1$ is alkyl, can be prepared from imines of formula (VII) by cyclocondensation with a 2-(alkoxymethylene)propanedioated such as dimethyl methoxymethylenemalonate, diethyl ethoxymethylenemalonate or 5-(methoxymethylene)-2,2-dimethyl-1,3-dioxane-4,6-dione in a suitable solvent such as dimethylsulfoxide, sulfolane, diphenyl ether or diglyme at a temperature between room temperature and 240° C. followed by saponification using methods known in the art, such as a mixture of aqueous sodium hydroxide solution and an organic solvent such as tetrahydrofuran, 1,4-dioxane or ethanol at a temperature between room temperature and reflux. Imine intermediates of formula (VII) can be prepared from a ketone of formula (IV) and a primary amine of formula $R^1$—$NH_2$ either using a large excess of the amine to drive the equilibrium to the side of the imine or using a drying agent such as activated molecular sieves, titanium (IV) isopropoxide or titanium(IV) chloride in a suitable Intermediate (VI-1), a compound of formula (VI) wherein $R^4$ is methoxypropoxy and $R^5$ is methoxy, can be prepared as follows: 5-Bromo-2-fluoropyridin-3-ol (a) is O-alkylated using 1-bromo-3-methoxypropane in the presence of dipotassium carbonate in acetonitrile at 80° C. to give 5-bromo-2-fluoro-3-(3-methoxypropoxy)pyridine (b), which is subsequently converted to 5-bromo-2-methoxy-3-(3-methoxypropoxy)pyridine (c) using sodium methoxide in methanol at room temperature. Subsequent treatment of compound (c) with triisopropyl borate and n-buthyllithium at −78° C. followed by oxidation with hydrogen peroxide gives rise to 6-methoxy-5-(3-methoxypropoxy)pyridin-3-ol (d), which can be brominated using N-bromosuccinimide at room temperature to give compound (e). Protection of the latter using para-methoxybenzyl alcohol under Mitsunobu conditions and palladium catalyzed cross-coupling of the resulting compound (f) with tributyl(1-ethoxyethenyl)stannane gives intermediate (VI-1).

Scheme VI: Preparation of intermediates (VI-2) and (VI-3)

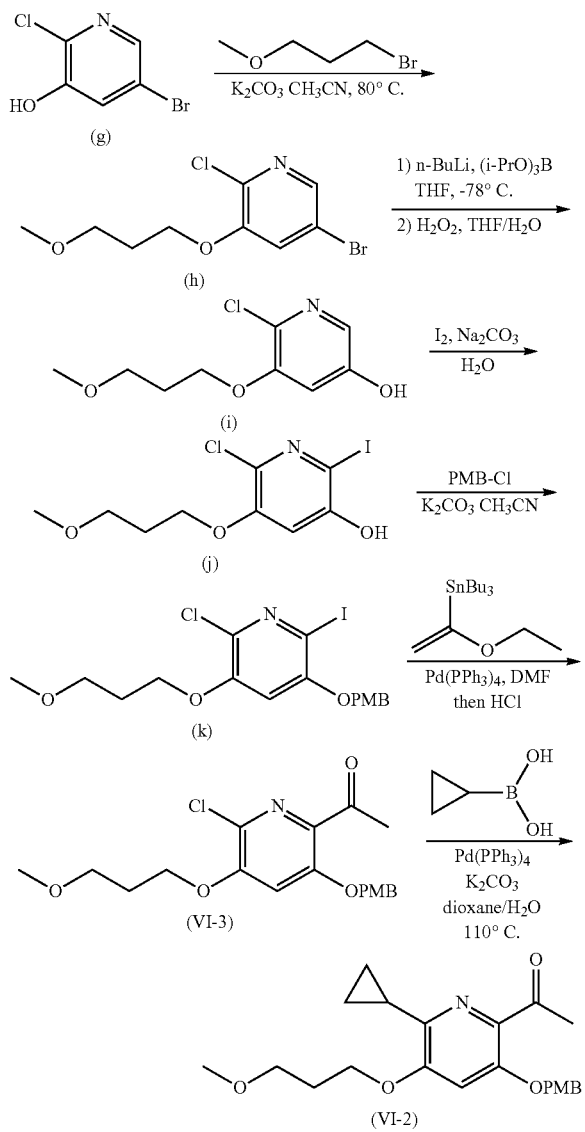

Intermediate (VI-2), a compound of formula (VI) wherein $R^4$ is methoxypropoxy and $R^5$ is cylcopropyl, can be prepared as follows: 5-Bromo-2-chloropyridin-3-ol (g) is O-alkylated using 1-bromo-3-methoxypropane in the presence of dipotassium carbonate in acetonitrile at 80° C. to give 5-bromo-2-methoxy-3-(3-methoxypropoxy)pyridine (h), which is further converted to 6-chloro-5-(3-methoxypropoxy)pyridin-3-ol (i) by treatment with triisopropyl borate and n-buthyllithium at −78° C. followed by oxidation with hydrogen peroxide. Treatment of intermediate (i) with iodine in aqueous disodium carbonate solution at room temperature to give compound (j) followed by 0-protection with para-methoxybenzyl chloride using dipotassium carbonate in acetonitrile gives rise to compound (k), which can be further transformed to intermediate (VI-3), a compound of formula (VI) wherein $R^4$ is methoxypropoxy and $R^5$ is chloro, by palladium catalyzed cross-coupling of the resulting compound with tributyl(1-ethoxyethenyl)stannane.

Compound (VI-3) can be converted to intermediate (VI-2) by a Suzuki reaction using cyclopropyl boronic acid.

DESCRIPTION OF THE FIGURES

FIG. 2A: Agarose gel electrophoresis of TERC amplicons after 1-week treatment with different concentrations of Example 506. Patient-derived iPSCs show accumulation of the extended and unstable form of TERC. Inhibition of PAPD5 in patient-derived iPSCs with PAPD5 inhibitors Example 506, RG7834 and GST-HG131 restores the steady-state and physiological levels of the mature and stable form of TERC.

FIG. 2B: Telomere restriction fragment analysis (TRF) after 4-week treatment with increasing concentrations of PAPD5 inhibitors Example 506, RG7834 and GST-HG131. Inhibition of PAPD5 in patient-derived iPSCs dose-dependently effects telomere elongation to an average telomere length which is typical of that in healthy individuals in the relevant age-group.

EXPERIMENTAL PART

Figures 1A, 1B, 1C:
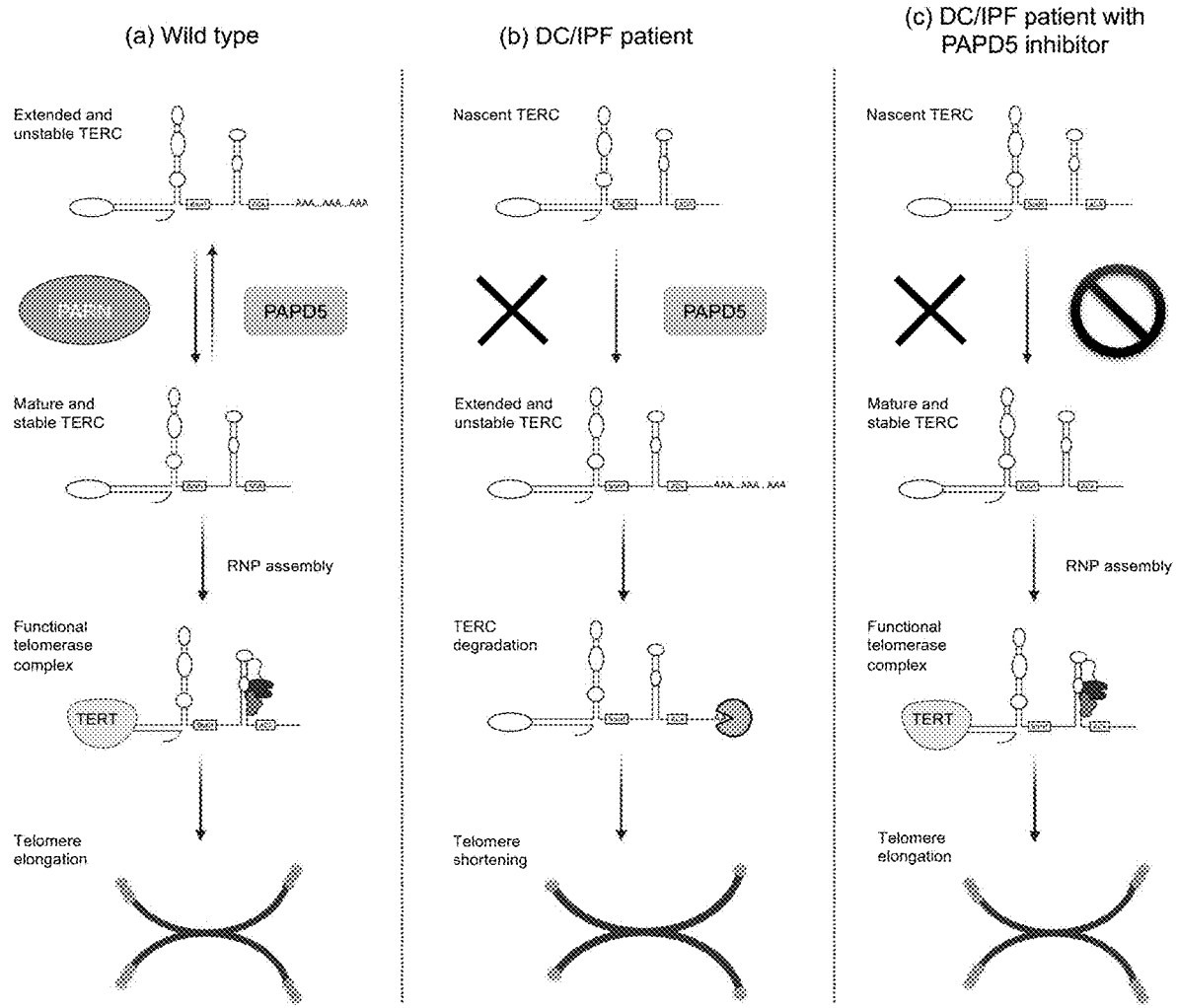
FIG. 1a: Processing of the RNA telomerase component TERC in healthy individuals: In healthy subjects PARN counteracts PAPD5 activity, promoting the accumulation of the mature and stable form of TERC and the assembly of a functional telomerase ribonucleoprotein (RNP) complex, which catalyzes telomere elongation.
FIG. 1b: Processing of the RNA telomerase component TERC in in TBD patients, e.g. with DC or IPF, without treatment: In patients carrying mutations in PARN, TERC precursors are polyadenylated by PAPD5 and targeted for degradation hindering the assembly of a functional RNP telomerase complex and resulting in telomere shortening. For simplicity, only PARN mutations are represented in FIG. 1b. However, mutations in TERC-, TCAB-, NAF1-, ZCCHC8- and RNP- encoding genes also jeopardize TERC stability and the assembly of the telomerase RNP complex leading to telomere shortening.
FIG. 1c: Processing of the RNA telomerase component TERC to restore telomere length: Patients with mutated PARN, TERC, TCAB, NAF1, ZCCHC8 and RNP factors can be treated with PAPD5 inhibitors to restore the levels of mature TERC to a physiological and healthy condition and facilitate the assembly of a functional telomerase RNP complex and consequently, telomere elongation.

Preferred compounds of the invention are shown in the examples. Particularly preferred are (RS)-6-isopropyl-2-methoxy-3-(3-methoxypropoxy)-9-oxo-9,10-dihydro-6H-pyrano[3,2-b:4,5-b']dipyridine-8-carboxylic acid (Example 501; which corresponds to compound 25 in Table 1)

(RS)-6-isopropyl-2-methoxy-3-(3-methoxypropoxy)-10-methyl-9-oxo-9,10-dihydro-6H-pyrano[3,2-b:4,5-b']dipyridine-8-carboxylic acid (Example 502; which corresponds to compound 26 in Table 1) (RS)-10-ethyl-6-isopropyl-2-methoxy-3-(3-methoxypropoxy)-9-oxo-9,10-dihydro-6H-pyrano[3,2-b:4,5-b']dipyridine-8-carboxylic acid (Example 503; which corresponds to compound 27 in Table 1)

(RS)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid (Example 504; which corresponds to compound 28 in Table 1)

(RS)-6-(tert-butyl)-2-methoxy-3-(3-methoxypropoxy)-9-oxo-9,10-dihydro-6H-pyrano[3,2-b:4,5-b']dipyridine-8-carboxylic acid (Example 505; which corresponds to compound 37 in Table 1)

(RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid (Example 506; which corresponds to compound 40 in Table 1)

(RS)-6-(tert-butyl)-2-cyclopropyl-3-(3-methoxypropoxy)-9-oxo-9,10-dihydro-6H-pyrano[3,2-b:4,5-b']dipyridine-8-carboxylic acid (Example 507; which corresponds to compound 85 in Table 1)

(RS)-6-(tert-butyl)-2,10-dicyclopropyl-3-(3-methoxypropoxy)-9-oxo-9,10-dihydro-6H-pyrano[3,2-b:4,5-b']dipyridine-8-carboxylic acid (Example 508; which corresponds to compound 88 in Table 1)

2'-methoxy-3'-(3-methoxypropoxy)-9'-oxo-9',10'-dihydrospiro[cyclopentane-1,6'-pyrano[3,2-b:4,5-b']dipyridine]-8'-carboxylic acid (Example 509)

(RS)-10-(2-hydroxyethyl)-6-isopropyl-2-methoxy-3-(3-methoxypropoxy)-9-oxo-9,10-dihydro-6H-pyrano[3,2-b:4,5-b']dipyridine-8-carboxylic acid (Example 510; which corresponds to compound 30 in Table 1)

(RS)-10-(2,2-difluoroethyl)-6-isopropyl-2-methoxy-3-(3-methoxypropoxy)-9-oxo-9,10-dihydro-6H-pyrano[3,2-b:4,5-b']dipyridine-8-carboxylic acid (Example 511; which corresponds to compound 29 in Table 1)

Pharmacological Tests

The compounds of the present invention exhibit inhibitory activity of PAPD5 and PAPD7. Compounds with selectivity for PAPD5 over PADP7 may be used preferably for the treatment of TBDs, poikiloderma with neutropenia and age-related diseases while compounds with similar potency on PAPD5 and PAPD7 have a higher potential to effectively suppress replication of HBV. The biological activities of the compounds of the present invention may be detected as described below.

Cell Culture Conditions:

The hepatocarcinoma HepG2/2.2.15 cell line (hereafter referred to as wild type) was obtained from Millipore (SCC249) and HepG2/2.2.15 PAPD5 knock-out (PAPD5 KO) and PAPD7 knock-out (PAPD7 KO) cells were generated using CRISPR/Cas9 technology. All HepG2/2.2.15 cell lines were maintained in DMEM/F12 (Thermo Scientific, 11320033) complemented with 10% Fetal Bovine Serum (FBS) (Merck, F7524) and 1% Penn/Strep (Fisher Scientific, 15-140-163) in 5% $CO_2$ at 37° C.

Healthy donor- and patient-derived induced Pluripotent Stem Cells (iPSCs), described in Moon et al. 2015, were cultured in feeder-free condition using Matrigel hESC-qualified matrix (Corning, 354277) coated cell culture dishes. For coating, one aliquot of Corning Matrigel hESC-qualified matrix (approximately 300 µL) was thawed on ice and diluted in 25 mL ice-cold DMEM/F-12. The aliquot volume is lot-specific and is reported on the product specification sheet accompanying the vial. The coating solution was kept on ice and Matrigel was handled using ice-cold pipette tips. 6 mL of the coating solution were added to one 10 cm cell culture dish and spread by gentle rocking. The coated dishes were then incubated at RT for at least 30 min to let the matrix solidify. The coating solution was aspirated from the dishes and cells were seeded immediately. Alternatively, the coated dishes were stored at 4° C. for max 1 week, and the coating solution was aspirated just before using the dishes. iPSCs were maintained in Essential E8 medium (Thermo Scientific, A1517001) complemented with 12 mL of provided E8 supplement and 10 µM Y-27632 (Abcam, AB120129) in 5% $CO_2$ at 37° C. Medium was replaced every day (10 mL/10 cm dish) and iPSCs were subcultured twice per week at a split ratio between 1:3 and 1:9, which was adjusted depending on the cell growth. To passage iPSCs, medium was aspirated and cells were washed once with 1× Phosphate-buffered saline (PBS) (Gibco, 14190-144) before adding Accutase (STEMCELL Technologies, 07922) (4 mL/10 cm dish). Cells were incubated shortly at 37° C. and the colonies were briefly disaggregated by gentle pipetting or by agitation. The single cell suspension was transferred in a canonical tube with cold 1× PBS and centrifuged at 300 g for 5 min to remove Accutase. Cell pellet was resuspended in an appropriate volume of complemented Essential E8 medium and seeded in a Matrigel-coated dish according to the split ratio.

Enzyme-linked immunosorbent assay (ELISA) for detection of Hepatitis B surface antigen:

An ELISA was performed using a hepatocarcinoma HepG2/2.2.15 wild type (WT) cell line to assess the potential of the compounds of the present invention as treatments of chronic HBV infection.

As described above, selective inhibition of PAPD5 may be an advantage for the treatment of TBDs. To this end, all compounds of the present invention were also tested in an ELISA on HepG2/2.2.15 PAPD5 and PAPD7 KO cell lines to determine the compounds' potency to inhibit PAPD5 and their selectivity for PAPD5 over PAPD7. The assay was performed as described below.

Cell seeding and addition of the compounds: On day −1, HepG2/2.2.15 cell lines were seeded in U-bottom 96-well plates (Fisher Scientific, 10777241) at a density of 1,5×10$^4$ cells/well in a final volume of 200 µL complemented DMEM/F12. On day 0, medium was aspirated and cells were washed once with PBS (300 µL/well). Then, PBS was replaced with complemented DMEM/F12 (200 µL/well). Using a Tecan-TE300e chemical dispenser, the compounds were added to the cells with 11 half-log incremental dilutions in dimethyl sulfoxide (DMSO) (Sigma-Aldrich, 276855) within the highest concentration equal to 25 µM (concentration range 1). DMSO was used as no-drug control, and the final DMSO concentration in all wells was 0.5%. The cells were then incubated with the compounds for 4 days in 5% $CO_2$ at 37° C. On day 4, the 96-well plate was centrifuged for 5 min at 300 g to spin down cell debris. 100 µL/well of cell culture supernatant were collected and diluted 1:2 with 100 µL of complemented DMEM/F12 to perform the ELISA. For the most potent compounds the assay was repeated using a lower concentration range (concentration range 2, 3 or 4 with 11 half-log incremental dilutions) to determine IC50 with better accuracy.

TABLE 1

Concentration ranges used to determine IC50 values in the ELISA assay.

| Concentration range 1 (nM) DMSO only | Concentration range 2 (nM) DMSO only | Concentration range 3 (nM) DMSO only | Concentration range 4 (nM) DMSO only |
|---|---|---|---|
| 0.251808 | 0.02014462 | 0.002014 | 0.000705 |
| 0.795713 | 0.06365701 | 0.006366 | 0.002228 |
| 2.514452 | 0.20115616 | 0.020116 | 0.00704 |
| 7.945668 | 0.63565346 | 0.063565 | 0.022248 |
| 25.10831 | 2.00866494 | 0.200866 | 0.070303 |
| 79.34227 | 6.34738122 | 0.634738 | 0.222158 |
| 250.7216 | 20.0577247 | 2.005772 | 0.70202 |
| 792.2801 | 63.3824099 | 6.338241 | 2.218384 |
| 2503.605 | 200.288415 | 20.02884 | 7.010095 |
| 7911.392 | 632.911392 | 63.29114 | 22.1519 |
| 25000 | 2000 | 200 | 70 |

ELISA: Before starting, the "Hepatitis B surface antigen ELISA kit" (Abnova, KA0286) was equilibrated at room temperature (RT) for 1 h. 50 μL of 1:2 diluted supernatant were mixed with 50 μL anti-HBs peroxidase solution in a microtiter plate coated with mouse monoclonal antibodies specific for HBsAg (hereafter referred to as anti-HB plate). The anti-HB plate was sealed using adhesive foil provided with the kit and incubated for 1 h at 37° C. After incubation, the supernatant-enzyme mixture was discarded, and the anti-HB plate was washed 8 times with 1× washing buffer (250 μL/well). After the last wash, the residual liquid was removed by turning the plate upside down and tapping on adsorbent paper. TMB substrate solutions A and B were mixed in equal volumes and 100 μL/well of this mixture were added to each well. The plate was covered with the supplied tray and incubated at RT for 20 min. During this time, a color develops in proportion to the amount of HBsAg bound to anti-HBs. After incubation, the reaction was stopped by adding 100 μL/well of 2N aqueous $H_2SO_4$ solution. The optical density of the developed color was read at 450 nm using a Cytation 5 instrument with reference wavelength at 620 nm.

CCK8 viability assay: Viability of HepG2/2.2.15 WT, PAPD5 KO and PAPD7 KO cell lines treated with the compounds was determined using the Cell Counting Kit-8 (CCK8, Sigma-Aldrich, 96992) following the manufacturer's instructions. Briefly, after collecting 100 μL of cell culture supernatant used for the ELISA, 10 μL/well of tetrazolium salt WST-8 reagent were added to the compound-treated cells, mixed well and incubated in 5% $CO_2$ at 37° C. for 1 h. During this time, WST-8 is reduced by dehydrogenases in cells to give a yellow-colored product (formazan), which is soluble in the tissue culture medium. The amount of the formazan dye generated by the activity of dehydrogenases in cells is directly proportional to the number of living cells. After 1 h incubation, the optical density of the developed color was read at 450 nm using a Cytation 5 instrument with the reference wavelength at 620 nm. CCK8 optical density values were used for normalization of the ELISA results.

Determination of IC50: The IC50 values for the combined effect of PAPD5 and PAPD7 inhibition in WT cells (Table 2) and for PAPD5 inhibition in PAPD7 KO cells and for PAPD7 inhibition in PAPD5 KO cells (Table 3) are defined as the compound concentration at which HBsAg secretion is reduced by 50% compared to the DMSO-treated control. To determine the IC50 values, the amount of HBsAg (optical density values of the ELISA) was corrected by the number of living cells (CCK8 optical density) per each well. Normalized HBsAg values were used to generate a dose-response curve with a non-linear regression model and applying the Levenberg-Marquardt algorithm. The percentage of inhibition was calculated relative to the untreated condition (DMSO CTRLs).

Results of the assay:

TABLE 2 pIC50 values of selected examples in HepG2/2.2.15 WT cells demonstrating their potential as therapeutics for the treatment and prevention of hepatitis B virus infection.

| Ex. # | pIC50 WT | Ex. # | pIC50 WT | Ex. # | pIC50 WT | Ex. # | pIC50 WT |
|---|---|---|---|---|---|---|---|
| 501 | 8.1 | 504 | 9.3 | 507 | 9.1 | 510 | 7.8 |
| 502 | 8.2 | 505 | 8.7 | 508 | 10.2 | 511 | 8.9 |
| 503 | 8.9 | 506 | 9.7 | 509 | 7.6 | | |

TABLE 3 pIC50 values of selected examples in HepG2/2.2.15 PAPD7 KO cells for PAPD5 inhibitory activity and in PAPD5 KO cells for PAPD7 inhibitory activity, and selectivity values for PAPD5 over PAPD7.

| Ex. | pIC50 PAPD5 (PAPD7 KO cells) | pIC50 PAPD7 (PAPD5 KO cells) | Fold sel. for PAPD5 over PAPD7 | Ex. # | pIC50 PAPD5 (PAPD7 KO cells) | pIC50 PAPD7 (PAPD5 KO cells) | Fold sel. for PAPD5 over PAPD7 |
|---|---|---|---|---|---|---|---|
| 501 | 8.2 | 7.4 | 7.1 | 507 | 9.4 | 9.2 | 1.8 |
| 502 | 8.5 | 7.9 | 4.2 | 508 | 10.0 | 10.0 | 1.0 |
| 503 | 9.0 | 8.3 | 5.9 | 509 | 7.5 | 6.5 | 10.4 |
| 504 | 9.2 | 8.6 | 4.8 | 510 | 8.3 | 7.5 | 6.4 |
| 505 | 8.7 | 8.0 | 4.9 | 511 | 9.1 | 8.3 | 6.9 |
| 506 | 10.1 | 9.3 | 6.1 | | | | |

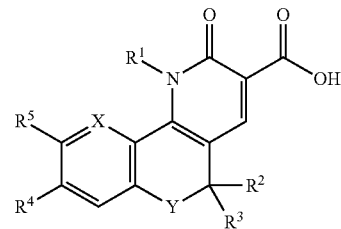

(I) X=N, Y=O (present invention)
(XX) X=N, Y=$CH_2$ (state of the art)
(XXI) X=CH, Y=$CH_2$ (state of the art)
(XXII) X=CH, Y=O (state of the art)

Compounds of formula (XX) and (XXI) were described in WO2019177937. As opposed to the 9-oxo-9,10-dihydro-6H-pyrano[3,2-b:4,5-b']dipyridine derivatives of formula (I) of the present invention, compounds of formula (XX) have a methylene group in the position of the oxygen atom in the pyrano-ring (5-position) of compounds of formula (I). Compounds of formula (XXI) differ from compounds of formula (I) in two positions: replacement of the oxygen atom in the pyrano-ring (5-position) by methylene and replacement of the ring-nitrogen atom in the 1-position by CH. In WO2019177937 only few derivatives of compounds of formula (XX) and (XXI) were described where $R^1$ is alkyl (Table 4). In all cases these derivatives are reported to be much less active than their N-unsubstituted analogs ($R^1$=H). This is also confirmed for the pair of comparative examples of formula XX, example 701 ($R^1$=H, example 46 of WO2019177937) and 702 ($R^1$=cyclopropyl, not exemplified in WO2019177937) (Table 5). In contrast, compounds of formula (I) of the present invention where $R^1$=alkyl are surprisingly more active than those where $R^1$=H. Comparative example 701 is more active than example 505 of the present invention. However, due to its higher polarity (logD(pH 7.4) of 1.1 vs. 1.4) example 505 is 2.6-fold more soluble than example 701 in a kinetic solubility assay at pH 6.5 (484.5 vs. 185.5 μM), which may translate in a higher oral bioavailability and generally better developability.

TABLE 4

Examples and example numbers from WO2019177937; EC50 values defined as effective concentrations that achieved 50% inhibitory effect.

| Formula | Ex. # | $R^1$ | $R^2$ | $R^3$ | $R^4$ | $R^5$ | EC50 HBsAg (μM) |
|---|---|---|---|---|---|---|---|
| XXI | 1 | H | H | isopropyl | $O(CH_2)_3OCH_3$ | OMe | 0.023 |
| XXI | 4 | methyl | H | isopropyl | $O(CH_2)_3OCH_3$ | OMe | 12 |
| XXI | 5 | benzyl | H | isopropyl | $O(CH_2)_3OCH_3$ | OMe | 15 |
| XX | 24 | H | H | isopropyl | $O(CH_2)_3OCH_3$ | Cl | 0.003 |
| XX | 25 | methyl | H | isopropyl | $O(CH_2)_3OCH_3$ | Cl | 0.094 |

WO2019110352 describes compounds of formula (XXII), in which the ring-nitrogen in position 1 of the 9-oxo-9,10-dihydro-6H-pyrano[3,2-b:4,5-b']dipyridine scaffold of compounds of formula (I) of the present invention is replaced by CH. Only derivatives of formula (XXII) where $R^1$ is a 3- or 4-membered cycloalkyl group but none with $R^1$=H have been reported. Surprisingly, as shown in Table 5, examples 505 and 506 of the present invention are considerably more active than the corresponding comparative examples 801 and 802, which were not exemplified in WO2019110352.

TABLE 5

Potencies of examples 505 and 506 in WT cells and on PAPD5 (determined in PAPD7 KO cells) in comparison to Comparative examples 701, 702, 801 and 802.

| | | | | |
|---|---|---|---|---|
| (I) | X = N, Y = O | | | (present invention) |
| (XX) | X = N, Y = $CH_2$ | | | (state of the art) |
| (XXII) | X = CH, Y = O | | | (state of the art) |

| Formula | Ex. # | $R^1$ | PIC50 WT | PIC50 PAPD5 (PAPD7 KO cells) |
|---|---|---|---|---|
| I | 505 | H | 8.7 | 8.7 |
| XX | 701 | H | 9.2 | 9.2 |
| XXII | 801 | H | 7.4 | 7.3 |
| I | 506 | cyclopropyl | 9.7 | 10.1 |
| XX | 702 | cyclopropyl | 8.6 | 8.5 |
| XXII | 802 | cyclopropyl | 9.0 | 9.0 |

Stabilization of TERC and re-elongation of telomeres in patient-derived iPSCs:

Purpose: As described above PAPD5 inhibition was shown to promote the accumulation of the mature and stable form of TERC, which rescues telomerase complex formation and drives telomere elongation and restoration.

Using cellular assays performed on patient-derived iPSCs with critically short telomeres (average length around 4 kb), we have demonstrated that potent inhibitors of PAPD5 can (1) restore levels of the stable form of TERC and (2) consequently promote telomere elongation. In these assays we have included, as a positive control, heathy donor-derived iPSCs which were obtained from a newborn and therefore display extremely long telomeres with an average length of 21 kb. The patient-derived iPSCs are instead obtained from a 24-year-old man who was diagnosed with DC at the age of 18. For reference, the average telomere length of healthy individuals in the same age-group (20-25 years old) is between 8 and 10 kb.

(1) To demonstrate the effect of PAPD5 inhibition on TERC RNA levels and processing we run a RLM-RACE experiment to visualize the stable (mature) and the unstable (extended) forms of TERC and determine the stability of the mature TERC RNA. The purpose of this assay is to evaluate the levels of the stable and mature forms of TERC, which is required for the formation of the telomerase holoenzyme, over the unstable TERC form.

(2) In addition, to prove the effect of potent PAPD5 inhibitors on telomere elongation, we have carried out a telomere elongation assay using telomere restriction fragment analysis. The scope of this assay is to isolate telomeric DNA from healthy donor- and patient-derived iPSCs and determine the average length of isolated telomeres.

In the assays using iPSCs we tested Example 506 and two potent PAPD5/7 inhibitors, GST-HG131 (preparation described in WO2021027566) and RG7834 (preparation described in WO2015113990), which were developed for the treatment of chronic HBV infection. The degree of PAPD5 engagement at the concentrations used for each compound (Table 6) was calculated from PAPD5 IC50 values determined by the ELISA using a HepG2/2.2.15 PAPD7 KO cell line as described above after correction for plasma protein binding (Table 7). In the ELISA 10% plasma protein (p=0.1) is used, whereas the assays using iPSCs are run in a plasma protein-free medium.

The unbound IC50 values in such a protein-free medium, $IC50_u$ (Table 8), are calculated as follows from the IC50 values in the ELISA ($IC50_{ELISA}$):

$$IC50_u = IC50_{ELISA} * \text{fraction unbound (ELISA)}$$
$$= IC50_{ELISA} * f_{u,ELISA} f_{u,ELISA} = 1/(p*((1/f_{u,plasma})-1)+1)$$

The degree of PAPD5 target engagement in percent (X) is calculated as follows:

$$X = 100 * \text{test concentration}/IC50_u/(1+\text{test concentration}/IC50_u)$$

The compounds were dissolved in DMSO at a 10 mM stock concentration and diluted in complemented Essential E8 medium at the reported concentrations (Table 6). For untreated samples (0 nM) DMSO only was added to the medium. Culture medium with the diluted compound was replaced daily, and cells were subcultured as described above.

TABLE 6

Concentrations of compounds tested in iPSCs.

| | Test concentrations (nM) | |
|---|---|---|
| Compound | Healthy donor-derived iPSCs | Patient-derived iPSCs |
| Example 506 | 0, 2.5 | 0, 0.1, 0.5, 2.5 |
| RG7834 | 0, 30 | 0, 0.3, 1, 3, 10, 30 |
| GST-HG131 | 0, 30 | 0, 0.3, 1, 3, 10, 30 |

TABLE 7

% Target engagement at test concentrations in assays using iPSCs.

| Compound | Test conc. (nM) | % Target engagement (X) |
|---|---|---|
| Example 506 | 0.1 | 54 |
| | 0.5 | 86 |
| | 2.5 | 97 |
| RG7834 | 0.3 | 16 |
| | 1 | 38 |
| | 3 | 65 |
| | 10 | 86 |
| | 30 | 95 |
| GST-HG131 | 0.3 | 4 |
| | 1 | 12 |
| | 3 | 29 |
| | 10 | 57 |
| | 30 | 80 |

TABLE 8

$IC50_u$ calculated from $IC50_{ELISA}$ and $f_{u, plasma}$

| Compound | $IC50_{ELISA}$ (nM) | $f_{u, plasma}$ | p | $f_{u, ELISA}$ | $IC50_u$ (nM) |
|---|---|---|---|---|---|
| Ex. 506 | 0.0847 | 0.347 | 0.1 | 0.84 | 0.07 |
| RG7834 | 1.637 | 0.328 | 0.1 | 0.83 | 1.35 |
| GST-HG131 | 7.417 | 0.43 | 0.1 | 0.88 | 6.55 |

To carry out the cellular assays, cells were cultured in the presence of PAPD5 inhibitors and collected at different time points. (1) At week 1 (Day 7), cells were harvested for RNA isolation to perform a RLM-RACE experiment. (2) At week 4 (Day 28), cells were harvested for DNA isolation to perform Telomere Restriction Fragment (TRF) analysis.

(1) Evaluation of TERC Stability Using RNA Ligation-Mediated Rapid Amplification of cDNA Ends (RLM-RACE)

Figure 2A:
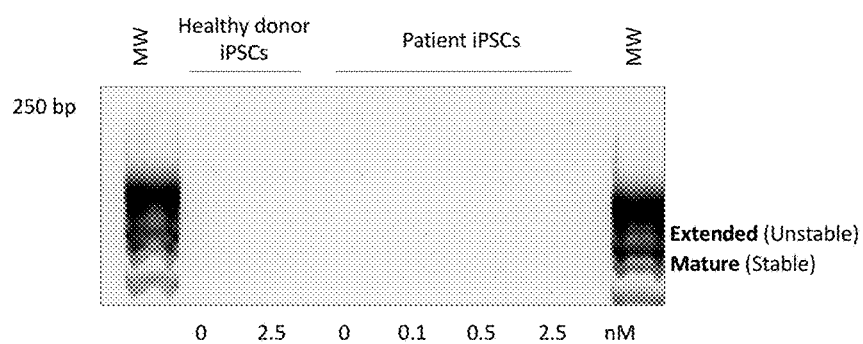
FIGS. 2A and 2B show that treatment of patient-derived induced pluripotent stem cells (iPSCs) with PAPD5 inhibitors rescues TERC levels and restores telomere length.
Figure 2A:
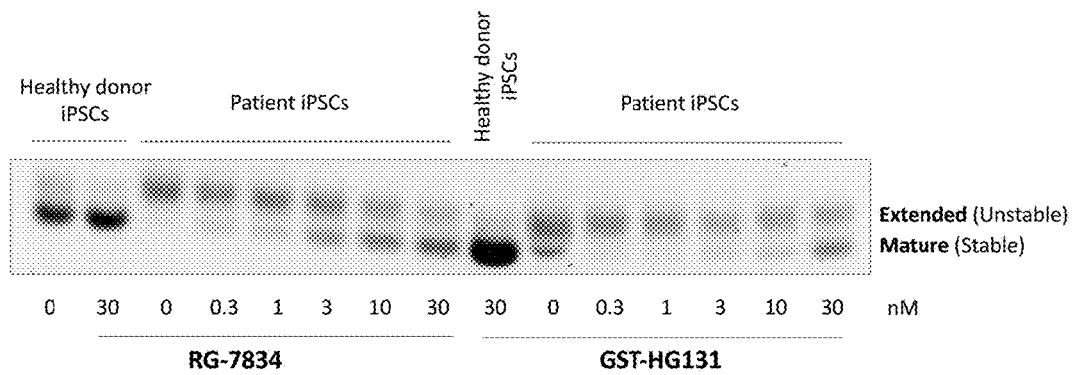

To assess the ability of PAPD5 inhibitors to restore TERC steady-state levels, iPSCs were harvested after 7 days of treatment with the compounds at the indicated concentrations to perform total RNA isolation followed by a RLM-RACE assay (FIG. 2A). The methods of the RLM-RACE assay are described below.

RLM-RACE:

Total RNA extraction: At day 7 of exposure, 1 million iPSCs per condition were resuspended in 350 µL of Trizol (Thermo Fisher, 15596026) and incubated for 5 min at RT. 70 µL of chloroform (Sigma Aldrich, 25668) were added per sample and tubes were shaken vigorously for 30 seconds. Samples were spun at 12000 g for 10 min at 4° C. The aqueous upper phase containing the RNA (about 150 µL) was carefully collected and transferred into a clean 1.5-mL Eppendorf tube, mixed with 175 µL of isopropanol and incubated for 10 min on ice. For RNA precipitation, samples were centrifuged at 12000 g for 10 min at 4° C. The supernatant was removed. As a further purification step 350 µL of 75% ethanol (Sigma Aldrich, 51976) was added to the RNA pellet. After centrifugation (12000 g for 10 min at 4° C.) to recover the RNA pellet the supernatant was aspirated carefully, and the RNA pellet was air-dried for few minutes before resuspending it in 30 µL of RNase-free ddH₂O. The RNA concentration was measured using a Qubit HS RNA quantification kit (Thermo Fisher, Q32852).

Linker ligation: Total RNA (500 ng) was ligated to 5 µM of 5'-adenylated, 3'-blocked adaptor (Universal miRNA Cloning Linker, New England BioLabs, S1315S) with 280 units of T4 RNA ligase, Truncated KQ (New England BioLabs, M0373L), 25% PEG 8000 and 1 µl of RNaseOUT (Thermo Fisher, 10777019) in a 20 µl reaction at 25° C. for 16 h.

The reaction volume was adjusted to 50 µl with RNase-free water before starting the cleanup procedure with RNA Clean and Concentrator columns (Zymo Research, R1016) following the instruction provided by the manufacturer. Ligated RNA was eluted in 13 µl RNase-free water.

For cDNA synthesis 11 µl of ligated RNA were mixed with 5 pmol of universal linker R primer (5'-CTACGTAAC-GATTGATGGTGCCTACAG-3') and 1 µl of 10 mM dNTPs (Thermo Fisher, 18427013). The mixture was incubated at 65° C. for 5 min to disrupt RNA secondary structures followed by 1 min incubation at 4° C.

First strand cDNA synthesis: Next, 200 U SuperScript III reverse transcriptase (Thermo Scientific, 18080044), 1 µl RNAseOUT, 1 µl 0.1 mM DTT and 4 µl 5× First-strand buffer were combined with the ligated RNA in a final volume of 20 µl per sample. First-strand cDNA synthesis was performed as follows: 5 min at 25° C., 60 min at 50° C., 10 min at 85° C., then 4° C.

PCR amplification of cDNA: For 2-step PCR amplification, 1.5 µl of first-strand cDNA template (from the previous step) were combined with 10 µl of 2× SsoAdvanced Universal SYBR Green Supermix (Bio-Rad, 1725271), 2 µl of 5 µM universal linker R primer (5'-CTACGTAACGATT-GATGGTGCCTACAG-3'), 2 µl of 5 µM TERC F primer (5'-CTCTGTCAGCCGCGGGTCTCTC-3') and 4.5 µl of RNase-free water in a final volume of 20 µl per sample. Thermal cycler parameters are reported in Table 9.

TABLE 9

Thermal cycler parameters for PCR amplification.

| Cycles | Temperature | Time |
|---|---|---|
| 1× | 98° C. | 2' |
| 40× | 98° C. | 5" |
| | 68° C. | 30" |
| | 4° C. | hold |

DNA was stored overnight at −20° C. before loading on agarose gel. PCR products were quantified using a Qubit dsDNA BR quantification kit (Thermo Fisher, Q32850). 300 ng of cDNA were mixed with Gel Loading purple 6× (NEB, B7024S) and directly analyzed on a 2.75% agarose (Sigma-Aldrich, A9539) gel with SYBER™ Safe DNA Gel Stain (10000×, Thermo Fisher, S33102) to visualize mature and extended TERC transcripts. The gel was run at 3 V/cm for about 4 hours and visualized using iBright 1500 Imaging system (Thermo Fisher).

Results of the assay: In untreated patient-derived iPSCs the unstable and extended form of TERC (FIG. 2A upper band) undergoes degradation upon processing by PAPD5 and cannot be converted into the stable and mature form of TERC (FIG. 2A lower band). By performing the TERC stability assay we have shown that PAPD5 inhibitors dose-dependently enhance the TERC maturation process leading to increased levels of the mature form of TERC in patient-derived iPSCs after 1 week of exposure. Steady-state and physiological levels of the mature and stable form of TERC are restored at concentrations at a PAPD5 engagement of 80% and above with all three compounds tested (FIG. 2A, Table 7). In healthy donor-derived iPSCs the PAPD5 inhibitors tested further augmented the levels of the mature form of TERC (FIG. 2A).

Figure 2B:
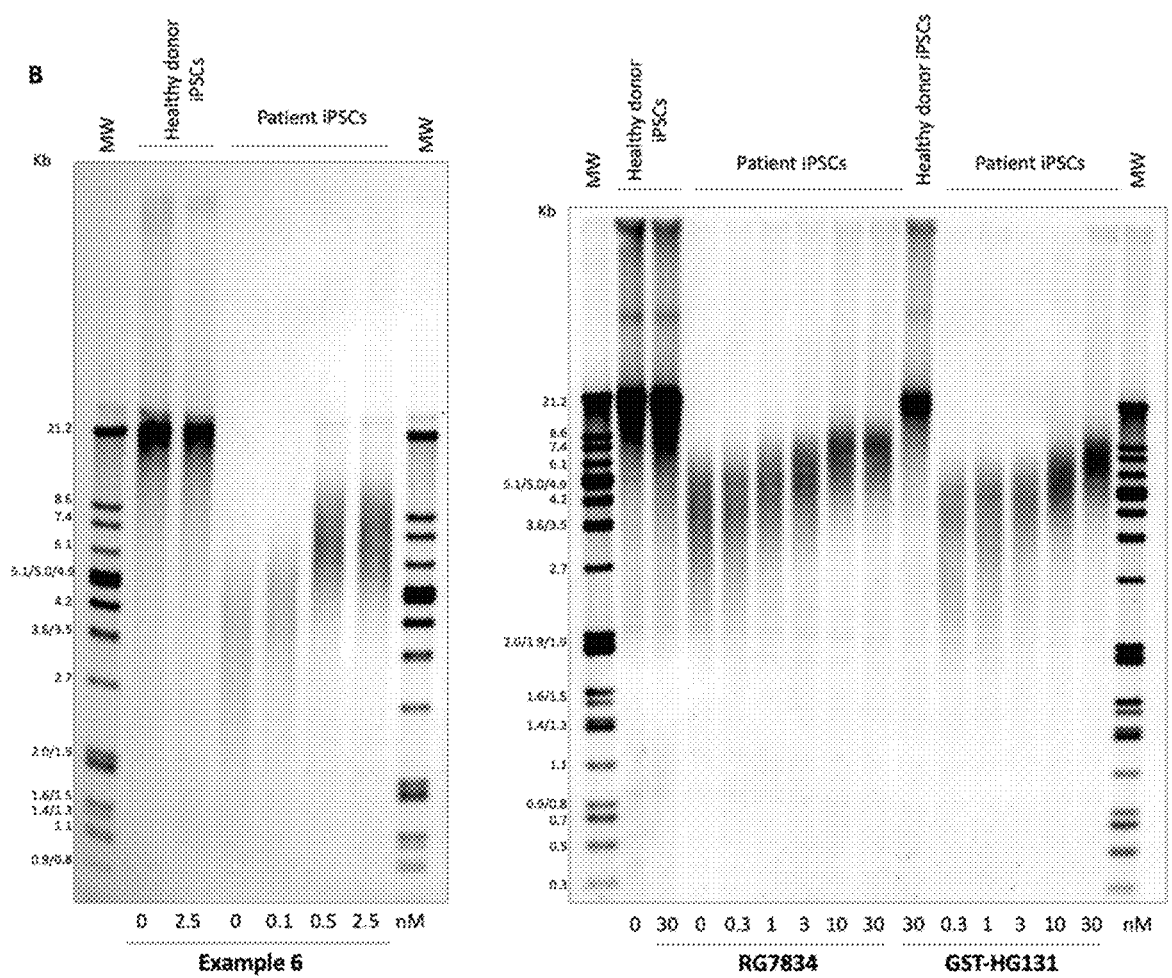

(2) Evaluation of Telomere Elongation Using Telomere Restriction Fragment (TRF) Analysis Elongation of telomeres was assessed by dose-dependently exposing iPSCs to PAPD5 inhibitors for 4 weeks. At week 4 (day 28 of exposure) iPSCs were collected to perform DNA isolation and telomere restriction fragment analysis (FIG. 2B). TRF analysis was performed as described below.

TRF analysis:

Genomic DNA extraction: At day 28 of exposure, 2×10$^6$ iPSCs per condition were pelleted and resuspended in 200 µl PBS. DNA was isolated using GeneJet Genomic DNA Purification Kit (Thermo Fisher, K0722) following instructions from the manufacturer. DNA was consecutively eluted with two 60-µl portions of elution buffer (final volume 120 µl/sample). DNA quantification was performed using a Qubit dsDNA BR quantification kit.

TRF assay: TRF analysis was performed per protocol using TeloTAGGG™ Telomere Length Assay kit (Roche, 12209136001). All the reagents described below are supplied with the kit unless otherwise specified. Incubation and washing steps of the blotting membrane were performed with gentle rotation in a hybridization oven according to the reported temperature and time.

1 µg of genomic DNA isolated from iPSCs was diluted in 17 µl of RNase-free water and digested with 0.5 µl of Hinfl and 0.5 µl of RsaI restriction enzymes (20 U/µl for each enzyme) in the presence of 2 µl of 20× Digestion buffer. Digestion was carried out over night at 37° C. in a final volume of 20 µl per sample. The reaction was stopped by adding 5× Loading buffer (5 µl/sample).

To visualize telomeric and sub-telomeric DNA, equal amounts of digested genomic DNA mixed with 5× Loading buffer were loaded in 0.8% agarose (Sigma-Aldrich, A9539) gel with SYBER™ Safe DNA Gel Stain (10000×, Thermo Fisher, S33102). 4 µl of DIG-labeled molecular weight marker were used as reference. The gel was run at 6V/cm in 1× TAE buffer for about 4 hours. At the end of the run, the gel was submerged in 0.25 M aqueous HCl solution with gentle agitation for 5 min at RT, rinsed 2× with autoclaved ddH$_2$O and soaked in Denaturation Solution (0.5 M NaOH, 1.5 M NaCl) for 2× 15 min at RT with gentle agitation. Again, the gel was rinsed 2× with autoclaved ddH$_2$O and submerged in Neutralization Solution (0.5 M Tris-HCl, 3 M NaCl, pH 7.5) 2× 15 min at RT with gentle agitation. Next, the digested DNA was blotted overnight on a nylon membrane (Sigma-Aldrich, 11417240001) by capillary transfer using 20×SSC as transfer buffer. After transfer, the DNA was fixed on the membrane using UV crosslinking at 0.120 J. The membrane was washed twice with 2×SSC before incubation with 18 mL of prewarmed DIG Easy Hyb granules at 42° C. for 1 hour. Next, the blotting membrane was incubated with hybridization solution (2 µl of Telomere probe in 10 mL of prewarmed DIG Easy Hyb granules) for 3 hours at 42° C. Hybridization solution was discarded and the membrane was washed 2× 5 min with Stringent Wash Buffer I (2×SSC, 0.1% SDS) at RT and 2× 20 min with Stringent Wash Buffer II (0.2×SSC, 0.1% SDS) at 50° C.

The blotting membrane was rinsed with 100 mL 1× Washing buffer for 5 min at RT before incubation with 100 mL of freshly prepared 1× Blocking solution for 30 min at RT. Next, the membrane was incubated with 100 mL of Anti-DIG-AP working solution for 30 min at RT. To prepare anti-DIG-AP working solution, anti-DIG-AP vial was spun to reduce background from aggregated antibodies and then diluted 1:10000 in 1× Blocking solution. The membrane was washed 2× 15 min with 100 mL 1× Washing solution at RT and then incubated with 100 mL of 1× Detection buffer for 5 min at RT. Detection buffer was discarded and the wet membrane was placed with DNA facing up on an opened hybridization bag. About 3 mL of substrate solution were applied dropwise to the membrane, which was immediately covered with the second sheet of the hybridization bag and incubated for 5 min at RT. Before exposure, the excess of substrate solution was squeezed out and the bag was sealed. The membrane was imaged using the Chemi blots mode of an iBright FL1500 Imaging System (Thermo Fisher).

Results of the assay: With this assay, we demonstrate that full restoration of telomere length is achieved after 4 weeks of treatment of patient-derived iPSCs with a PAPD5 inhibitor at concentrations corresponding to more than 80% target engagement (FIG. 2B, Table 7). A dose of 0.5 nM of Example 506 is sufficient to promote telomere elongation up to 8 kb, which falls into the range of average telomere length for healthy individuals in this age group. Of note, telomeres isolated from healthy donor-derived iPSCs do not show an increase in length upon 4 weeks of treatment with the highest dose of the compounds (FIG. 2B).

EXAMPLES

The following examples 1-11 are provided for illustration of the invention. They should not be considered as limiting the scope of the invention, but merely as being representative thereof.

PMB-protected (3-hydroxypyridin-2-yl) ethan-1-one Intermediates of Formula (VI)

PMB-protected (3-hydroxypyridin-2-yl) ethan-1-one intermediate 1

1-{6-Methoxy-3-[(4-methoxyphenyl)methoxy]-5-(3-methoxypropoxy)pyridin-2-yl}ethan-1-one a) 5-Bromo-2-fluoro-3-(3-methoxypropoxy)pyridine A solution of 5-bromo-2-fluoropyridin-3-ol (30.0 g, 156 mmol), 1-bromo-3-methoxypropane (28.7 g, 1.2 eq., 188 mmol) and dipotassium carbonate (36.7 g, 1.7 eq., 266 mmol) was stirred in dry acetonitrile (250 mL) at 80° C. for 2 hours. After cooling to room temperature, the solution was concentrated under reduced pressure, and the resulting oil was diluted with water, extracted with three portions of ethyl acetate, and washed with brine. The combined organic layers were concentrated under reduced pressure to give 5-bromo-2-fluoro-3-(3-methoxypropoxy)pyridine (39.9 g, 143 mmol, 92% yield) as a white solid.

MS m/e: [M+H]$^+$ 263.9 b) 5-Bromo-2-methoxy-3-(3-methoxypropoxy)pyridine

To a solution of 5-bromo-2-fluoro-3-(3-methoxypropoxy)pyridine (40.0 g, 152 mmol) in methanol (340 mL) was added sodium methoxide (24.5 g, 3.0 eq., 454 mmol) at 20° C. After stirring at 85° C. for 6 hours the mixture was diluted with water, extracted with dichloromethane and dried with anhydrous sodium sulfate. The organic layer was concentrated to give 5-bromo-2-methoxy-3-(3-methoxypropoxy)pyridine (41.2 g, 142 mmol, 94% yield) as a white solid.

MS m/e: [M+H]$^+$ 277.9 c) 6-Methoxy-5-(3-methoxypropoxy)pyridin-3-ol

To a solution of 5-bromo-2-methoxy-3-(3-methoxypropoxy)pyridine (45.3 g, 164 mmol) and triisopropyl borate (37.0 g, 1.2 eq., 197 mmol) in tetrahydrofuran (13 mL) at −78° C. was added n-butyllithium (2.5 M in hexanes, 92.0 mL, 1.4 eq., 230 mmol) while keeping the internal temperature below −65° C. After stirring the mixture at −78° C. for 30 minutes and allowing it to warm to room temperature over a period of 2 hours aqueous hydrogen peroxide solution (30% w/w, 14.0 mL, 1.1 eq., 180 mmol) was added dropwise. After the mixture was stirred at room temperature over night, the solution was concentrated in vacuo. The residue was diluted with water (200 mL) and extracted with three 200-mL portions of ethyl acetate. The combined organic layers were washed with brine, dried over anhydrous sodium sulfate, filtered, and concentrated in vacuo. The residue was purified by flash column chromatography (silica gel, 0-20% ethyl acetate in petroleum ether) to give 6-methoxy-5-(3-methoxypropoxy)pyridin-3-ol (32.5 g, 145 mmol, 88% yield) as a light yellow oil.

MS m/e: [M+H]$^+$ 214.0 d) 2-Bromo-6-methoxy-5-(3-methoxypropoxy)pyridin-3-ol

To a solution of 6-methoxy-5-(3-methoxypropoxy)pyridin-3-ol (32.5 g, 145 mmol) in acetonitrile (300 mL) was added N-bromosuccinimide (26.3 g, 1.02 eq., 148 mmol). After stirring at room temperature for 5 minutes the reaction mixture was diluted with water (100 mL) and extracted with three 80-mL portions of ethyl acetate. The combined organic layers were washed with brine, dried over anhydrous sodium sulfate, filtered and concentrated in vacuo. The residue was purified by flash column chromatography (silica gel, 0-5% ethyl acetate in petroleum ether) to give 2-bromo-6-methoxy-5-(3-methoxypropoxy)pyridin-3-ol (34.7 g, 113 mmol, 95% purity, 78% yield) as a white solid.

MS m/e: [M+H]$^+$ 293.8 e) 2-Bromo-6-methoxy-3-[(4-methoxyphenyl)methoxy]-5-(3-methoxypropoxy)pyridine

A solution of 2-bromo-6-methoxy-5-(3-methoxypropoxy) pyridin-3-ol (34.7 g, 113 mmol), (4-methoxyphenyl)methanol (15.9 g, 1 eq., 115 mmol) and triphenylphosphine (35.5 g, 1.2 eq., 135 mmol) was stirred in dry tetrahydrofuran (330 mL) at 0° C. under a nitrogen atmosphere. To this mixture was added dropwise (E)-N-{[(propan-2-yloxy)carbonyl]imino}(propan-2-yloxy)formamide (26.7 mL, 1.2 eq., 135 mmol) over a period of 5 minutes. After stirring at room temperature for 1 hour the mixture was concentrated under reduced pressure and the resulting oil purified by flash column chromatography (silica gel, 5-15% ethyl acetate in petroleum ether) to give 2-bromo-6-methoxy-3-[(4-methoxyphenyl)methoxy]-5-(3-methoxypropoxy)pyridine (27 g, 59 mmol, 90% purity, 52% yield) as a yellow solid.

MS m/e: [M+H]$^+$ 411.8 f) 1-{6-Methoxy-3-[(4-methoxyphenyl)methoxy]-5-(3-methoxypropoxy)pyridin-2-yl}ethan-1-one To a solution of 2-bromo-6-methoxy-3-[(4-methoxyphenyl)methoxy]-5-(3-methoxypropoxy)pyridine (27.0 g, 65.5 mmol) and tributyl(1-ethoxyethenyl)stannane (30.7 g, 1.3 eq., 85.1 mmol) in N,N-dimethylformamide (270 mL) was added tetrakis(triphenylphosphine) palladium (7.57 g, 0.1 eq., 6.55 mmol) at 20° C. The mixture was heated at 100° C. over night. After cooling the mixture to room temperature 1 N aqueous hydrochloric acid solution (10 mL) was added. After stirring at 20° C. for 1 hour the suspension was poured into water (80 mL) and extracted with three 80-mL portions of ethyl acetate. The combined organic layers were washed with brine (150 mL), dried over anhydrous sodium sulfate and concentrated under reduced pressure. The crude residue was purified by flash column chromatography (silica gel, 0-30% ethyl acetate in heptane) to give 1-{6-methoxy-3-[(4-methoxyphenyl)methoxy]-5-(3-methoxypropoxy)pyridin-2-yl}ethan-1-one (20.2 g, 48.4 mmol, 90% purity, 74% yield) as brown oil.

MS m/e: [M+H]$^+$ 376.0

PMB-protected (3-hydroxypyridin-2-yl) ethan-1-one intermediate 2

1-(6-Cyclopropyl-3-((4-methoxybenzyl)oxy)-5-(3-methoxypropoxy)pyridin-2-yl) ethan-1-one a) 5-Bromo-2-chloro-3-(3-methoxypropoxy)pyridine To a suspension of 5-bromo-2-chloropyridin-3-ol (25.0 g, 120 mmol) and dipotassium carbonate (33.2 g, 2.0 eq., 240 mmol) in acetonitrile (500 mL) was added 1-bromo-3-methoxypropane (20.2 g, 1.1 eq., 132 mmol) at 20° C. After stirring at 50° C. over night, the suspension was poured into water (500 mL) and extracted with three 200-mL portions of ethyl acetate. The combined organic layers were washed with brine (100 mL), dried over anhydrous sodium sulfate, and concentrated under reduced pressure. The residue was purified by silica gel column chromatography (petroleum ether: ethyl acetate=5:1) to give 5-bromo-2-chloro-3-(3-methoxypropoxy)pyridine (31.0 g, 108 mmol, 98% purity, 90% yield) as white solid.

MS m/e: [M+H]$^+$ 280.0 b) 6-Chloro-5-(3-methoxypropoxy)pyridin-3-ol

To a solution of 5-bromo-2-methoxy-3-(3-methoxypropoxy)pyridine (25.0 g, 89 mmol) and tris(propan-2-yl) borate (25.1 g, 1.5 eq., 134 mmol) in tetrahydrofuran (300 mL) at −78° C. was added n-butyllithium (2.5 M in hexane, 49.9 mL, 1.4 eq., 125 mmol) while keeping the internal temperature below −65° C. After stirring at −78° C. for 30 minutes the mixture was allowed to warm to room temperature during 3 hours. Hydrogen peroxide 30% w/w (13.8 mL, 2.0 eq., 178 mmol) was added dropwise. After stirring at room temperature over night the reaction mixture was concentrated under reduced pressure. The residue was diluted with water (500 mL) and extracted with three 500-mL portions of ethyl acetate. The combined organic layers were washed with brine, dried over anhydrous sodium sulfate, filtered and concentrated in vacuo. The residue was purified by silica gel column chromatography (petroleum ether: ethyl acetate=5:1 to 2:1) to give 6-chloro-5-(3-methoxypropoxy)pyridin-3-ol (17.0 g, 97% purity, 85% yield) as white solid.

MS m/e: [M+H]$^+$ 218.1 c) 6-Chloro-2-iodo-5-(3-methoxypropoxy)pyridin-3-ol

To a solution of 6-chloro-5-(3-methoxypropoxy)pyridin-3-ol (14.0 g, 64.3 mmol) and sodium carbonate (13.6 g, 2.0 eq, 129 mmol) in water (700 mL) was added iodine (16.3 g, 1.0 eq, 64.3 mmol). After stirring at room temperature over night, the mixture was diluted with saturated aqueous ammonium chloride (800 mL), then the mixture was extracted with three 500-mL portions of ethyl acetate. The combined organic layers were washed with saturated sodium sulfite solution (500 mL), dried over anhydrous sodium sulfate, filtered and concentrated to give 6-chloro-2-iodo-5-(3-methoxypropoxy)pyridin-3-ol (21.0 g, 97% yield, 92% yield) as a brown solid.

MS m/e: [M+H]$^+$ 343.8 d) 2-Chloro-6-iodo-5-((4-methoxybenzyl)oxy)-3-(3-methoxypropoxy)pyridine

To a suspension of 6-chloro-2-iodo-5-(3-methoxypropoxy)pyridin-3-ol (42.0 g, 122 mmol) and potassium carbonate (25.3 g, 1.5 eq., 183 mmol) in acetonitrile (840 mL) was added 1-(chloromethyl)-4-methoxybenzene (23.0 g, 1.2 eq., 147 mmol) at room temperature. After stirring at room temperature, the suspension was poured into water (2000 mL) and extracted with three 1000-mL portions of ethyl acetate. The combined organic layers were washed with brine (500 mL), dried over anhydrous sodium sulfate, and concentrated under reduced pressure to give 2-chloro-6-iodo-5-((4-methoxybenzyl)oxy)-3-(3-methoxypropoxy)pyridine (50.0 g, 86% purity, 76% yield) as a brown solid, which was used in the next step without further purification.

MS m/e: [M+H]$^+$ 464.0 e) 1-(6-Chloro-3-((4-methoxybenzyl)oxy)-5-(3-methoxypropoxy)pyridin-2-yl)ethan-1-one To a solution of 2-chloro-6-iodo-5-((4-methoxybenzyl)oxy)-3-(3-methoxypropoxy)pyridine (50.0 g, 91.7 mmol) and tributyl(1-ethoxyethenyl)stannane (40.3 mL, 1.3 eq., 119 mmol) in N,N-dimethylformamide (500 mL, 91.7 mmol) was added tetrakis(triphenylphosphine) palladium (5.3 g, 0.05 eq., 4.58 mmol) at 20° C. After stirring at 110° C. over night, the mixture was allowed to warm to room temperature, treated with 1 M aqueous hydrochloric acid solution (250 mL) and stirred 1 hour at room temperature. The mixture was poured into saturated aqueous potassium fluoride solution (1000 mL), diluted with water (1500 mL) and extracted with three 1000-mL portions of ethyl acetate. The combined organic layers were washed with brine (800 mL), dried over anhydrous sodium sulfate, and concentrated under reduced pressure. The residue was purified by silica gel column chromatography (eluted with petroleum ether: ethyl acetate=5:1 to 3:1) to give 1-(6-chloro-3-((4-methoxybenzyl)oxy)-5-(3-methoxypropoxy)pyridin-2-yl)ethan-1-one (31.0 g, 88% purity, 78% yield) as yellow solid.

MS m/e: [M+H]$^+$ 380.0 f) 1-(6-Cyclopropyl-3-((4-methoxybenzyl)oxy)-5-(3-methoxypropoxy)pyridin-2-yl)ethan-1-one To a solution of 1-(6-chloro-3-((4-methoxybenzyl)oxy)-5-(3-methoxypropoxy)pyridin-2-yl)ethan-1-one (10.0 g, 26.3 mmol), cyclopropylboronic acid (6.78 g, 3.0 eq., 79 mmol) and potassium carbonate (10.9 g, 3.0 eq., 79 mmol) in water (20 mL) and 1,4-dioxane (100 mL) was added tetrakis(triphenylphosphine) palladium (3.04 g, 0.1 eq., 2.63 mmol) at room temperature under nitrogen. After stirring at 110° C. for 24 hours, the mixture was cooled to room temperature, poured into water (500 mL) and extracted with three 200-mL portions of dichloromethane. The combined organic layers were washed with brine (100 mL), dried over anhydrous sodium sulfate, and concentrated under reduced pressure. The residue was purified by silica gel column chromatography (petroleum ether: ethyl acetate=5:1 to 3:1) to give 1-(6-cyclopropyl-3-((4-methoxybenzyl)oxy)-5-(3-methoxypropoxy)pyridin-2-yl)ethan-1-one (6.8 g, 92% purity, 62% yield) as yellow oil.

MS m/e: [M+H]$^+$ 386.0

(3-Hydroxypyridin-2-yl)ethan-1-one Intermediates of Formula (V)

General procedure I: deprotection of a p-methoxybenzyl group

To a solution of a 1-(3-((4-methoxybenzyl)oxy)-pyridin-2-yl) ethan-1-one derivative of formula (VI) (1.0 eq. ) in dichloromethane is added trifluoroacetic acid (15.0 eq.) at room temperature. After the reaction is complete, the suspension is poured into saturated aqueous sodium bicarbonate solution and extracted with three portions of dichloromethane. The combined organic layers are washed with brine, dried over anhydrous sodium sulfate, and concentrated under reduced pressure. The crude is purified by silica gel column chromatography (eluted with petroleum ether: ethyl acetate=5:1 to 3:1) to give an intermediate of formula (V).

(3-Hydroxypyridin-2-yl)ethan-1-one intermediate 1

1-[3-Hydroxy-6-methoxy-5-(3-methoxypropoxy)pyridin-2-yl]ethan-1-one

The title compound was obtained from 1-{6-methoxy-3-[(4-methoxyphenyl)methoxy]-5-(3-methoxypropoxy)pyridin-2-yl}ethan-1-one as yellow oil in 85% yield according to general procedure I.

MS m/e: [M+H]$^+$ 256.0

(3-Hydroxypyridin-2-yl) ethan-1-one intermediate 2

1-(6-Cyclopropyl-3-hydroxy-5-(3-methoxypropoxy)pyridin-2-yl)ethan-1-one

The title compound was obtained from 1-(6-cyclopropyl-3-((4-methoxybenzyl)oxy)-5-(3-methoxypropoxy)pyridin-2-yl)ethan-1-one as yellow oil in 88% yield according to general procedure I.

MS m/e: [M+H]$^+$ 265.9

Ketone Intermediates of Formula (IV)

General Procedure II: Cyclocondensation of (3-hydroxypyridin-2-yl)ethan-1-one intermediates of formula (V) with aldehydes or ketones To a solution of a 1-[3-hydroxy-pyridin-2-yl]ethan-1-one intermediate of formula (V) (1.0 eq.) and pyrrolidine (1.2 eq.) in methanol is added an aldehyde or ketone (1.2-5.0 eq.) in a sealed pressure tube. After stirring at the indicated temperature (between 20 and 100° C.) for 12 hours, the reaction mixture is allowed to cool to room temperature, diluted with water and extracted with three portions of ethyl acetate. The combined organic layers are washed with brine, dried over anhydrous sodium sulfate, filtered and concentrated in vacuo. The residue is purified by flash column chromatography (silica gel, 0-5% ethyl acetate in petroleum ether) to give a 2,3-dihydro-4H-pyrano[3,2-b]pyridin-4-one intermediate of formula (IV).

Ketone Intermediate 1

(RS)-2-Isopropyl-6-methoxy-7-(3-methoxypropoxy)-2,3-dihydro-4H-pyrano[3,2-b]pyridin-4-one The title compound was obtained from 1-[3-hydroxy-6-methoxy-5-(3-methoxypropoxy)-2-pyridyl]-1-ethanone as yellow solid in 63% yield according to general procedure II at room temperature.

MS m/e: [M+H]$^+$ 310.2

Ketone Intermediate 2

(RS)-2-(tert-Butyl)-6-methoxy-7-(3-methoxypropoxy)-2,3-dihydro-4H-pyrano[3,2-b]pyridin-4-one The title compound was obtained from 1-[3-hydroxy-6-methoxy-5-(3-methoxypropoxy)pyridin-2-yl]ethan-1-one as yellow solid in 64% yield according to general procedure II at a reaction temperature of 50° C.

MS m/e: [M+H]$^+$ 324.2

Ketone Intermediate 3

(RS)-2-(tert-Butyl)-6-cyclopropyl-7-(3-methoxypropoxy)-2,3-dihydro-4H-pyrano[3,2-b]pyridin-4-one The title compound was obtained from 1-(6-cyclopropyl-3-hydroxy-5-(3-methoxypropoxy)pyridin-2-yl)ethan-1-one as yellow solid in 45% yield according to general procedure II at a reaction temperature of 100° C.

MS m/e: [M+H]$^+$ 334.2

Ketone Intermediate 4

6'-Methoxy-7'-(3-methoxypropoxy)spiro[cyclopentane-1,2'-pyrano[3,2-b]pyridin]-4'(3'H)-one The title compound was obtained from 1-[3-hydroxy-6-methoxy-5-(3-methoxypropoxy)-2-pyridyl]-1-ethanone as yellow oil in 30% yield according to general procedure II at a reaction temperature of 100° C.

MS m/e: [M+H]$^+$ 322.0

(Dimethylamino)Methylene Intermediates of Formula (III)

General Procedure III: condensation of 2,3-dihydro-4H-pyrano[3,2-b]pyridin-4-ones of formula (IV) with N,N-dimethylformamide dimethyl acetal After heating a solution of a 2,3-dihydro-4H-pyrano[3,2-b]pyridin-4-one derivative of formula (IV) (1.0 eq.) in N,N-dimethylformamide dimethyl acetal (28.0 eq.) at the indicated temperature for 12 hours the mixture is concentrated to dryness and the residue is purified by flash column chromatography (silica gel, 0-5% ethyl acetate in petroleum ether) or by reversed phase HPLC (C18 column, 5-95% acetonitrile in aqueous ammonium bicarbonate solution) to give a 3-[(dimethylamino)methylene]-2,3-dihydro-4H-pyrano[3,2-b]pyridin-4-one intermediate of formula X.

(Dimethylamino)Methylene Intermediate 1

(RS)-3-((Dimethylamino)methylene)-2-isopropyl-6-methoxy-7-(3-methoxypropoxy)-2,3-dihydro-4H-pyrano[3,2-b]pyridin-4-one The title compound was obtained from (RS)-2-isopropyl-6-methoxy-7-(3-methoxypropoxy)-2,3-dihydro-4H-pyrano[3,2-b]pyridin-4-one as yellow oil in 57% yield according to general procedure III at a reaction temperature of 100° C.

MS m/e: [M+H]$^+$ 365.4

(Dimethylamino)Methylene Intermediate 2

(RS)-2-(tert-Butyl)-3-((dimethylamino)methylene)-6-methoxy-7-(3-methoxypropoxy)-2,3-dihydro-4H-pyrano[3,2-b]pyridin-4-one The title compound was obtained from (RS)-2-(tert-butyl)-6-methoxy-7-(3-methoxypropoxy)-2,3-dihydro-4H-pyrano[3,2-b]pyridin-4-one as yellow oil in 56% yield according to general procedure III at a reaction temperature of 120° C.

MS m/e: [M+H]$^+$ 379.0

(Dimethylamino)Methylene Intermediate 3

(RS)-2-(tert-Butyl)-6-cyclopropyl-3-((dimethylamino)methylene)-7-(3-methoxypropoxy)-2,3-dihydro-4H-pyrano[3,2-b]pyridin-4-one The title compound was obtained from (RS)-2-(tert-butyl)-6-cyclopropyl-7-(3-methoxypropoxy)-2,3-dihydro-4H-pyrano[3,2-b]pyridin-4-one as yellow solid in 52% yield according to general procedure III at a reaction temperature of 120° C.

MS m/e: [M+H]$^+$ 389.1

(Dimethylamino)Methylene Intermediate 4

3'-((Dimethylamino)methylene)-6'-methoxy-7'-(3-methoxypropoxy)spiro[cyclopentane-1,2'-pyrano[3,2-b]pyridin]-4' (3'H)-one The title compound was obtained from 6'-methoxy-7'-(3-methoxypropoxy)spiro[cyclopentane-1,2'-pyrano[3,2-b]pyridin]-4' (3'H)-one as yellow oil in 60% purity and 82% yield according to general procedure III at a reaction temperature of 120° C. The crude intermediate was used in the next step without purification.

MS m/e: [M+H]$^+$ 377.0

Nitrile Intermediates of Formula (II)

General procedure IV: cyclocondensation of 3-[(dimethylamino)methylene]-2,3-dihydro-4H-pyrano[3,2-b]pyridin-4-one derivatives and cyanoacetamide To a solution of a 3-[(dimethylarino)methylene]-2,3-dihydro-4H-pyrano[3,2-b]pyridin-4-one derivative of formula (III) (1.0 eq.) and cyanoacetamide (1.2 eq.) in methanol is added sodium hydride 60% w/w (4.0 eq.). Stirring the mixture at the indicated temperature over night is followed by dilution with water and extraction with three portions of ethyl acetate. The combined organic layers are washed with brine, dried over anhydrous sodium sulfate, filtered and concentrated in vacuo. The residue is purified by flash column chromatography (silica gel, 0-5% ethyl acetate in petroleum ether) or by C18 column (acetonitrile 0.02% aqueous ammonium bicarbonate solution=05% to 95%) to give a compound of formula (II-a).

General Procedure V: N-alkylation of 3-cyano-2-pyridones

To a solution of a compound of formula (II-a) (1.0 eq.) and dipotassium carbonate (2.8 eq.) in a suitable solvent is added alkylating agent (1.0-5.0 eq.) at 20. Stirring the resulting reaction mixture for 12 hours at a temperature between 20 and 80 is followed by quenching with water and extraction with three portions of ethyl acetate. The combined organic extracts are dried over sodium sulfate, filtered and concentrated in vacuo. The residue is purified by silica gel flash column chromatography, preparative HPLC or preparative TLC (petroleum ether/ethyl acetate=1:1) to give an intermediate of formula (II-b).

General Procedure VI: copper-mediated N-alkylation of 3-cyano-2-pyridones

A mixture of a compound of formula (II-a) (1.0 eq.), a potassium alkyltrifluoroborate (1.5 eq.), copper bis(acetate) (2.0 eq.), 1,10-phenanthroline (1.0 eq.) and dipotassium carbonate (2.0 eq.) in 20% v/v water in acetonitrile is deoxygenated by bubbling nitrogen through the solution for 10 minutes. The mixture is subsequently heated at reflux for 12 hours under an atmosphere of nitrogen. After cooling to room temperature, the mixture is diluted with water and extracted with three portions of ethyl acetate. The combined organic layers are washed with brine, dried over anhydrous sodium sulfate, filtered and concentrated under reduced pressure. The residue is purified by flash column chromatography (silica gel, 0-10% methanol in dichloromethane) to give an intermediate of formula (II-b).

Nitrile Intermediate 1

(RS)-6-Isopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-3-((dimethylamino)methylene)-2-isopropyl-6-methoxy-7-(3-methoxypropoxy)-2,3-dihydro-4H-pyrano[3,2-b]pyridin-4-one as yellow oil in 53% yield according to general procedure IV using sodium methoxide (2.0 eq.) instead of sodium hydride. The reaction was performed at 120° C.
MS m/e: [M+H]⁺ 386.2

Nitrile Intermediate 2

(RS)-6-(tert-Butyl)-2-methoxy-3-(3-methoxypropoxy)-9-oxo-9,10-dihydro-6H-pyrano[3,2-b:4,5-b']dipyridine-8-carbonitrile The title compound was obtained from (RS)-2-(tert-butyl)-3-((dimethylamino)methylene)-6-methoxy-7-(3-methoxypropoxy)-2,3-dihydro-4H-pyrano[3,2-b]pyridin-4-one as yellow solid in 25% yield according to general procedure IV at room temperature.
MS m/e: [M+H]⁺ 400.1

Nitrile Intermediate 3

(RS)-6-(tert-Butyl)-2-cyclopropyl-3-(3-methoxypropoxy)-9-oxo-9,10-dihydro-6H-pyrano[3,2-b:4,5-b']dipyridine-8-carbonitrile The title compound was obtained from (RS)-2-(tert-butyl)-6-cyclopropyl-3-((dimethylamino)methylene)-7-(3-methoxypropoxy)-2,3-dihydro-4H-pyrano[3,2-b]pyridin-4-one as yellow solid in 71% yield according to general procedure IV at a reaction temperature of 95
MS m/e: [M+H]⁺ 410.1

Nitrile Intermediate 4

2'-Methoxy-3'-(3-methoxypropoxy)-9'-oxo-9',10'-dihydrospiro[cyclopentane-1,6'-pyrano[3,2-b:4,5-b']dipyridine]-8'-carbonitrile The title compound was obtained from 3'-((dimethylamino)methylene)-6'-methoxy-7'-(3-methoxypropoxy)spiro[cyclopentane-1,2'-pyrano[3,2-b]pyridin]-4'(3'H)-one as yellow solid in 41% yield according to general procedure IV at room temperature.
MS m/e: [M+H]⁺ 398.0

Nitrile Intermediate 5

(RS)-6-Isopropyl-2-methoxy-3-(3-methoxypropoxy)-10-methyl-9-oxo-9,10-dihydro-6H-pyrano[3,2-b:4,5-b']dipyridine-8-carbonitrile The title compound was obtained from (RS)-6-isopropyl-2-methoxy-3-(3-methoxypropoxy)-9-oxo-9,10-dihydro-6H-pyrano[3,2-b:4,5-b']dipyridine-8-carbonitrile as yellow solid in 94% yield according to general procedure V at room temperature using iodomethane as alkylating agent and 20% v/v water in methanol as solvent.
MS m/e: [M+H]⁺ 400.0

Nitrile Intermediate 6

(RS)-10-Ethyl-6-isopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-6-isopropyl-2-methoxy-3-(3-methoxypropoxy)-9-oxo-9,10-dihydro-6H-pyrano[3,2-b:4,5-b']dipyridine-8-carbonitrile as yellow solid in 80% yield according to general procedure V at 40 using iodoethane as alkylating agent and 20% v/v water in methanol as solvent.
MS m/e: [M+H]⁺ 413.9

Nitrile Intermediate 7

(RS)-10-(2-Fluoroethyl)-6-isopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-6-isopropyl-2-methoxy-3-(3-methoxypropoxy)-9-oxo-9,10-dihydro-6H-pyrano[3,2-b:4,5-b']dipyridine-8-carbonitrile as yellow solid in 37% yield according to general procedure V at 80 using 1-fluoro-2-iodoethane (5.0 eq.) as alkylating agent and N,N-dimethylformamide as solvent.
MS m/e: [M+H]⁺ 432.2

Nitrile Intermediate 8

(RS)-10-(2,2-Difluoroethyl)-6-isopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-6-isopropyl-2-methoxy-3-(3-methoxypropoxy)-9-oxo-9,10-dihydro-6H-pyrano[3,2-b:4,5-b']dipyridine-8-carbonitrile as yellow solid in 35% yield according to general procedure V at 60 using 1,1-difluoro-2-iodoethane (5.0 eq.) as alkylating agent and N,N-dimethylformamide as solvent.
MS m/e: [M+H]⁺ 450.2

Nitrile Intermediate 9

(RS)-10-Cyclopropyl-6-isopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-6-isopropyl-2-methoxy-3-(3-methoxypropoxy)-9-oxo-9,10-dihydro-6H-pyrano[3,2-b:4,5-b']dipyridine-8-carbonitrile and potassium cycloproyltrifluoroborate as yellow solid in 54% yield according to general procedure VI.
MS m/e: [M+H]⁺ 426.2

Nitrile Intermediate 10

(RS)-6-(tert-Butyl)-10-cyclopropyl-2-methoxy-3-(3-methoxypropoxy)-9-oxo-9,10-dihydro-6H-pyrano[3,2-b:4,5-b']dipyridine-8-carbonitrile The title compound was obtained from (RS)-6-(tert-butyl)-2-methoxy-3-(3-methoxypropoxy)-9-oxo-9,10-dihydro-6H-pyrano[3,2-b:4,5-b']dipyridine-8-carbonitrile and potassium cycloproyltrifluoroborate as yellow solid in 81% yield according to general procedure VI.
MS m/e: [M+H]⁺ 440.0

Nitrile Intermediate 11

(RS)-6-(tert-Butyl)-2,10-dicyclopropyl-3-(3-methoxypropoxy)-9-oxo-9,10-dihydro-6H-pyrano[3,2-b:4,5-b']dipyridine-8-carbonitrile The title compound was obtained from (RS)-6-(tert-butyl)-2-cyclopropyl-3-(3-methoxypropoxy)-9-oxo-9,10-dihydro-6H-pyrano[3,2-b:4,5-b']dipyridine-8-carbonitrile and potassium cycloproyltrifluoroborate as yellow solid in 68% yield according to general procedure VI.
MS m/e: [M+H]⁺ 450.0

Examples

General Procedure VII: Hydrolysis of Nitriles
To a solution of a nitrile of formula (II) (1.0 eq.) in ethanol (4-10 mL/mmol) is added 5 M aqueous potassium hydroxide solution (4-10 mL/mmol). After stirring at 100° C. for 1-3 days, the mixture is concentrated, diluted with water and adjusted to pH 5-6 with 1.0 M aqueous hydrochloric solution. The mixture is extracted with three portions of ethyl acetate. The combined organic layers are washed with brine, dried over anhydrous sodium sulfate, filtered, and concentrated under reduced pressure. The residue is purified by reversed phase HPLC (using C18 column, eluted with acetonitrile: 0.02% aqueous ammonium bicarbonate solution=5% to 95%) to give a carboxylic acid of formula I.

Example 501

(RS)-6-Isopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 19% yield according to general procedure VII. Nitrile: (RS)-6-isopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 405.1

$^1$HNMR (CDCl$_3$, 400 MHz) δ 13.89 (s, 1H), 10.02 (s, 1H), 8.24 (s, 1H), 6.75 (s, 1H), 5.01 (d, J=6.0 MHz, 1H), 4.18-4.14 (m, 2H), 4.03 (s, 3H), 3.56 (t, J=5.6 MHz, 2H), 3.36 (s, 3H), 2.19-2.13 (m, 3H), 1.03-1.01 (m, 6H) ppm.

Example 502

(RS)-6-Isopropyl-2-methoxy-3-(3-methoxypropoxy)-10-methyl-9-oxo-9,10-dihydro-6H-pyrano[3,2-b:4,5-b']dipyridine-8-carboxylic acid The title compound was obtained as yellow solid in 24% yield according to general procedure VII. Nitrile: (RS)-6-isopropyl-2-methoxy-3-(3-methoxypropoxy)-10-methyl-9-oxo-9,10-dihydro-6H-pyrano[3,2-b:4,5-b']dipyridine-8-carbonitrile MS m/e: [M+H]$^+$ 419.1

$^1$H-NMR (DMSO-d$_6$, 400 Hz) δ 14.75 (s, 1H), 8.22 (s, 1H), 7.23 (s, 1H), 5.01 (d, J=8.8 MHz, 1H), 4.20-4.10 (m, 5H), 3.92 (s, 3H), 3.47 (t, J=6.0 MHz, 2H), 3.25 (s, 3H), 2.02-1.95 (m, 2H), 0.96 (d, J=6.4 MHz, 3H), 0.81 (d, J=6.8 Hz, 3H) ppm.

Example 503

(RS)-10-Ethyl-6-isopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 19% yield according to general procedure VII. Nitrile: (RS)-10-ethyl-6-isopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 433.2

$^1$H-NMR (CDCl$_3$, 400 Hz) δ 14.74 (s, 1H), 8.19 (s, 1H), 6.84 (s, 1H), 5.11-4.99 (m, 2H), 4.65 (d, J=8.0 MHz, 1H), 4.22-4.15 (m, 2H), 4.02 (s, 3H), 3.59(t, J=5.2 MHz, 2 H), 3.38 (s, 3H), 2.19-2.07 (m, 3H), 1.51 (t, J=6.8 MHz, 3H), 1.02 (d, J=6.8 MHz, 3H), 0.91 (d, J=6.8 MHz, 3 H)ppm.

Example 504

(RS)-10-Cyclopropyl-6-isopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 52% yield according to general procedure VII. Nitrile: (RS)-10-cyclopropyl-6-isopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 445.2

$^1$HNMR (CDCl$_3$, 400 MHz) δ 14.4 (s, 1H), 8.17 (s, 1H), 6.82 (s, 1H), 4.67 (d, J=7.6 MHz, 1H), 4.21-4.15 (m, 2H), 3.95 (s, 3H), 3.78-3.72 (m, 1H), 3.59 (t, J=6.0 MHz, 2H), 3.38 (s, 3H), 2.19-2.13 (m, 2H), 2.08-2.01 (m, 1H), 1.38-1.31 (m, 1H), 1.07-1.01 (m, 1H), 0.98 (d, J=6.8 MHz, 3H), 0.94 (d, J=6.8 MHz, 3H), 0.74-0.67 (m, 1H), 0.48-0.42 (m, 1H) ppm.

Example 505

(RS)-6-(tert-Butyl)-2-methoxy-3-(3-methoxypropoxy)-9-oxo-9,10-dihydro-6H-pyrano[3,2-b:4,5-b']dipyridine-8-carboxylic acid The title compound was obtained as yellow solid in 37% yield according to general procedure VII. Nitrile: (RS)-6-(tert-butyl)-2-methoxy-3-(3-methoxypropoxy)-9-oxo-9,10-dihydro-6H-pyrano[3,2-b:4,5-b']dipyridine-8-carbonitrile MS m/e: [M+H]$^+$ 419.1

$^1$H-NMR (DMSO-d$_6$, 400 MHz) δ 14.85 (br s, 1H), 12.96 (s, 1H), 8.13 (s, 1H), 7.09 (s, 1H), 5.23 (s, 1H), 4.15-4.09 (m, 2H), 4.03 (s, 3H), 3.45 (t, J=6.4 MHz, 2H), 3.25 (s, 3H), 2.00-1.95 (m, 2H), 0.86 (s, 9H) ppm.

Example 506

(RS)-6-(tert-Butyl)-10-cyclopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 30% yield according to general procedure VII. Nitrile: (RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 459.1

$^1$H-NMR (DMSO-d$_6$, 400 MHz) δ 14.58 (br s, 1H), 8.12 (s, 1H), 7.17 (s, 1H), 5.14 (s, 1H), 4.20-4.10 (m, 2H), 3.86 (s, 3H), 3.73-3.70 (m, 1H), 3.47 (t, J=6.4 MHz, 2H), 3.26 (s, 3H), 2.02-1.96 (m, 2H), 1.35-1.31 (m, 1H), 0.91-0.89 (m, 1H), 0.79-0.72 (m, 10H), 0.31-0.26 (m, 1H) ppm.

Example 507

(RS)-6-(tert-Butyl)-2-cyclopropyl-3-(3-methoxypropoxy)-9-oxo-9,10-dihydro-6H-pyrano[3,2-b:4,5-b']dipyridine-8-carboxylic acid The title compound was obtained as yellow solid in 37% yield according to general procedure VII. Nitrile: (RS)-6-(tert-butyl)-2-cyclopropyl-3-(3-methoxypropoxy)-9-oxo-9,10-dihydro-6H-pyrano[3,2-b:4,5-b']dipyridine-8-carbonitrile MS m/e: [M+H]$^+$ 429.1

$^1$H-NMR (CDOD, 400 MHz) δ 8.21 (s, 1H), 6.91 (s, 1H), 5.14 (s, 1H), 4.21-4.16 (m, 2H), 3.61 (t, J=6.4 MHz, 2H), 3.36 (s, 3H), 2.44-2.39 (m, 1H), 2.13-2.10 (m, 2H), 1.30-1.24 (m, 1H), 1.11-1.07 (m, 1H), 0.96-0.93 (m, 11H) ppm.

Example 508

(RS)-6-(tert-Butyl)-2,10-dicyclopropyl-3-(3-methoxypropoxy)-9-oxo-9,10-dihydro-6H-pyrano[3,2-b:4,5-b']dipyridine-8-carbonitrile The title compound was obtained as yellow solid in 36% yield according to general procedure VII. Nitrile: (RS)-6-

(tert-butyl)-2,10-dicyclopropyl-3-(3-methoxypropoxy)-9-oxo-9,10-dihydro-6H-pyrano[3,2-b:4,5-b']dipyridine-8-carbonitrile MS m/e: [M+H]$^+$ 469.0

$^1$H-NMR (DMSO-d$_6$, 400 MHz) δ 14.59 (br s, 1H), 8.13 (s, 1H), 7.13 (s, 1H), 5.15 (s, 1H), 4.25-4.13 (m, 2H), 3.56-3.51 (m, 3H), 3.27 (s, 3H), 2.40-2.32 (m, 1H), 2.06-2.00 (m, 2H), 1.33-1.27 (m, 1H), 0.93-0.86 (m, 4H), 0.77 (s, 9H), 0.71-0.69 (m, 2H), 0.19-0.16 (m, 1H) ppm.

Example 509

2'-Methoxy-3'-(3-methoxypropoxy)-9'-oxo-9',10'-dihydrospiro[cyclopentane-1,6'-pyrano[3,2-b:4,5-b']dipyridine]-8'-carboxylic acid The title compound was obtained as yellow solid in 21% yield according to general procedure VII. Nitrile: 2'-methoxy-3'-(3-methoxypropoxy)-9'-oxo-9',10'-dihydrospiro[cyclopentane-1,6'-pyrano[3,2-b:4,5-b']dipyridine]-8'-carbonitrile MS m/e: [M+H]$^+$ 417.1

$^1$H-NMR (CDCl$_3$, 400 MHz) δ 14.93 (s, 1H), 12.96 (s, 1H), 8.19 (s, 1H), 7.06 (s, 1H), 4.12 (t, J=5.6 MHz, 2H), 4.05 (s, 3H), 3.45 (t, J=6.4 MHz, 2H), 3.24 (s, 3H), 2.19 (s, 2H), 1.98-1.80 (m, 8H) ppm.

Example 510

(RS)-10-(2-Hydroxyethyl)-6-isopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 17% yield according to general procedure VII. Nitrile: (RS)-10-(2-fluoroethyl)-6-isopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 449.1

$^1$H-NMR (CDCl$_3$, 400 Hz) δ 14.27 (s, 1H), 8.22 (s, 1H), 6.84 (s, 1H), 5.21-5.13 (m, 2H), 4.66 (d, J=8.4 MHz, 1H), 4.25-4.13 (m, 4H), 4.01 (s, 3H), 3.57 (t, J=5.6 MHz, 2 H), 3.37 (s, 3H), 2.24-2.05 (m, 3H), 1.02 (d, J=6.4 MHz, 3H), 0.92 (d, J=6.8 MHz, 3H) ppm.

Example 511

(RS)-10-(2,2-Difluoroethyl)-6-isopropyl-2-methoxy-3-(3-methoxypropoxy)-9-oxo-9,10-dihydro-6H-pyrano[3,2-b:4,5-b']dipyridine-8-carboxylic acid The title compound was obtained as yellow solid in 11% yield according to general procedure VII. Nitrile: (RS)-10-(2,2-difluoroethyl)-6-isopropyl-2-methoxy-3-(3-methoxypropoxy)-9-oxo-9,10-dihydro-6H-pyrano[3,2-b:4,5-b']dipyridine-8-carbonitrile MS m/e: [M+H]$^+$ 469.1

$^1$H-NMR (CDCl$_3$, 400 Hz) δ 14.03 (s, 1H), 8.23 (s, 1H), 6.82 (s, 1H), 6.40-5.98 (m, 2H), 5.73-5.62 (m, 1H), 4.68 (d, J=8.0 MHz, 1H), 4.23-4.13 (m, 2H), 4.01 (s, 3H), 3.61-3.54 (m, 2H), 3.37 (s, 3H), 2.18-2.07 (m, 3H), 1.02 (d, J=6.4 MHz, 3H), 0.91 (d, J=6.8 MHz, 3H) ppm.

Comparative Examples of Formula XX

Example 701

(RS)-5-(tert-Butyl)-9-methoxy-8-(3-methoxypropoxy)-2-oxo-1,2,5,6-tetrahydro-1,10-phenanthroline-3-carboxylic acid a) (RS)-6-(tert-Butyl)-2-chloro-5,6,7,8-tetrahydroquinolin-3-amine To a solution of (RS)-6-(tert-butyl)-2-chloro-3-nitro-5,6,7,8-tetrahydroquinoline (14.5 g, 95% purity, 51.3 mmol) in ethanol (126 mL) and acetic acid (76 mL) was added iron powder (14.3 g, 5.0 eq., 256 mmol) at room temperature. After stirring at room temperature for 24 hours, the reaction mixture was concentrated in vacuo. The residue was diluted with ethyl acetate (200 mL) and saturated aqueous sodium bicarbonate solution (200 mL). The mixture was stirred for additional 10 minutes before it was filtered through a short pad of Celite. The organic phase layer was separated, and the aqueous layer was extracted with ethyl acetate (200 mL). The combined organic layers were washed with brine (100 mL), dried over anhydrous sodium sulfate and concentrated under reduced pressure to give the crude title compound (11.5 g, 89% purity, 84% yield) as white solid.

MS m/e: [M+H]+: 239.0 b) (RS)-6-(tert-Butyl)-2-chloro-5,6,7,8-tetrahydroquinolin-3-ol

To a solution of (RS)-6-(tert-butyl)-2-chloro-5,6,7,8-tetrahydroquinolin-3-amine (11.5 g, 89% purity, 42.9 mmol) in trifluoroacetic acid (110 mL) was added dropwise a solution of sodium nitrite (5.92 g, 2.0 eq, 85.7 mmol) in water (48 mL) at 0° C. After stirring for 1 hour at 0° C. and 40 minutes at 70° C., the reaction mixture was concentrated under reduced pressure. The residue was diluted with water (200 mL) and extracted with three 100-mL portions of ethyl acetate. The combined organic layers were washed with brine, dried over sodium sulfate, filtered and concentrated under reduced pressure. The residue was purified by silica gel column chromatography (eluted with petroleum ether: ethyl acetate=5:1) to give the title compound (7.5 g, 90% purity, 66% yield) as an off-white solid.

MS m/e: [M+H]+: 240.0 c) (RS)-6-(tert-Butyl)-2-chloro-3-(3-methoxypropoxy)-5,6,7,8-tetrahydroquinoline To a solution of (RS)-6-(tert-Butyl)-2-chloro-5,6,7,8-tetrahydroquinolin-3-ol (7.5 g, 90% purity, 28.2 mmol) in acetonitrile (200 mL) was added 1-bromo-3-methoxypropane (8.62 g, 2.0 eq., 56.3 mmol) and potassium carbonate (11.7 g, 3.0 eq, 84.5 mol). After stirring at 100° C. for 5 hours, the reaction mixture was allowed to cool to room temperature. The mixture was diluted with ice-cold water (150 mL) and extracted with two 100-mL portions of ethyl acetate. The combined organic layers were washed with brine (100 mL) and dried over anhydrous sodium sulfate, filtered and concentrated in vacuo. The residue was purified by silica gel column chromatography (eluted with petroleum ether:ethyl acetate=5:1) to give the title compound (7.8 g, 90% purity, 80% yield) as yellow oil.

d) (RS)-6-(tert-Butyl)-2-chloro-3-(3-methoxypropoxy)-6,7-dihydroquinolin-8 (5H)-one oxime To a solution of 2-chloro-6-isopropyl-3-(3-methoxypropoxy)-5,6,7,8-tetrahydroquinoline (1.0 g, 3.3 mmol) and diisopropylamine (1.4 mL, 3.3 eq., 10.0 mmol) in dry tert-butyl methyl ether (10 mL) was added dropwise n-butyl-lithium solution (2.5 M in hexanes, 7.7 mL, 3.0 eq., 19.2 mmol) at −65° C. under an atmosphere of nitrogen gas. After completed addition the reaction mixture was allowed to warm to −40° C. and stirred for 1 hour at this temperature. Then the dark red solution was cooled back to −65° C. and cannulated into a pre-cooled solution of 3-methyl-1-nitrosooxybutane (4.31 mL, 5.0 eq., 32.1 mmol) in dry tert-butyl methyl ether (10 mL) at −65° C. The temperature was gradually allowed to warm to room temperature over 1 h. The reaction mixture was poured into water (150 mL), neutralized by adding 1.0 M aqueous hydrogen chloride solution and extracted with three 50-mL portions of ethyl acetate. The combined organic layers were washed with brine, dried over magnesium sulfate, filtered and concentrated in vacuo. The residue was purified by silica gel column chromatography (eluted with petroleum ether: ethyl acetate=5:1 to 1:1 and then dichloromethane: MeOH=20:1) to give the title compound (1.4 g, 64% yield) as yellow solid.

MS m/e: [M+H]+: 341.0 e) (RS)-6-(tert-Butyl)-2-chloro-3-(3-methoxypropoxy)-6,7-dihydroquinolin-8 (5H)-one To a solution of (RS)-6-(tert-butyl)-2-chloro-3-(3-methoxypropoxy)-6,7-dihydroquinolin-8 (5H)-one oxime (1.1 g, 3.2 mmol) in acetone (8.5 mL) was added 6 M aqueous hydrogen chloride solution (0.5 mL) at room temperature, and the reaction mixture was stirred at 50° C. for 16 hours. After cooling to room temperature, the mixture was poured into saturated aqueous sodium carbonate solution (50 mL). The mixture was extracted with three 50-mL portions of ethyl acetate. The combined organic layers were washed with brine, dried over sodium sulfate, filtered and concentrated in vacuo. The residue was purified by silica gel column chromatography (eluted with petroleum ether: ethyl acetate=5:1 to 1:1) to give the title compound (730 mg, 85% purity, 59% yield) as pale-yellow solid.

MS m/e: [M+H]+: 326.0 f) (RS)-6-(tert-Butyl)-2-chloro-7-((dimethylamino)methylene)-3-(3-methoxypropoxy)-6,7-dihydroquinolin-8(5H)-one The title compound was obtained from (RS)-6-(tert-butyl)-2-chloro-3-(3-methoxypropoxy)-6,7-dihydroquinolin-8(5H)-one as yellow oil in 40% yield according to general procedure III at a reaction temperature of 125° C.

MS m/e: [M+H]+ 381 g) (RS)-5-(tert-Butyl)-9-methoxy-8-(3-methoxypropoxy)-2-oxo-1,2,5,6-tetrahydro-1,10-phenanthroline-3-carbonitrile To a solution of sodium hydride (102 mg, 4.0 eq., 2.55 mmol) in N,N-dimethylformamide (2 mL) at room temperature was added a solution of (RS)-6-(tert-butyl)-2-chloro-7-((dimethylamino)methylene)-3-(3-methoxypropoxy)-6,7-dihydroquinolin-8(5H)-one (347 mg, 0.638 mmol), cyanoacetamide (107 mg, 2.0 eq., 1.28 mmol) and methanol (78 µL, 3 eq., 1.9 mmol) in N,N-dimethylformamide (2 mL). The reaction mixture was stirred for 1 h at room temperature and additional 16 hours at 120. After cooling to room temperature, the mixture was poured into water (30 mL) and extracted with three 20-mL portions of ethyl acetate. The combined organic layers were washed with brine, dried over magnesium sulfate, filtered and concentrated at reduced pressure. The residue was purified by preparative TLC (eluted with dichloromethane:MeOH=25:1) to give a mixture of the title compound and (RS)-5-(tert-butyl)-9-chloro-8-(3-methoxypropoxy)-2-oxo-1,2,5,6-tetrahydro-1,10-phenanthroline-3-carbonitrile as yellow solid. To a solution of this mixture in N-methylpyrrolidone (5 mL) was added sodium methoxide (37.6 mg, 1.1 eq., 0.697 mmol) at room temperature. After stirring at 120° C. for 16 hours, the reaction mixture was poured into water (50 mL) and extracted with three 30-mL portions of ethyl acetate. The combined organic layers were washed with brine, dried over magnesium sulfate, filtered and concentrated at reduced pressure. The residue was purified by preparative TLC (eluted with dichloromethane: MeOH=25:1) to give the title compound (60 mg, yield 22%) as yellow solid.

MS m/e: [M+H]+ 398.0 h) (RS)-5-(tert-Butyl)-9-methoxy-8-(3-methoxypropoxy)-2-oxo-1,2,5,6-tetrahydro-1,10-phenanthroline-3-carboxylic acid The title compound was obtained from (RS)-5-(tert-butyl)-9-methoxy-8-(3-methoxypropoxy)-2-oxo-1,2,5,6-tetrahydro-1,10-phenanthroline-3-carbonitrile as yellow solid in 11% yield according to general procedure VII.

MS m/e: [M+H]+ 417.1

$^1$HNMR (400 MHz, CDCl$_3$): 14.16 (s, 1H), 10.34 (s, 1H), 8.40 (s, 1H), 6.97 (s, 1H), 4.20-4.16 (m, 2H), 4.07 (s, 3H), 3.58 (t, J=6.0 MHz, 2H), 3.37 (s, 3H), 3.24-3.09 (m, 2H), 2.65 (d, J=7.2 MHz, 1H), 2.22-2.12 (m, 2H), 0.82 (s, 9H).

Example 702

(RS)-5-(tert-Butyl)-1-cyclopropyl-9-methoxy-8-(3-methoxypropoxy)-2-oxo-1,2,5,6-tetrahydro-1,10-phenanthroline-3-carboxylic acid a) (RS)-5-(tert-Butyl)-1-cyclopropyl-9-methoxy-8-(3-methoxypropoxy)-2-oxo-1,2,5,6-tetrahydro-1,10-phenanthroline-3-carbonitrile The title compound was obtained from (RS)-5-(tert-butyl)-9-methoxy-8-(3-methoxypropoxy)-2-oxo-1,2,5,6-tetrahydro-1,10-phenanthroline-3-carbonitrile and potassium cycloproyltrifluoroborate as yellow solid in 55% yield according to general procedure VI.

MS m/e: [M+H]+ 438.2 b) (RS)-5-(tert-Butyl)-1-cyclopropyl-9-methoxy-8-(3-methoxypropoxy)-2-oxo-1,2,5,6-tetrahydro-1,10-phenanthroline-3-carboxylic acid The title compound was obtained from (RS)-5-(tert-butyl)-1-cyclopropyl-9-methoxy-8-(3-methoxypropoxy)-2-oxo-1,2,5,6-tetrahydro-1,10-phenanthroline-3-carbonitrile as yellow solid in 29% yield according to general procedure VII.

MS m/e: [M+H]+ 457.1

$^1$HNMR (400 MHz, CDCl$_3$): 14.66 (s, 1H), 8.34 (s, 1H), 6.97 (s, 1H), 4.25-4.14 (m, 2H), 3.95 (s, 3H), 3.87-3.80 (m, 1H), 3.60 (t, J=6.0 MHz, 2H), 3.38 (s, 3H), 3.12 (dd, J=16.0, 6.8 MHz, 1H), 3.01 (d, J=16.0 MHz, 1H), 2.54 (d, J=6.4 MHz, 1H), 2.20-2.14 (m, 2H), 1.48-1.41 (m, 1H), 0.81-0.73 (m, 2H), 0.70 (s, 9H), 0.22-0.17 (m, 1H).

Comparative Examples of Formula XXII

Example 801

(RS)-5-(tert-Butyl)-9-methoxy-8-(3-methoxypropoxy)-2-oxo-1,5-dihydro-2H-chromeno[4,3-b]pyridine-3-carboxylic acid a) 4-Methoxy-3-(3-methoxypropoxy)phenyl acetate To a solution of 4-methoxy-3-(3-methoxypropoxy)phenol (23 g, 65 mmol) and N,N-diisopropylethylamine (28.3 mL, 2.5 eq., 163 mmol) in chloroform (285 mL) was slowly added acetic anhydride (7.4 mL, 1.2 eq., 78 mmol) at 0° C. The reaction mixture was stirred at room temperature for 6 hours. The mixture was subsequently poured into water (100 mL) and extracted with three 200-mL portions of dichloromethane. The combined organic layers were washed with brine, dried over anhydrous sodium sulfate, filtered and concentrated under reduced pressure. The residue was purified by silica gel chromatography (eluted with petroleum ether: ethyl acetate=20:1-15:1) to afford the title compound (15 g, 53.1 mmol, 90% purity, 82% yield) as brown solid.

MS m/e: [M+H]+: 255.2 b) 1-(2-Hydroxy-5-methoxy-4-(3-methoxypropoxy)phenyl)ethan-1-one

To a solution of 4-methoxy-3-(3-methoxypropoxy)phenyl acetate (10.0 g, 39.3 mmol) in boron trifluoride etherate (50 mL, 0.41 mol) was added acetic acid (35 mL). The mixture was stirred at 70° C. for 8 h. After cooling to room temperature, the mixture was diluted with water (500 mL) and extracted with three 400-mL portions of ethyl acetate. The combined organic layers were washed with brine, dried over anhydrous sodium sulfate, filtered, and concentrated under reduced pressure. The residue was purified by silica gel chromatography to afford the title compound (9.0 g, 32 mmol, 90% purity, 81% yield) as yellow solid.

MS m/e: [M+H]$^+$ 255.0 c) (RS)-2-(tert-Butyl)-6-methoxy-7-(3-methoxypropoxy)chroman-4-one

The title compound was obtained from 1-(2-hydroxy-5-methoxy-4-(3-methoxypropoxy)phenyl)ethan-1-one as yellow solid in 43% yield according to general procedure II at 50° C.

MS m/e: [M+H]$^+$ 323.0 d) (RS)-2-(tert-Butyl)-3-((dimethylamino)methylene)-6-methoxy-7-(3-methoxypropoxy)chroman-4-one The title compound was obtained from (RS)-2-(tert-butyl)-6-methoxy-7-(3-methoxypropoxy)chroman-4-one as yellow oil in 80% yield according to general procedure III at a reaction temperature of 120° C.

MS m/e: [M+H]$^+$ 378.0 e) (RS)-5-(tert-Butyl)-9-methoxy-8-(3-methoxypropoxy)-2-oxo-1,5-dihydro-2H-chromeno[4,3-b]pyridine-3-carbonitrile The title compound was obtained from (RS)-2-(tert-butyl)-3-((dimethylamino)methylene)-6-methoxy-7-(3-methoxypropoxy)chroman-4-one as yellow solid in 61% yield according to general procedure IV at 120° C.

MS m/e: [M+H]$^+$ 399.2 f) (RS)-5-(tert-Butyl)-9-methoxy-8-(3-methoxypropoxy)-2-oxo-1,5-dihydro-2H-chromeno[4,3-b]pyridine-3-carboxylic acid The title compound was obtained from (RS)-5-(tert-butyl)-9-methoxy-8-(3-methoxypropoxy)-2-oxo-1,5-dihydro-2H-chromeno[4,3-b]pyridine-3-carbonitrile as yellow solid in 22% yield according to general procedure VII.

MS m/e: [M+H]$^+$ 418.1

$^1$H NMR (400 MHz, CDCl$_3$): 8.23 (s, 1H), 7.05 (s, 1H), 6.55 (s, 1H), 4.90 (s, 1H), 4.18-4.15 (m, 2H), 3.91 (s, 3H), 3.60-3.56 (m, 2H), 3.37 (s, 3H), 2.16-2.13 (m, 2H), 0.92 (s, 9H).

Example 802

(RS)-5-(tert-Butyl)-1-cyclopropyl-9-methoxy-8-(3-methoxypropoxy)-2-oxo-1,5-dihydro-2H-chromeno[4,3-b]pyridine-3-carboxylic acid a) (RS)-2-(tert-Butyl)-N-cyclopropyl-6-methoxy-7-(3-methoxypropoxy)chroman-4-imine To a solution of (RS)-2-(tert-butyl)-6-methoxy-7-(3-methoxypropoxy)chroman-4-one (100 mg, 0.310 mmol) in dichloromethane (2 mL) was added cyclopropylamine (23.0 mg, 1.3 eq., 0.403 mmol) and triethylamine (94.2 mg, 3.0 eq., 0.931 mmol) at 0° C. The mixture was subsequently slowly treated with titanium tetrachloride (1 M solution in dichloromethane, 186 μL, 0.6 eq., 0.186 mmol) at 0° C.

After completed addition the mixture was allowed to warm to room temperature and stirred for 2 hours. The mixture was poured into saturated aqueous sodium bicarbonate solution (10 mL) and extracted with three 5-mL portions of dichloromethane.

The combined organic layers were washed with brine (10 mL), dried over anhydrous sodium sulfate, filtered and concentrated in vacuo to give the title compound (100 mg, 257 μmol, 93% purity, 83% yield) as a yellow oil.

MS m/e: [M+H]$^+$ 362.2 b) (RS)-Ethyl 5-(tert-butyl)-1-cyclopropyl-9-methoxy-8-(3-methoxypropoxy)-2-oxo-1,5-dihydro-2H-chromeno[4,3-b]pyridine-3-carboxylate To a solution of (RS)-2-(tert-butyl)-N-cyclopropyl-6-methoxy-7-(3-methoxypropoxy)chroman-4-imine (100 mg, 257 μmol) in phenoxybenzene (3 mL) was added diethyl ethoxymethylenemalonate (120 mg, 2.15 eq., 553 μmol). The mixture was stirred for 3 hours at 230° C. The mixture as allowed to cool to room temperature and directly purified by silica gel chromatography (eluted with 10-100% ethyl acetate in petroleum ether) to give the title compound (38 mg, 74 μmol, 95% purity, 29% yield) as yellow solid.

MS m/e: [M+H]$^+$ 486.0 c) (RS)-5-(tert-Butyl)-1-cyclopropyl-9-methoxy-8-(3-methoxypropoxy)-2-oxo-1,5-dihydro-2H-chromeno[4,3-b]pyridine-3-carboxylic acid To a solution of (RS)-ethyl 5-(tert-butyl)-1-cyclopropyl-9-methoxy-8-(3-methoxypropoxy)-2-oxo-1,5-dihydro-2H-chromeno[4,3-b]pyridine-3-carboxylate (38 mg, 74 μmol) in tetrahydrofuran (0.35 mL) and lithium hydroxide (9.4 mg, 5.3 eq., 0.39 mmol) in water (0.8 mL). After stirring at 30° C. for 2 hours, the mixture was cooled to room temperature and acidified with 1 M aqueous hydrogen chloride solution to pH=2. The mixture was extracted with three 10-mL portions of dichloromethane. The combined organic layers were washed with brine, dried over sodium sulfate, filtered and concentrated under reduced pressure. The residue was purified by reversed phase HPLC (C$_{18}$ column, eluted with acetonitrile: 0.02% aqueous ammonium bicarbonate solution=5% to 95%) to give the title compound (12 mg, 25 μmol, 95% purity, 34% yield) as yellow solid.

MS m/e: [M+H]$^+$ 458.1

HNMR (400 MHz, CD$_3$OD): 8.12 (s, 1H), 7.56 (s, 1H), 6.70 (s, 1H), 4.85 (s, 1H), 4.18-4.11 (m, 2H), 3.84 (s, 3H), 3.70-3.68 (m, 1H), 3.60 (t, J=6.4 MHz, 2H), 3.36 (s, 3H), 2.10-2.07 (m, 2H), 1.48-1.44 (m, 1H), 1.11-1.07 (m, 1H), 0.83 (s, 9H), 0.71-0.697 (m, 1H), 0.40-0.38 (m, 1H).

Notwithstanding the appended claims, the disclosure set forth herein is also defined by the following clauses:

1. A compound of formula (I)

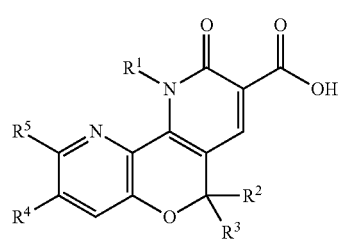

(I)

or a pharmaceutically acceptable salt, a racemic mixture, a corresponding enantiomer or, if applicable, a corresponding diastereomer thereof, wherein $R^1$ is selected from the group consisting of hydrogen, a linear or branched $C_1$ to $C_6$ alkyl, a $C_3$ to $C_5$ cycloalkyl, a $C_1$-$C_3$-alkyl-$C_3$-$C_5$-cycloalkyl, and a cyclic ether comprising 4 to 5 ring atoms,
- wherein said $C_1$ to $C_6$ linear or branched alkyl is optionally substituted with one or more substituents selected from the group consisting of fluoro, chloro, hydroxy and $C_1$ to $C_3$ alkoxy,
- wherein said $C_3$ to $C_5$ cycloalkyl and said $C_1$-$C_3$-alkyl-$C_3$-$C_5$-cycloalkyl may optionally be substituted with one or more substituents selected from the group consisting of fluoro, chloro, $C_1$ to $C_3$ alkyl, hydroxy and $C_1$ to $C_3$ alkoxy, and
- wherein said cyclic ether comprising 4 to 5 ring atoms is optionally substituted with one or more substituents selected from the group consisting of fluoro, chloro, $C_1$ to $C_3$ alkyl, hydroxy and $C_1$ to $C_3$ alkoxy;

$R^2$ is selected from the group consisting of hydrogen and methyl;

$R^3$ is selected from the group consisting of hydrogen, a linear or branched $C_1$ to $C_6$ alkyl, a $C_3$ to $C_6$ cycloalkyl, a 4-6-membered heterocycloalkyl, $C_1$-$C_3$-alkyl-$C_3$-$C_6$-cycloalkyl and a $C_1$-$C_3$-alkyl-4-6-membered heterocycloalkyl,
- wherein said linear or branched $C_1$ to $C_6$ alkyl may optionally be substituted with one or more substituents selected from the group consisting of fluoro, chloro, cyano, hydroxy and $C_1$ to $C_3$ alkoxy; and
- wherein said $C_3$ to $C_6$ cycloalkyl, said 4-6-membered heterocycloalkyl, said $C_1$-$C_3$-alkyl-$C_3$-$C_6$-cycloalkyl and said $C_1$-$C_3$-alkyl-4-6-membered heterocycloalkyl may optionally be substituted with one or more substituents selected from the group consisting of fluoro, chloro, cyano, $C_1$ to $C_3$ alkyl, hydroxy and $C_1$ to $C_3$ alkoxy; or $R^2$ and $R^3$ may form together a 4 to 6 membered cycloalkyl or heterocycloalkyl, which may optionally be substituted with one or more substituents selected from the group consisting of fluoro, chloro, cyano, $C_1$ to $C_3$ alkyl, hydroxy and $C_1$ to $C_3$ alkoxy $R^4$ is selected from the group consisting of a linear or branched $C_1$ to $C_6$ alkoxy, an alkoxyalkoxyl group having up to 6 carbon atoms, a $C_1$-$C_3$ alkoxy $C_3$-$C_8$ cycloalkyl, a 4-7-membered heterocycloalkyl, a $C_1$-$C_6$ alkyl 4-7 membered monocyclic heterocycloalkyl, a $C_2$ to $C_8$ alkenyl and a $C_2$ to $C_8$ alkynyl and
- wherein said $C_1$ to $C_6$ alkoxy, said alkenyl and said alkynyl may optionally be substituted with one or more substituents selected from the group consisting of hydroxy, chloro and fluoro, a 3 to 6 membered monocyclic cycloalkyl group, a 4 to 6 membered monocyclic heterocycloalkyl group, a spirocyclic 3 to 7 membered monocyclic cycloalkyl group and a spirocyclic 3 to 7 membered monocyclic heterocycloalkyl group; and
- wherein said $C_1$-$C_3$ alkoxy $C_3$-$C_8$ cycloalkyl, said 4-7-membered heterocycloalkyl, and said $C_1$-$C_6$ alkyl 4-7 membered monocyclic heterocycloalkyl may optionally be substituted with one or more substituents selected from the group consisting of hydroxy, chloro, fluoro, and $C_1$ to $C_3$ alkyl and $C_1$ to $C_3$ alkoxy;

$R^5$ is selected from the group consisting of fluoro, chloro, bromo, cyano, $C_1$ to $C_5$ alkoxy, $C_1$ to $C_5$ alkyl, alkoxyalkyl having up to 6 carbon atoms, 4 to 6 membered heterocycloalkyl, 3 to 6 membered cycloalkyl, 5-membered heteroaryl, and $NR^6R^7$
- wherein said $C_1$ to $C_5$ alkoxy and said alkoxyalkyl having up to 6 carbon atoms may optionally be substituted with one or more substituents selected from the group consisting of fluoro, chloro, hydroxy, $C_1$ to $C_3$ alkoxy, and wherein said $C_1$ to $C_5$ alkyl is optionally substituted with one or more substituents selected from the group consisting of fluoro, chloro, $C_1$ to $C_3$ alkoxy, 3 to 6 membered cycloalkyl and 4 to 6 membered heterocycloalkyl, and
- wherein said 4 to 6 membered heterocycloalkyl is optionally substituted with one or more substituents selected from the group consisting of fluoro, chloro, hydroxy, $C_1$ to $C_3$ alkoxy, and $C_1$ to $C_3$ alkyl, wherein said 3 to 6 membered cycloalkyl is optionally substituted one or more substituents selected from the group consisting of with fluoro, chloro, hydroxy, $C_1$ to $C_3$ alkoxy, and $C_1$ to $C_3$ alkyl;
- wherein $R^6$ and $R^7$ are independently selected from the group consisting of hydrogen, methyl and ethyl, and
- wherein said 5-membered heteroaryl is optionally substituted with one or more substituents selected from the group consisting of fluoro, chloro, hydroxy, $C_1$ to $C_3$ alkoxy, and $C_1$ to $C_3$ alkyl.

2. Compound according to clause 1, wherein $R^1$ is selected from the group consisting of methyl, ethyl, 2,2-difluoroethyl and cyclopropyl.

3. Compound according any of the preceding clauses, wherein $R^2$ is hydrogen.

4. Compound according to any of the preceding clauses, wherein $R^3$ is selected from the group consisting of isopropyl, sec-butyl, (1-methyl)cyclopropyl and tert-butyl.

5. Compound according to any of the preceding clauses, wherein $R^3$ is isopropyl or tert-butyl.

6. Compound according to any of clauses 1 to 3, wherein $R^2$ and $R^3$ form together a 4 to 6 membered cycloalkyl or a 4 to 6 membered heterocycloalkyl.

7. Compound according to clause 6, wherein $R^2$ and $R^3$ form together a cyclopentyl ring.

8. Compound according to any of the preceding clauses, wherein $R^4$ is selected from the group consisting of cyclopropylmethoxy, 2-cyclopropylethoxy and —O(CH$_2$)$_3$OCH$_3$.

9. Compound according to any of the preceding clauses, wherein $R^4$ is —O(CH$_2$)$_3$OCH$_3$.

10. Compound according to any of the preceding clauses, wherein $R^5$ is selected from the group consisting of methoxy, ethoxy, methyl, ethyl, methoxymethyl and cyclopropyl.

11. Compound according to any of the preceding clauses, wherein said compound is selected from the group of compounds 501 to 511

| No. | Structure |
|---|---|
| 501 | 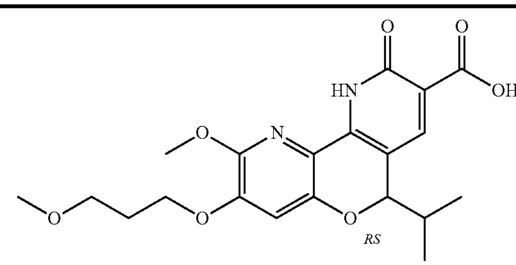 |

| No. | Structure |
|---|---|
| 502 | 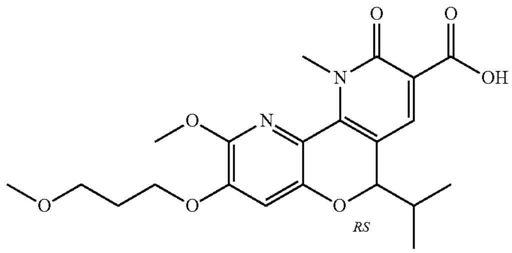 [SMILES: COCCCOc1cc2c(nc1OC)-c1c(cc(C(=O)O)c(=O)n1C)C(C(C)C)O2] |
| 503 | 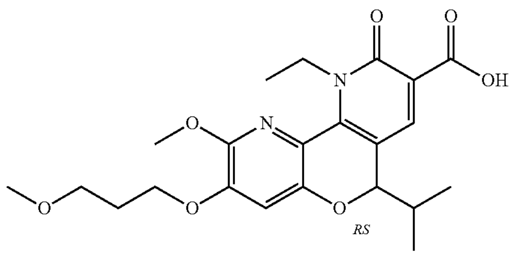 [SMILES: CCn1c2c(cc(C(=O)O)c1=O)C(C(C)C)Oc1cc(OCCCOC)c(OC)nc1-2] |
| 504 | 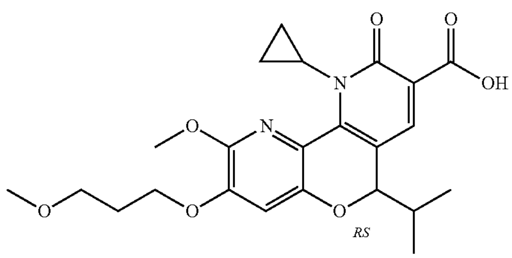 [SMILES: COCCCOc1cc2c(nc1OC)-c1c(cc(C(=O)O)c(=O)n1C1CC1)C(C(C)C)O2] |
| 505 | 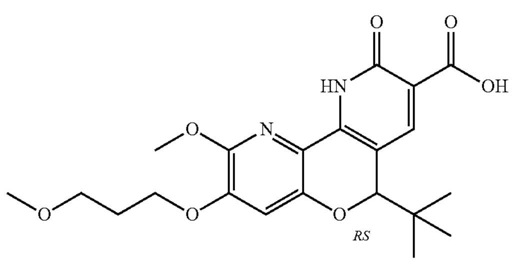 [SMILES: COCCCOc1cc2c(nc1OC)-c1[nH]c(=O)c(C(=O)O)cc1C(C(C)(C)C)O2] |
| 506 | 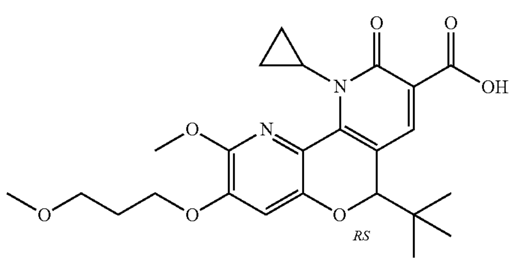 [SMILES: COCCCOc1cc2c(nc1OC)-c1c(cc(C(=O)O)c(=O)n1C1CC1)C(C(C)(C)C)O2] |
| 507 | 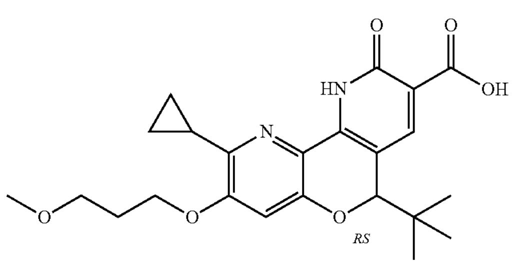 [SMILES: COCCCOc1cc2c(nc1C1CC1)-c1[nH]c(=O)c(C(=O)O)cc1C(C(C)(C)C)O2] |
| 508 | |
| 509 | |
| 510 | |
| 511 | |

12. Compound according to clause 11, wherein said compound is (RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (RS)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid, in particular with (S)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (S)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid.

13. Pharmaceutical composition comprising a compound according to any of the preceding clauses as a therapeutically active substance and a pharmaceutically acceptable carrier and/or adjuvant.

14. Pharmaceutical composition according to claim 13, comprising at least one compound selected from the group of compounds 501 to 511

| No. | Structure |
|-----|-----------|
| 501 | |
| 502 | |
| 503 | |
| 504 | |
| 505 | |
| 506 | 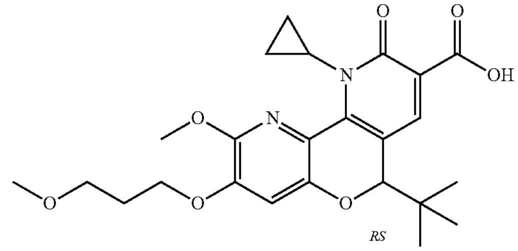 [SMILES: COCCCOc1cc2c(nc1OC)-c1c(cc(C(=O)O)c(=O)n1C1CC1)C(C(C)(C)C)O2] |
| 507 | 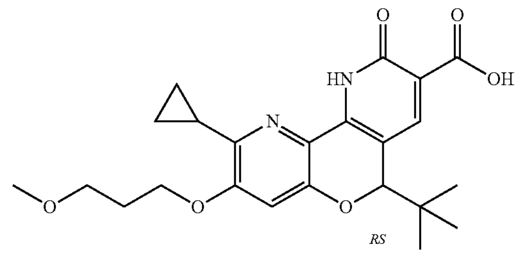 [SMILES: COCCCOc1cc2c(nc1C1CC1)-c1[nH]c(=O)c(C(=O)O)cc1C(C(C)(C)C)O2] |
| 508 | 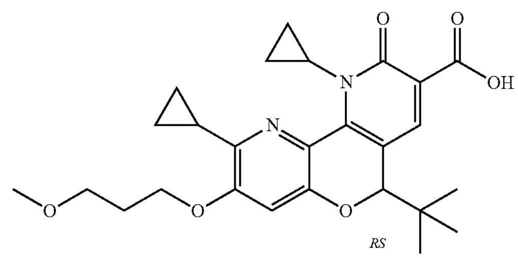 [SMILES: COCCCOc1cc2c(nc1C1CC1)-c1c(cc(C(=O)O)c(=O)n1C1CC1)C(C(C)(C)C)O2] |
| 509 | 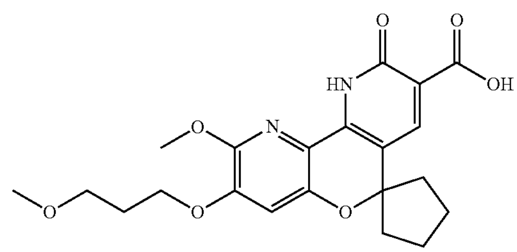 [SMILES: COCCCOc1cc2c(nc1OC)-c1[nH]c(=O)c(C(=O)O)cc1C1(CCCC1)O2] |
| 510 | 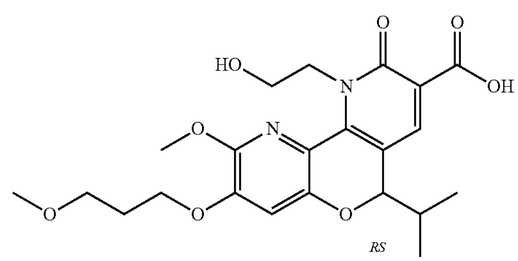 [SMILES: COCCCOc1cc2c(nc1OC)-c1c(cc(C(=O)O)c(=O)n1CCO)C(C(C)C)O2] |
| 511 | 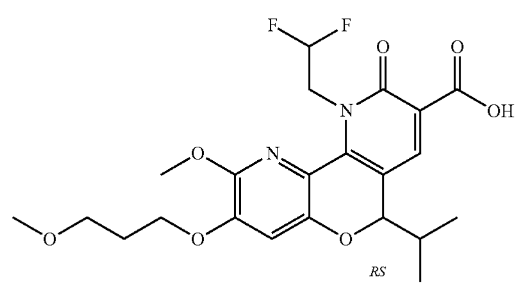 [SMILES: COCCCOc1cc2c(nc1OC)-c1c(cc(C(=O)O)c(=O)n1CC(F)F)C(C(C)C)O2] |

15. Compound according to any of claims 1 to 12 or pharmaceutical composition according to any of clauses 13 to 14 for use as a medicament.
16. Compound according to any of claims 1 to 12 or pharmaceutical composition according to any of clauses 13 to 15 for use in the treatment or prevention of a disease which benefits from PAPD5 inhibition selected from the group consisting of a telomere biology disorder, poikiloderma with neutropenia and hepatitis B.
17. Compound according to any of claims 1 to 12 or pharmaceutical composition according to any of clauses 13 to 16, wherein the telomere biology disorder is selected from the group consisting of dyskeratosis congenita, idiopathic pulmonary fibrosis (IPF), liver cirrhosis, aplastic anemia, bone marrow failure syndrome, immunodeficiencies, neurodevelopmental disorders, growth retardation linked to telomere biology diseases, and age-related diseases and premature aging caused by telomere shortening, preferably dyskeratosis congenita, idiopathic pulmonary fibrosis (IPF) and liver cirrhosis and wherein the dyskeratosis congenita is preferably selected from the group consisting of Høyeraal-Hreidarsson syndrome (HHS), Revesz syndrome (RS) and Coats plus syndrome (CPS).
18. Compound according to any of claims 1 to 12 or pharmaceutical composition according to any of clauses 13 to 16 for use in the treatment of hepatitis B.
19. Compound according to any of claims 1 to 12 or pharmaceutical composition according to any of clauses 13 to 16 for use in the treatment of poikiloderma with neutropenia.
20. A method for treating a disease which benefits from PAPD5 inhibition selected from the group consisting of TBDs poikiloderma with neutropenia and hepatitis B comprising administering a compound of formula (I) according to any of claims 1 to 12 or a pharmaceutically acceptable salt, a racemic mixture, a corresponding enantiomer or, if applicable, a corresponding diastereomer thereof or a pharmaceutical composition according to any of claims 13 to 15 to a patient having said disease in an amount effective to treat the disease.
21. Method for preparing the compound of formula I, the method comprising the step of reacting a compound of formula II-a

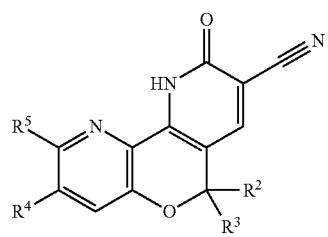

(II-a)

in the presence of
 i. a base and R$^1$-LG or
 ii. R$^1$—B(OH)$_2$ or R$^1$-BF$_3$M, a copper-salt, amine,
wherein
 R$^1$ is selected from the group consisting of a linear or branched C$_1$ to C$_6$ alkyl, a C$_3$ to C$_5$ cycloalkyl, a C$_1$-C$_3$-alkyl-C$_3$-C$_5$-cycloalkyl, and a cyclic ether comprising 4 to 5 ring atoms,
  wherein said C$_1$ to C$_6$ linear or branched alkyl is optionally substituted with one or more substituents selected from the group consisting of fluoro, chloro, hydroxy and C$_1$ to C$_3$ alkoxy,
 wherein said C$_3$ to C$_5$ cycloalkyl and said C$_1$-C$_3$-alkyl-C$_3$-C$_5$-cycloalkyl may optionally be substituted with one or more substituents selected from the group consisting of fluoro, chloro, C$_1$ to C$_3$ alkyl, hydroxy and C$_1$ to C$_3$ alkoxy, and
 wherein said cyclic ether comprising 4 to 5 ring atoms is optionally substituted with one or more substituents selected from the group consisting of fluoro, chloro, C$_1$ to C$_3$ alkyl, hydroxy and C$_1$ to C$_3$ alkoxy;
and LG is a leaving group;
to a compound of formula

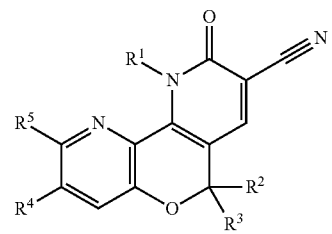

(II-b)

22. Method according to clause 21, the method comprising the step of hydrolyzing the compound of formula II-a or II-b

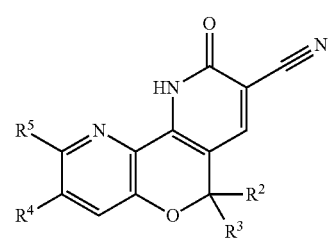

(II-a)

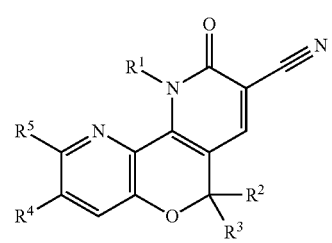

(II-b)

in the presence of an acid or a base
to compound of formula (I)

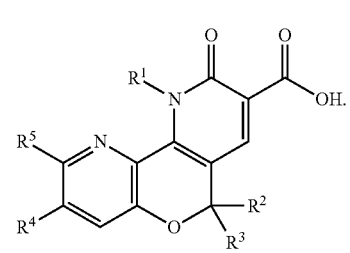

(I)

23. Intermediate selected from the group consisting of

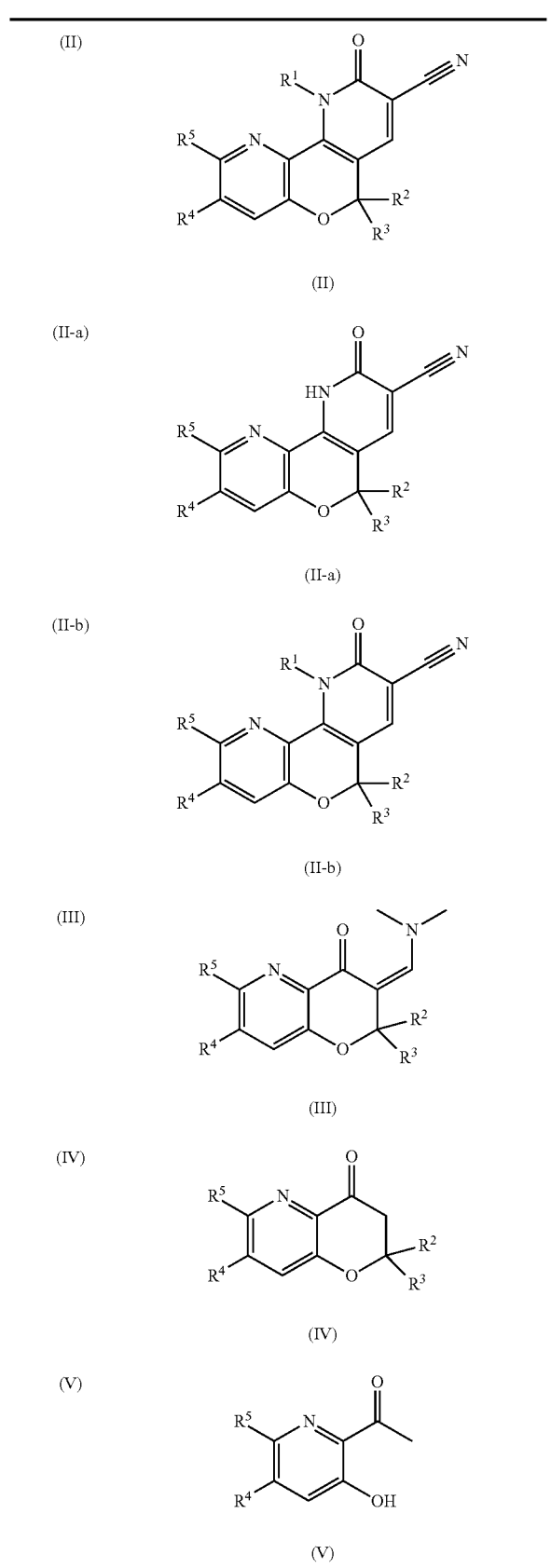

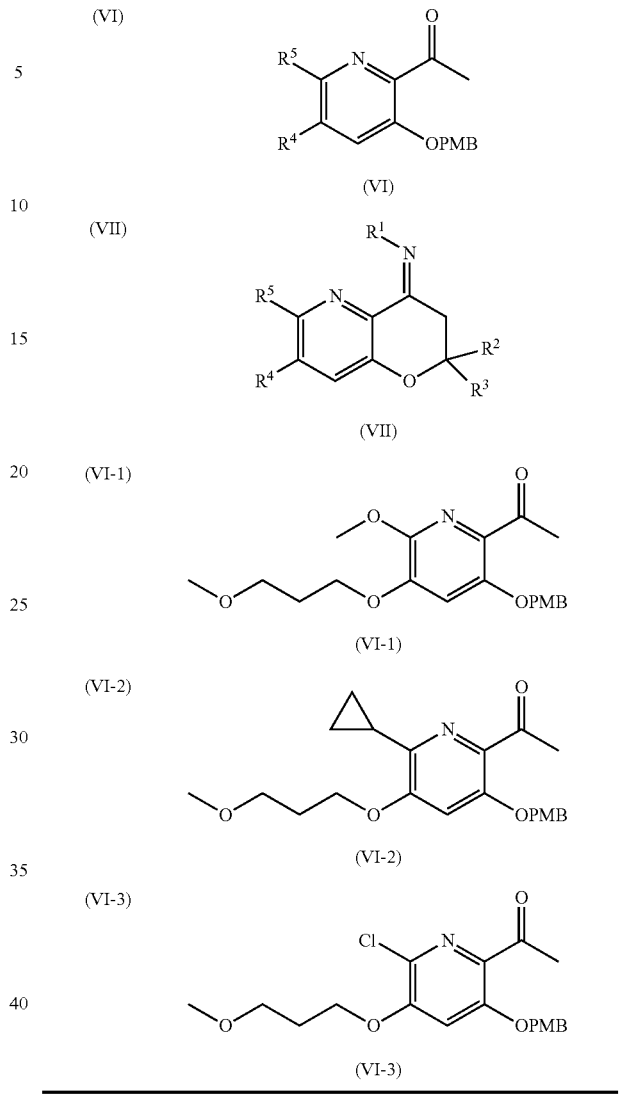

wherein $R^1$, $R^2$, $R^3$, $R^4$ and $R^5$ have the same definition as in clause 1.

LIST OF ABBREVIATIONS

BMF: Bone marrow failure
CPS: Coats plus syndrome
DC: Dyskeratosis congenita
DDR: DNA damage response
DKC1: Dyskerin pseudouridine synthase 1 (dyskerin)
DMSO: Dimethyl sulfoxide
DNA: Deoxyribonucleic acid
ELISA: Enzyme-linked immunosorbent assay
FBS: Fetal bovine serum
GAR1: GAR1 ribonucleoprotein
HBV: Hepatitis B virus
HBsAg: Hepatitis B surface antigen
HHS: Høyeraal-Hreidarsson syndrome
hTERT: Human telomerase reverse transcriptase
kb: Kilobase
IPF: Idiopathic pulmonary fibrosis
iPSCs: Induced pluripotent stem cells
KO: Knock out LG: Leaving group
NBS: N-Bromosuccinimide
NHP2: NHP2 Ribonucleoprotein
NOP10: NOP10 Ribonucleoprotein
PAPD5: PAP-associated domain-containing protein 5
PAPD7: PAP-associated domain-containing protein 7
PARN: Poly(A)-specific ribonuclease
PBS: Phosphate-buffered saline
PMB: para-Methoxybenzyl
PN: Poikiloderma with neutropenia
RACE: RNA ligation-mediated rapid amplification of cDNA ends
RNA: Ribonucleic acid
RNP: Ribonucleoprotein
RS: Revesz syndrome
RT: Room temperature
TBD: Telomere biology disorder
TCAB: Telomerase Cajal body protein
TERC: Telomerase RNA component
TRF: Telomere restriction fragment
USB1: U6 SnRNA biogenesis phosphodiesterase 1
WT: Wild type
ZCCHC8: Zinc finger CCHC-type containing 8

The invention claimed is:

1. A compound of formula (I)

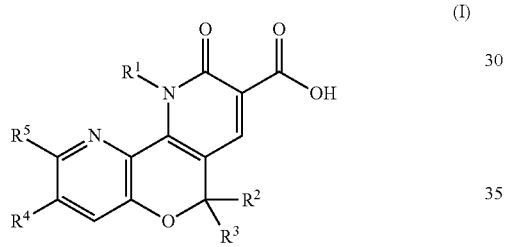

or a pharmaceutically acceptable salt, a racemic mixture, a corresponding enantiomer or, if applicable, a corresponding diastereomer thereof,
wherein
$R^1$ is selected from the group consisting of hydrogen, a linear or branched $C_1$ to $C_6$ alkyl, a $C_3$ to $C_5$ cycloalkyl, a $C_1$-$C_3$-alkyl-$C_3$-$C_5$-cycloalkyl, and a cyclic ether comprising 4 to 5 ring atoms,
wherein said $C_1$ to $C_6$ linear or branched alkyl is optionally substituted with one or more substituents selected from the group consisting of fluoro, chloro, hydroxy and $C_1$ to $C_3$ alkoxy,
wherein said $C_3$ to $C_5$ cycloalkyl and said $C_1$-$C_3$-alkyl-$C_3$-$C_5$-cycloalkyl may optionally be substituted with one or more substituents selected from the group consisting of fluoro, chloro, $C_1$ to $C_3$ alkyl, hydroxy and $C_1$ to $C_3$ alkoxy, and
wherein said cyclic ether comprising 4 to 5 ring atoms is optionally substituted with one or more substituents selected from the group consisting of fluoro, chloro, $C_1$ to $C_3$ alkyl, hydroxy and $C_1$ to $C_3$ alkoxy;
$R^2$ is selected from the group consisting of hydrogen and methyl;
$R^3$ is selected from the group consisting of hydrogen, a linear or branched $C_1$ to $C_6$ alkyl, a $C_3$ to $C_6$ cycloalkyl, a 4-6-membered heterocycloalkyl, $C_1$-$C_3$-alkyl-$C_3$-$C_6$-cycloalkyl and a $C_1$-$C_3$-alkyl-4-6-membered heterocycloalkyl,
wherein said linear or branched $C_1$ to $C_6$ alkyl may optionally be substituted with one or more substituents selected from the group consisting of fluoro, chloro, cyano, hydroxy and $C_1$ to $C_3$ alkoxy, and
wherein said $C_3$ to $C_6$ cycloalkyl, said 4-6-membered heterocycloalkyl, said $C_1$-$C_3$-alkyl-$C_3$-$C_6$-cycloalkyl and said $C_1$-$C_3$-alkyl-4-6-membered heterocycloalkyl may optionally be substituted with one or more substituents selected from the group consisting of fluoro, chloro, cyano, $C_1$ to $C_3$ alkyl, hydroxy and $C_1$ to $C_3$ alkoxy; or
$R^2$ and $R^3$ may form together a 4 to 6 membered cycloalkyl or heterocycloalkyl, which may optionally be substituted with one or more substituents selected from the group consisting of fluoro, chloro, cyano, $C_1$ to $C_3$ alkyl, hydroxy and $C_1$ to $C_3$ alkoxy;
$R^4$ is selected from the group consisting of a linear or branched $C_1$ to $C_6$ alkoxy, an alkoxyalkoxyl group having up to 6 carbon atoms, a $C_1$-$C_3$ alkoxy $C_3$-$C_8$ cycloalkyl, a 4-7-membered heterocycloalkyl, a $C_1$-$C_6$ alkyl 4-7 membered monocyclic heterocycloalkyl, a $C_2$ to $C_8$ alkenyl and a $C_2$ to $C_8$ alkynyl,
wherein said $C_1$ to $C_6$ alkoxy, said alkenyl and said alkynyl may optionally be substituted with one or more substituents selected from the group consisting of hydroxy, chloro and fluoro, a 3 to 6 membered monocyclic cycloalkyl group, a 4 to 6 membered monocyclic heterocycloalkyl group, a spirocyclic 3 to 7 membered monocyclic cycloalkyl group and a spirocyclic 3 to 7 membered monocyclic heterocycloalkyl group, and
wherein said $C_1$-$C_3$ alkoxy $C_3$-$C_8$ cycloalkyl, said 4-7-membered heterocycloalkyl, and said $C_1$-$C_6$ alkyl 4-7 membered monocyclic heterocycloalkyl may optionally be substituted with one or more substituents selected from the group consisting of hydroxy, chloro, fluoro, and $C_1$ to $C_3$ alkyl and $C_1$ to $C_3$ alkoxy; and
$R^5$ is selected from the group consisting of fluoro, chloro, bromo, cyano, $C_1$ to $C_5$ alkoxy, $C_1$ to $C_5$ alkyl, alkoxyalkyl having up to 6 carbon atoms, 4 to 6 membered heterocycloalkyl, 3 to 6 membered cycloalkyl, 5-membered heteroaryl, and $NR^6R^7$,
wherein said $C_1$ to $C_5$ alkoxy and said alkoxyalkyl having up to 6 carbon atoms may optionally be substituted from the group consisting of fluoro, chloro, hydroxy, $C_1$ to $C_3$ alkoxy,
wherein said $C_1$ to $C_5$ alkyl is optionally substituted with one or more substituents selected from the group consisting of fluoro, chloro, $C_1$ to $C_3$ alkoxy, 3 to 6 membered cycloalkyl and 4 to 6 membered heterocycloalkyl,
wherein said 4 to 6 membered heterocycloalkyl is optionally substituted with one or more substituents selected from the group consisting of fluoro, chloro, hydroxy, $C_1$ to $C_3$ alkoxy, and $C_1$ to $C_3$ alkyl,
wherein said 3 to 6 membered cycloalkyl is optionally substituted one or more substituents selected from the group consisting of with fluoro, chloro, hydroxy, $C_1$ to $C_3$ alkoxy, and $C_1$ to $C_3$alkyl,
wherein $R^6$ and $R^7$ are independently selected from the group consisting of hydrogen, methyl and ethyl, and wherein said 5-membered heteroaryl is optionally substituted with one or more substituents selected from the group consisting of fluoro, chloro, hydroxy, $C_1$ to $C_3$ alkoxy, and $C_1$ to $C_3$ alkyl.

2. The compound according to claim 1, wherein $R^1$ is selected from the group consisting of methyl, ethyl, 2,2-difluoroethyl and cyclopropyl.

3. The compound according to claim 1, wherein $R^2$ is hydrogen.

4. The compound according to claim 1, wherein $R^3$ is selected from the group consisting of isopropyl, sec-butyl, (1-methyl)cyclopropyl and tert-butyl.

5. The compound according to claim 4, wherein $R^3$ is isopropyl or tert-butyl.

6. The compound according to claim 1, wherein $R^2$ and $R^3$ form together a 4 to 6 membered cycloalkyl or a 4 to 6 membered heterocycloalkyl.

7. The compound according to claim 6, wherein $R^2$ and $R^3$ form together a cyclopentyl ring.

8. The compound according to claim 1, wherein $R^4$ is selected from the group consisting of cyclopropylmethoxy, 2-cyclopropylethoxy and $-O(CH_2)_3OCH_3$.

9. The compound according to claim 8, wherein $R^4$ is $-O(CH_2)_3OCH_3$.

10. The compound according to claim 1, wherein $R^5$ is selected from the group consisting of methoxy, ethoxy, methyl, ethyl, methoxymethyl and cyclopropyl.

11. The compound according to claim 1, wherein said compound is selected from the group of compounds 501 to 511

| No. | Structure |
|-----|-----------|
| 501 | 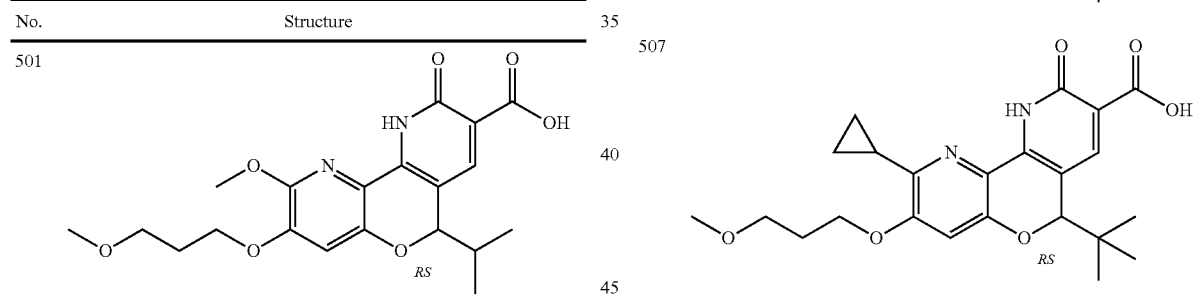 |
| 502 | 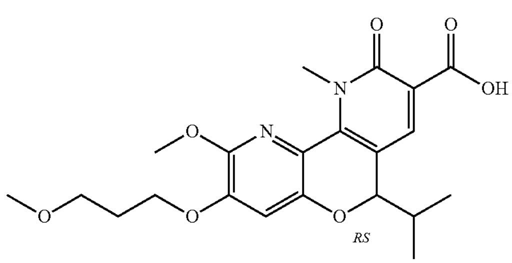 [SMILES: COCCCOc1cc2c(nc1OC)-c1c(cc(C(=O)O)c(=O)n1C)C(C(C)C)O2] |
| 503 | 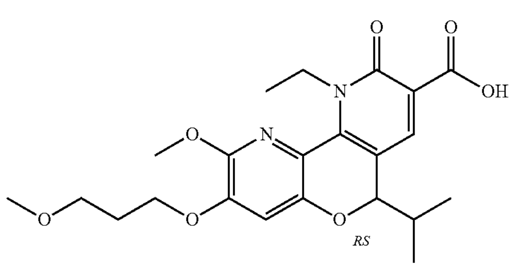 [SMILES: CCn1c2c(cc(C(=O)O)c1=O)C(C(C)C)Oc1cc(OCCCOC)c(OC)nc1-2] |

-continued

| No. | Structure |
|-----|-----------|
| 504 | 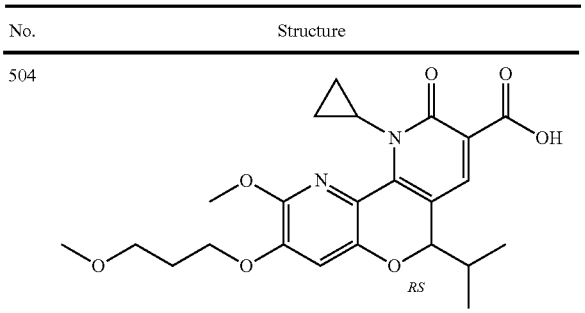 |
| 505 | 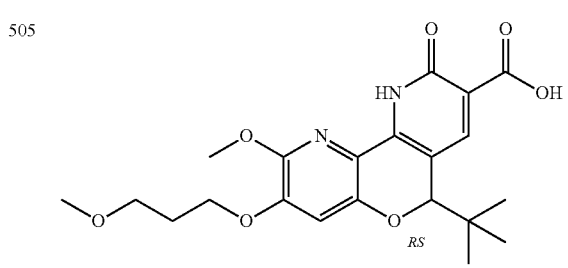 |
| 506 | 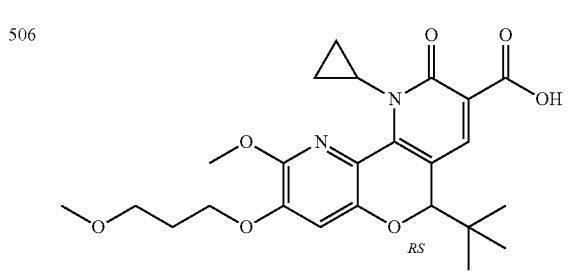 |
| 507 | 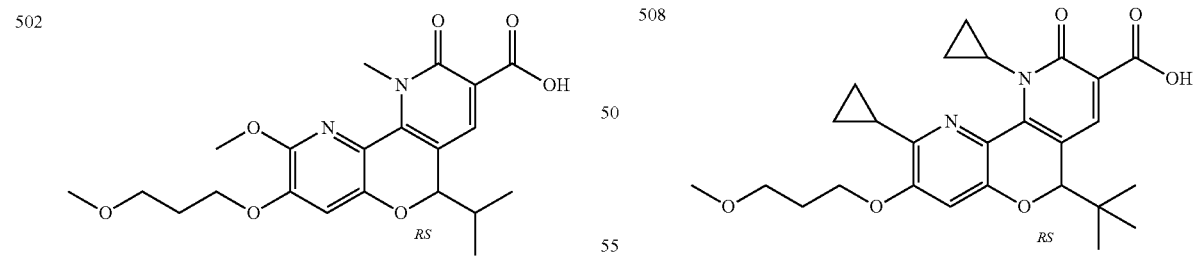 |
| 508 | 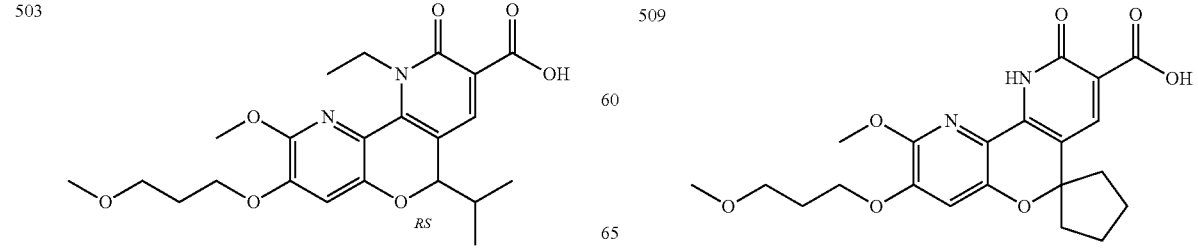 |
| 509 | 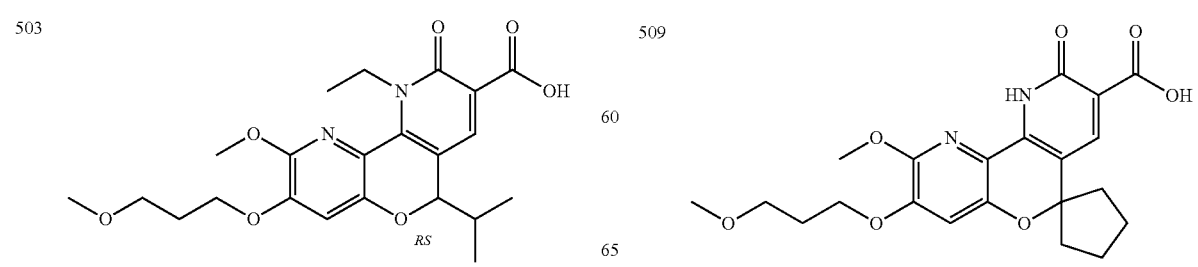 |

| No. | Structure |
|---|---|
| 510 | 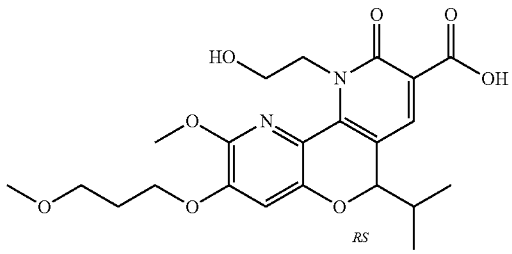 [SMILES: COCCCOc1cc2c(nc1OC)-c1c(cc(C(=O)O)c(=O)n1CCO)C(C(C)C)O2] |
| 511 | 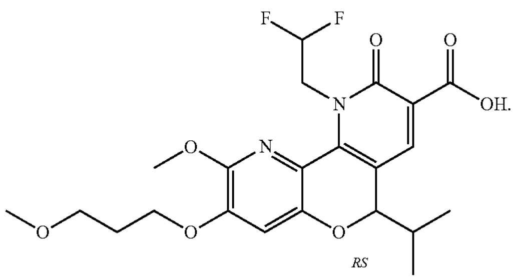 [SMILES: COCCCOc1cc2c(nc1OC)-c1c(cc(C(=O)O)c(=O)n1CC(F)F)C(C(C)C)O2] |

12. The compound according to claim 11, wherein said compound is (RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid or (RS)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid.

13. A pharmaceutical composition comprising:
   at least one compound according to claim 1 as a therapeutically active substance; and
   a pharmaceutically acceptable carrier and/or adjuvant.

14. The pharmaceutical composition according to claim 13, wherein said at least one compound is selected from the group of compounds 501 to 511

| No. | Structure |
|---|---|
| 501 | |
| 502 | |
| 503 | 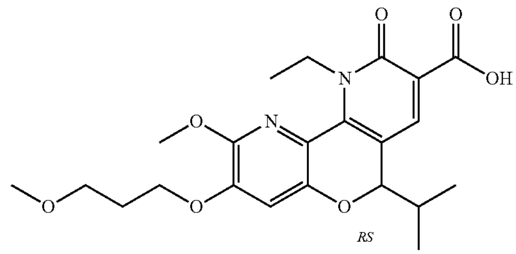 [SMILES: CCn1c2c(cc(C(=O)O)c1=O)C(C(C)C)Oc1cc(OCCCOC)c(OC)nc1-2] |
| 504 | 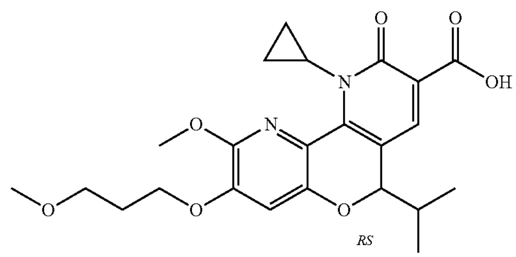 [SMILES: COCCCOc1cc2c(nc1OC)-c1c(cc(C(=O)O)c(=O)n1C1CC1)C(C(C)C)O2] |
| 505 | 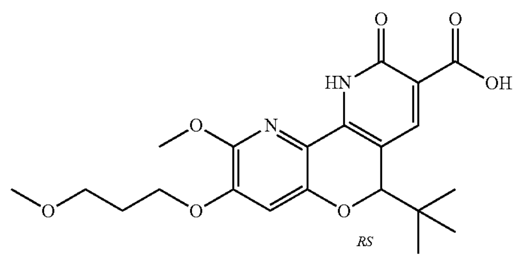 [SMILES: COCCCOc1cc2c(nc1OC)-c1[nH]c(=O)c(C(=O)O)cc1C(C(C)(C)C)O2] |
| 506 | 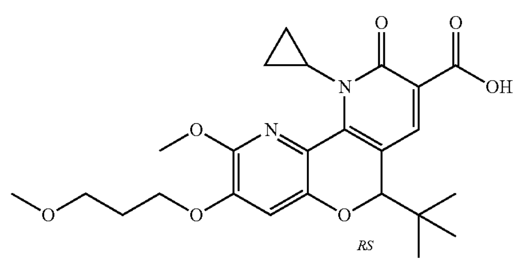 [SMILES: COCCCOc1cc2c(nc1OC)-c1c(cc(C(=O)O)c(=O)n1C1CC1)C(C(C)(C)C)O2] |
| 507 | 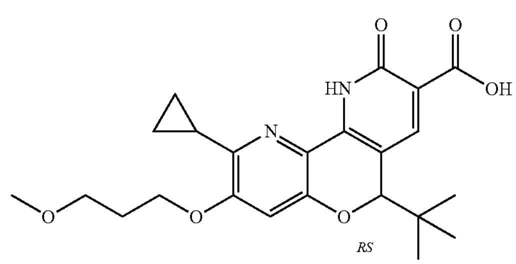 [SMILES: COCCCOc1cc2c(nc1C1CC1)-c1[nH]c(=O)c(C(=O)O)cc1C(C(C)(C)C)O2] |
| 508 | 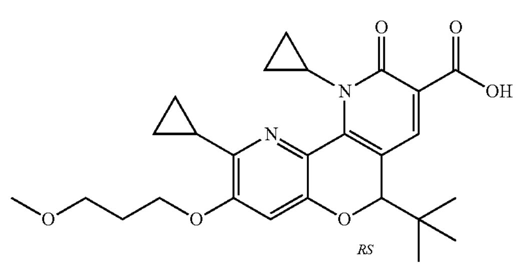 [SMILES: COCCCOc1cc2c(nc1C1CC1)-c1c(cc(C(=O)O)c(=O)n1C1CC1)C(C(C)(C)C)O2] |

67
-continued

| No. | Structure |
|-----|-----------|
| 509 | 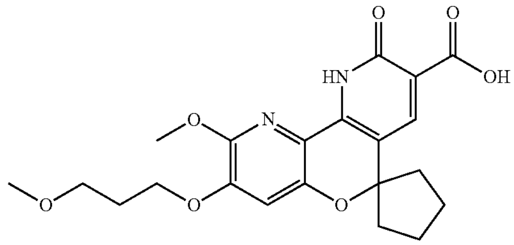 [SMILES: COCCCOc1cc2c(nc1OC)-c1[nH]c(=O)c(C(=O)O)cc1C1(CCCC1)O2] |
| 510 | 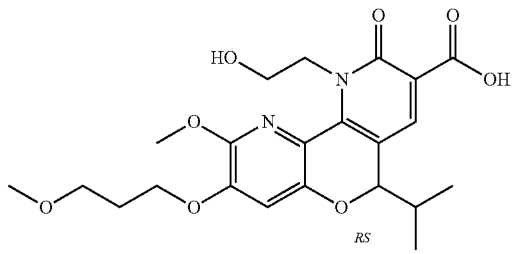 [SMILES: COCCCOc1cc2c(nc1OC)-c1c(cc(C(=O)O)c(=O)n1CCO)C(C(C)C)O2] |
| 511 | 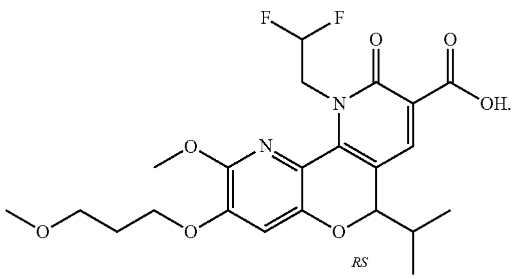 [SMILES: COCCCOc1cc2c(nc1OC)-c1c(cc(C(=O)O)c(=O)n1CC(F)F)C(C(C)C)O2] |

15. The pharmaceutical composition according to claim 14, wherein said at least one compound comprises (RS)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (RS)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid.

16. The pharmaceutical composition according to claim 15, wherein said at least one compound comprises (S)-6-(tert-butyl)-10-cyclopropyl-2-methoxy-3-(3-methoxypropoxy)-9-oxo-9,10-dihydro-6H-pyrano[3,2-b:4,5-b']dipyridine-8-carboxylic acid and (S)-10-cyclopropyl-6-isopropyl-2-methoxy-3-(3-methoxypropoxy)-9-oxo-9,10-dihydro-6H-pyrano[3,2-b:4,5-b']dipyridine-8-carboxylic acid.

17. The pharmaceutical composition according to claim 13 for use as a medicament.

18. The pharmaceutical composition according to claim 13 for use in the treatment of a disease which benefits from PAPD5 inhibition, the disease being selected from the group consisting of a telomere biology disorder, poikiloderma with neutropenia and hepatitis B.

19. The pharmaceutical composition according to claim 18, wherein the telomere biology disorder is selected from the group consisting of dyskeratosis congenita, idiopathic pulmonary fibrosis (IPF), liver cirrhosis, aplastic anemia, bone marrow failure syndrome, immunodeficiencies, neurodevelopmental disorders, growth retardation linked to telomere biology diseases, and age-related diseases and premature aging caused by telomere shortening.

20. The pharmaceutical composition according to claim 19, wherein the telomere biology disorder is selected from the group consisting of dyskeratosis congenita, idiopathic pulmonary fibrosis (IPF), and liver cirrhosis.

21. The pharmaceutical composition according to claim 20, wherein the dyskeratosis congenita is selected from the group consisting of Høyeraal-Hreidarsson syndrome (HHS), Revesz syndrome (RS) and Coats plus syndrome (CPS).

22. The pharmaceutical composition according to claim 18 for use in the treatment of hepatitis B.

23. The pharmaceutical composition according to claim 18 for use in the treatment of poikiloderma with neutropenia.

24. A method for preparing the compound of claim 1, the method comprising;
reacting a compound of formula II-a

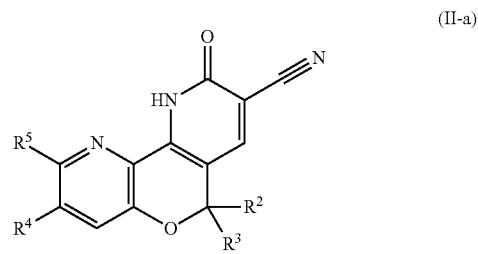

(II-a)

in the presence of
i. a base and $R^1$-LG or
ii. $R^1$—$B(OH)_2$ or $R^1$—$BF_3M$, a copper-salt, and an amine, to obtain a compound of formula II-b

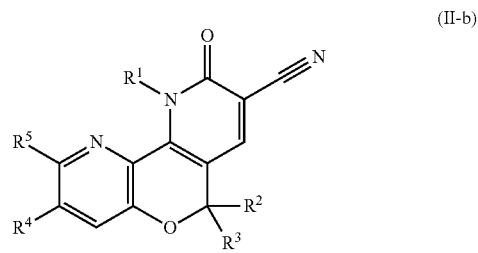

(II-b)

wherein
$R^1$ is selected from the group consisting of a linear or branched $C_1$ to $C_6$ alkyl, a $C_3$ to $C_5$ cycloalkyl, a $C_1$-$C_3$-alkyl-$C_3$-$C_5$-cycloalkyl, and a cyclic ether comprising 4 to 5 ring atoms,
wherein said $C_1$ to $C_6$ linear or branched alkyl is optionally substituted with one or more substituents selected from the group consisting of fluoro, chloro, hydroxy and $C_1$ to $C_3$ alkoxy, wherein said $C_3$ to $C_5$ cycloalkyl and said $C_1$-$C_3$-alkyl-$C_3$-$C_5$-cycloalkyl may optionally be substituted with one or more substituents selected from the group consisting of fluoro, chloro, $C_1$ to $C_3$ alkyl, hydroxy and $C_1$ to $C_3$ alkoxy, and wherein said cyclic ether comprising 4 to 5 ring atoms is optionally substituted with one or more substituents selected from the group consisting of fluoro, chloro, $C_1$ to $C_3$ alkyl, hydroxy and $C_1$ to $C_3$ alkoxy;

$R^2$, $R^3$, $R^4$ and $R^5$ in the formulae II-a and II-b have the same definition as in claim 1;

LG is a leaving group; and

M is an alkali metal.

25. The method according to claim 24, further comprising hydrolyzing the compound of formula II-a or II-b

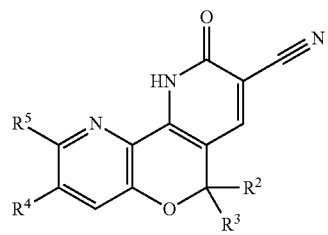
(II-a)

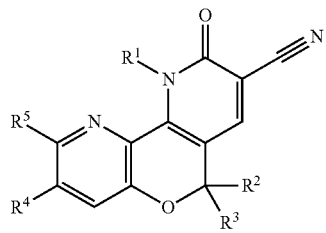
(II-b)

in the presence of an acid or a base
to obtain the compound of formula (I)

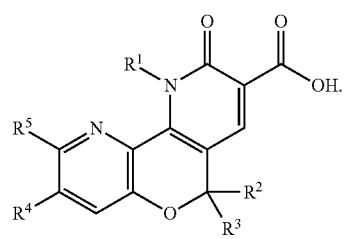
(I)

wherein $R^1$, $R^2$, $R^3$, $R^4$ and $R^5$ have the same definition as in claim 1.

* * * * *